(12) United States Patent
Mori et al.

(10) Patent No.: US 8,199,984 B2
(45) Date of Patent: Jun. 12, 2012

(54) SYSTEM THAT ASSISTS IN OBSERVING A LUMINAL ORGAN USING THE STRUCTURE OF THE LUMINAL ORGAN

(75) Inventors: Kensaku Mori, Nagoya (JP); Takayuki Kitasaka, Nagoya (JP); Daisuke Deguchi, Nagoya (JP)

(73) Assignee: National University Corporation Nagoya University, Nagoya (JP)

( * ) Notice: Subject to any disclaimer, the term of this patent is extended or adjusted under 35 U.S.C. 154(b) by 835 days.

(21) Appl. No.: 12/226,922

(22) PCT Filed: Feb. 17, 2007

(86) PCT No.: PCT/JP2007/052894
§ 371 (c)(1),
(2), (4) Date: Oct. 31, 2008

(87) PCT Pub. No.: WO2007/129493
PCT Pub. Date: Nov. 15, 2007

(65) Prior Publication Data
US 2009/0161927 A1    Jun. 25, 2009

(30) Foreign Application Priority Data
May 2, 2006 (JP) .................................. 2006-128681

(51) Int. Cl.
*G06K 9/00* (2006.01)
*A61B 1/04* (2006.01)
(52) U.S. Cl. ....................................... 382/128; 600/111
(58) Field of Classification Search .................. 382/128, 382/130, 131; 348/42, 45–50, 65; 600/109–111, 600/160, 166, 921; 250/208.1, 214.1, 214 R, 250/221, 559.4, 559.45, 559.29, 559.19, 250/559.07
See application file for complete search history.

(56) References Cited

U.S. PATENT DOCUMENTS
5,699,799 A * 12/1997 Xu et al. ...................... 600/407
5,920,319 A * 7/1999 Vining et al. ................. 345/420
(Continued)

FOREIGN PATENT DOCUMENTS
JP    A-2000-135215    5/2000
(Continued)

OTHER PUBLICATIONS

Kitasaka et al.; "A Method for Extraction of Bronchus Regions from 3D Chest X-ray CT Images by Analyzing Structural Features of the Bronchus;" *Forma*; 2002; pp. 321-338; vol. 17.
(Continued)

*Primary Examiner* — Que T Le
*Assistant Examiner* — Jennifer Bennett
(74) *Attorney, Agent, or Firm* — Oliff & Berridge, PLC

(57) ABSTRACT

Medical image observation assisting system 1 including CT-image-data retrieving portion 10, CT-image-data storing portion 11, information extracting portion 12, anatomical information DB13, point of view/line of view setting portion 14, luminal organ image generating portion 15, anatomical nomenclature information generating portion 16, branch specifying portion 17, image synthesizing and displaying portion 18 and user I/F control portion 19. The point of view/line of view setting portion 14 sets a point of view and line of view for observing an external profile of a luminal organ, on the basis of structure information of the luminal organ extracted by the information extracting portion 12, while a point of interest is kept substantially on a centerline of the organ.

18 Claims, 42 Drawing Sheets

U.S. PATENT DOCUMENTS

| | | | |
|---|---|---|---|
| 6,343,936 B1 * | 2/2002 | Kaufman et al. | 434/262 |
| 6,346,940 B1 * | 2/2002 | Fukunaga | 345/427 |
| 2004/0249270 A1 | 12/2004 | Kondo et al. | |

FOREIGN PATENT DOCUMENTS

| | | |
|---|---|---|
| JP | A-2000-163555 | 6/2000 |
| JP | A-2002-345725 | 12/2002 |
| JP | A-2003-265408 | 9/2003 |
| JP | A-2004-180940 | 7/2004 |
| JP | A-2004-230086 | 8/2004 |
| JP | A-2004-283373 | 10/2004 |
| JP | A-2006-042969 | 2/2006 |
| JP | A-2006-068351 | 3/2006 |
| WO | WO 2004/010857 A1 | 2/2004 |

OTHER PUBLICATIONS

Ishitani et al.; "A Study of Self-Calibration Method on Bronchoscope Navigation System;" *IEICE Technical Report*; Aug. 25, 2006; vol. 106, No. 225.

Hayashi et al.; "A Method for Detecting Liver Cancer Using Two Phase 3D CT Images;" *IEICE Technical Report*; Aug. 26, 2006; vol. 106, No. 226.

Deguchi et al.; "A method for bronchoscope tracking using a ultra-tiny electromagnetic tracker without fiducial markers;" *Computer Aided Diagnosis of Medical* Images; Oct. 27, 2006; pp. 161-162. (abstract only).

\* cited by examiner

FIG.37
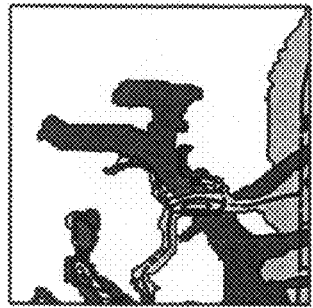
EXTERNAL PROFILE IMAGE AT FIRST POINT OF INTEREST
EXTERNAL PROFILE IMAGE AT SECOND POINT OF INTEREST
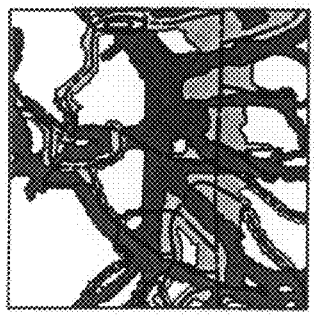
EXTERNAL PROFILE IMAGE AT THIRD POINT OF INTEREST
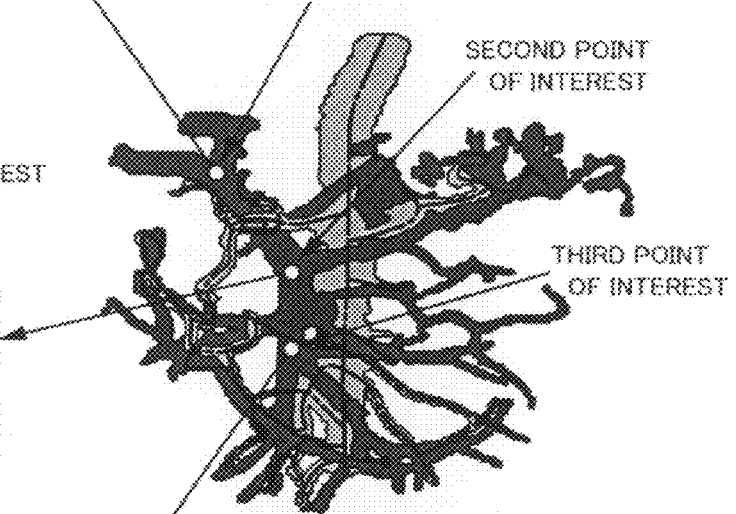
FIRST POINT OF INTEREST
SECOND POINT OF INTEREST
THIRD POINT OF INTEREST — VIRTUAL CENTERLINE c
● MEASURED POINT $p_j$ ● : $p_i$
○ : $q_i$
— : c FIG.49
| | VIRTUAL IMAGE | BIFURCATION FEATURE INFORMATION |
|---|---|---|
| case 1 | 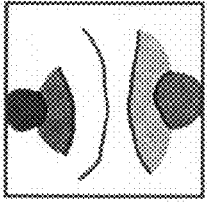 | 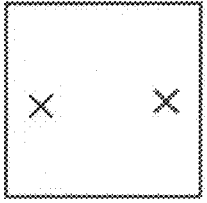 |
| case 2 | 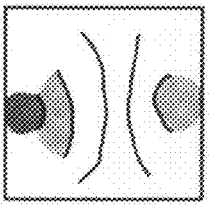 | 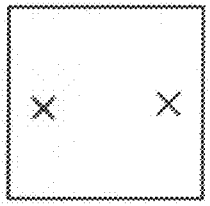 |
| case 3 | 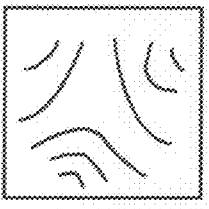 | 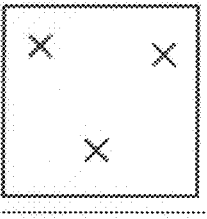 |
| case 4 | 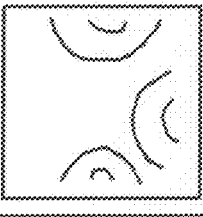 | 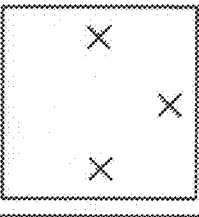 |

(REAL ENDOSCOPE IMAGE)  (VIRTUAL ENDOSCOPE IMAGE)

(REAL ENDOSCOPE IMAGE)  (VIRTUAL ENDOSCOPE IMAGE)  (3-DIMENSIONAL IMAGE)

SYSTEM THAT ASSISTS IN OBSERVING A LUMINAL ORGAN USING THE STRUCTURE OF THE LUMINAL ORGAN

TECHNICAL FIELD

The present invention relates to a medical image observation assisting system for assisting observation of an external profile of a luminal organ.

BACKGROUND ART

Recently, a diagnosis based on an image is widely implemented. For instance, an intended diagnosis of a subject body is implemented on the basis of three-dimensional image data which is obtained by an X-ray CT (computed tomography) device or the like and which represents an appearance of a portion within the subject body.

The CT device is configured to move the subject body in a direction of its axis while continuously turning an X-ray irradiator or detector, for performing continuous helical scanning of a three-dimensional region of the subject body, to generate a three-dimensional tomographic image by superimposing continuous slices of the three-dimensional region on each other.

An example of such a three-dimensional image is a three-dimensional image of a truncus vascular region or a bronchial region of a lung. The three-dimensional image of the vascular region is obtained for accurate detection of a three-dimensional structure prior to a colonic cancer operation, for example, to determine a colonic part to be excised, and the vascular parts to be ligated (by a ligature). For diagnosing the lung cancer to determine a bronchus around which the lung cancer exists, it is necessary to clearly display a tree structure of the bronchus at the position of the lung cancer.

Patent Document 1 (JP-2000-135215 A) discloses an example of a known method of displaying an image of a luminal organ, which method uses a device for navigation of a bronchial endoscope to a target region of a bronchus of the subject body, by generating a three-dimensional image of a duct or tube within the subject body on the basis of image data of a three-dimensional region of the bronchus, obtaining a path to a target point along the duct within the generated three-dimensional image, generating a virtual endoscopic image of the duct along the path, on the basis of the image data, and displaying the generated virtual endoscopic image.

However, the above-described prior art method for internal observation of the subject body suffers from extreme difficulty in detecting a positional relationship with the adjacent or neighboring other organs. Accurate detection of the luminal structure together with the positional relationship with the other organs is essential and important irrespective of imaging diagnosis, endoscopic inspection or operation, and laparotomy (abdominal incision). In this respect, there has been a need of an assisting system to facilitate such diagnosis, inspection, operation and laparotomy.

On the other hand, it is necessary to extract suitable information of a desired organ, for example, luminal information of the bronchus, from the image data of the three-dimensional region, for generating the three-dimensional image of the duct within the subject body, on the basis of the three-dimensional data of the subject body. In this respect, non-Patent Document 1 (T. Kitasaka, K. Mori, J. Hasegawa and J. Toriwaki: "A Method for Extraction of Bronchus Regions from 3D Chest X-ray CT image by Analyzing Structural Features of the Bronchus", Forma 17. pp. 321-338 (2002)), for example, proposes a so-called "segmentation processing", which comprises setting a VOI (volume of interest) of a predetermined size consisting of predetermined voxels of the three-dimensional region of the subject body, and extracting suitable information of a desired organ, for example, luminal region information of the bronchus, from the image data of the three-dimensional image data within the VOI, while segmenting the VOI in the direction of the axis of the subject body Patent Document: JP-2000-135215 A
Non-Patent Document 1:
T. Kitasaka, K. Mori, J. Hasegawa and J. Toriwaki: "A Method for Extraction of Bronchus Regions from 3D Chest X-ray CT image by Analyzing Structural Features of the Bronchus", Forma 17. pp. 321-338 (2002)
Patent Document 2: JP-2004-180940 A
Patent Document 3: WO 2004/010857 A1
Patent Document 4: JP-2006-68351 A
Patent Document 5: JP-2004-230086 A
Patent Document 6: JP-2000-163555 A
Patent Document 7: JP-2003-265408 A

DISCLOSURE OF THE INVENTION

Object Achieved by the Invention

However, there are problems of difficulty in finding out pathologic regions of a duct such as blood vessels having a complicated structure with multiple stages of bifurcation or branching, and difficulty in detecting the blood vessels of interest in a network of a large number of extremely thin blood vessels. The device disclosed in the above-identified Patent Document 1 is configured to obtain a virtual endoscopic image of an interior of a desired luminal organ as seen from a fixed point of view, and cannot be used to detect an external profile of the luminal organ upon laparotomy. Further, even a system configured to observe the external profile of the luminal organ from a desired point of view has difficulty of observing or detecting in detail the organ structure, because of structural complexity of blood vessels or other luminal organs.

It is true that the segmentation processing disclosed in the above-identified non-Patent Document 1 can extract the duct region information of the desired luminal organ from the three-dimensional image of the subject body. However, the extraction of the duct region information is implemented by threshold-value-based extraction processing using a single threshold value, or by filter extraction processing using an image emphasizing filter common to entirety of the image, resulting in a failure to assure a sufficiently high degree of extraction accuracy where the threshold value or emphasizing filter used for the peripheral regions of the tree structure of the luminal organ or for predetermined anatomical regions is used for the proximal region.

On the other hand, the above-identified Patent Document 2 proposes an endoscopic device having contracted-image generating means for a plurality of contracted three-dimensional images at all points of bifurcation or branching of a cavity within the subject body, image turning means for turning the contracted three-dimensional images generated by the contacted-image generating means, and turning-amount-data memory means for storing turning amount data relating to turning of the three-dimensional images rotated by the image turning means, in relation to the three-dimensional images. However, the image turning means for turning the three-dimensional images must be operated on the basis of a manual operation by an operator, and this manual operation is difficult during manipulation of an endoscope of the endoscopic device.

The above-identified Patent Document 3 proposes an endoscopic device characterized by navigation image generating means for generating a navigation image by adding the contracted three-dimensional images at all points of bifurcation or branching of a cavity within the subject body to the navigation image consisting of an endoscopic image of the cavity obtained by an endoscope and the above-indicated three-dimensional images. Where the contracted images are merely three-dimensional images at the points of bifurcation and are similar to each other, the operator of the endoscopic device may possibly be confused with the three-dimensional images.

The above-identified Patent Document 4 proposes a medical image processing method of obtaining data of matrix of centerline points of a tubular structure of the subject body, which method is based on a group of a plurality of volume data sets in the direction of axis of time. The above-identified Patent Document 5 proposes an image processing device configured to set a desired region of a tubular structure within a spatial image data of the subject body, and to set the centerline of the tubular structure set by the region setting means. The image processing method and device disclosed in these Patent Documents 4 and 5 do not refer to a tubular structure having bifurcated or branched regions, and do not permit setting of the centerline of such a tubular structure.

The above-identified Patent Document 6 proposes a method of extracting bifurcated regions of a tubular structure of the subject body, which method comprises specifying a start point of the bifurcated regions and a direction of a region of interest, within the regions including the region of interest (which is one of the bifurcated regions), and extracting the bifurcated regions by enlarging the bifurcated regions from the start point in the direction of the region of interest, under a condition (a condition of large-region change) that an intensity value at each point within the same region falls within a certain range and a condition (a condition of local change) that a difference between intensity values at the adjacent points is relatively small. However, the extracting method disclosed in the Patent Document 6 is applicable to a two-dimensional image in the form of a tomographic image of the subject body, but is not applicable to a three-dimensional image as obtained by the above-described helical scanning.

The above-identified Patent Document 7 proposes an endoscopic device configured to compare a real endoscopic image with virtual endoscopic images stored in a database, to determine the virtual endoscopic image most similar to the real endoscopic image, and to determine the position of the leading end and the attitude of an endoscope on the basis of the determined virtual endoscopic image. However, the endoscopic device proposed by the Patent Document 7 which compares the entirety of the real endoscopic image with the entirety of each virtual endoscopic image tends to require a relatively long time for the comparison. Further, the endoscopic device disclosed in the Patent Document 7 is configured to display the determined leading end position and attitude of the endoscope such that these position and attitude are superimposed on an MRI image or CT image. However, this superimposition has a risk of difficulty in providing the operator with sufficient information for navigating the endoscope.

It is noted that the above-indicated Patent Document 2 describes superimposition of the nomenclature of the bronchial duct or tube on the virtual endoscopic image, but does not refer to a specific method or means for such superimposition.

The present invention was made in view of the background art described above. It is an object of this invention to provide a medical image observation assisting system which permits assistance for easy and adequate observation of an external profile and detection of a structure of a luminal organ.

Means for Achieving the Object

The object indicated above can be achieved according to a first form of this invention, which provides a medical image observation assisting system, characterized by comprising (a) volume-region setting means for sequentially setting volume regions each enveloping a part of a luminal organ extending within a subject body, on the basis of three-dimensional image data of the subject body, such that the volume regions are adjacent to each other, (b) luminal-organ-region-information calculating means for repeatedly calculating luminal region data in the form of region information of the part of the luminal organ within each of the volume regions set by said volume-region setting means, on the basis the three-dimensional image data of the part of the luminal organ within the volume region, (c) luminal-organ-structure-information calculating means for calculating luminal structure data in the form of structure information of the part of the luminal organ within the volume region for which the luminal region data has been calculated by the luminal-organ-region-information calculating means, (d) virtual-centerline generating means for generating a virtual centerline extending in a longitudinal direction of the luminal organ, on the basis of the luminal structure data, (e) virtual-image generating means for generating a virtual image of the luminal organ along the virtual centerline, (f) display means for displaying the virtual image of the luminal organ, and (g) observing-position specifying means for determining an observing position for generating the virtual image, on the basis of at least one of the virtual centerline, the luminal region data and the luminal structure data, such that a region of the luminal organ displayed on the display means has a desired size, and for moving the observing position in the longitudinal direction of the luminal organ, on the basis of the virtual centerline or the luminal structure data.

Advantages of the Invention

In the medical image observation assisting system according to the first form of this invention, the volume-region setting means sequentially sets the volume regions each enveloping a part of the luminal organ extending within the subject body, on the basis of the three-dimensional image data of the subject body, such that the volume regions are adjacent to each other, and the luminal-organ-region-information calculating means repeatedly calculates the luminal region data in the form of region information of the part of the luminal organ within each of the volume regions set by the volume-region setting means, on the basis of the three-dimensional image data of the part of the luminal organ within the volume region, while the luminal-organ-structure-information calculating means calculates the luminal structure data in the form of structure information of the part of the luminal organ within the volume region for which the luminal region data has been calculated by the luminal-organ-region-information calculating means. The virtual-centerline generating means generates the virtual centerline extending in the longitudinal direction of the luminal organ, on the basis of the luminal structure data, and the virtual-image generating means generates the virtual image of the luminal organ along the virtual centerline. The display means displays the virtual image of the luminal organ, and the observing-position specifying means determines the observing position for generating the virtual image, on the basis of at least one of the virtual centerline, the luminal region data and the luminal structure data, such that the region of the luminal organ displayed on the display means has a desired size, and moves the observing position in the longitudinal direction of the luminal organ, on the basis of the virtual centerline or the luminal structure data. Accordingly, the virtual image of the luminal organ reflecting the structure information can be obtained from the three-dimensional image data. Further, the structure of the luminal organ can be exactly observed from the desired point of view of the organ, without a cumbersome operation to change the point of view. In addition, the observing position is calculated such that the region of the luminal organ displayed on the display means has a desired size, and the ratio of magnification of the external profile image of the luminal organ displayed on the display means is automatically adjusted, so that the observer can easily observe the luminal organ along its direction of extension, even where the organ has a large length. The desired size of the displayed region of the luminal organ is selected by the observer according to the specific application or use of the present assisting system. When the observer wants to check a blood vessel over the entire length, for example, the blood vessel is displayed with a comparatively small size. When the observer wants to observe the condition of a portion of the wall surface of the blood vessel, that portion is displayed with a comparatively large size.

Preferably, the medical image observation assisting system is characterized by further comprising (a) anatomical-structure-information storing means for storing anatomical structure information including at least anatomical nomenclature information, and (b) anatomical-nomenclature correlating means for correlating the anatomical nomenclature information stored in the anatomical-structure-information storing means, with the luminal structure data. In this preferred arrangement wherein the luminal structure data is correlated with the anatomical structure information, the luminal structure data and the anatomical structure information correlated with the luminal structure data can be handled as a set of data.

Preferably, the medical image observation assisting system is characterized by comprising image synthesizing means for displaying anatomical nomenclature of the luminal organ on the virtual image displayed on the display means, on the basis of correlation of the anatomical nomenclature by the anatomical-nomenclature correlating means. In this case, the observation of the luminal organ can be facilitated by the anatomical nomenclature of the luminal organ which is displayed by the image synthesizing means, on the virtual image displayed on the display means.

Preferably, the virtual-image generating means of the medical image observation assisting system is configured to change an image processing method on the basis of the anatomical structure information or the luminal structure data. In this preferred arrangement which permits automatic or manual change of the image processing method depending upon the specific part of the luminal organ, the luminal region data can be accurately extracted.

Preferably, the medical image observation assisting system is characterized by comprising (a) endoscope-position detecting means for detecting a relative position of a leading end portion of an endoscope actually inserted into the subject body, and (b) first real-image observing-position estimating means for comparing the position of the leading end portion of the endoscope detected by the endoscope-position detecting means, with the luminal organ structure data, to thereby estimate a real-image observing position which is a position of the leading end portion of the endoscope within the luminal organ. In this case, the relative position of the leading end portion of the endoscope detected by the endoscope position detecting means is compared with the organ structure data, to estimate the real image observing position, so that the leading end position of the endoscope, which corresponds to the real image observing position, can be further exactly detected.

Preferably, the medical image observation assisting system is characterized by comprising (a) virtual-image storing means for storing each of the plurality of virtual images generated by the virtual-image generating means, which each virtual image includes a bifurcated portion of the luminal organ, such that the above-indicated each virtual image is correlated with the luminal structure data corresponding to the above-indicated each virtual image, and (b) second real-image observing-position estimating means for extracting features which appear on a real endoscope image taken by an endoscope actually inserted into the subject body and which correspond to the luminal structure data, verifying the extracted features against or with respect to the luminal structure data stored in the virtual-image storing means, and estimating the observing position of the virtual image corresponding to the luminal structure data verified to match the extracted features, as the observing position of the real endoscope image.

Preferably, the medical image observation assisting system is characterized in that the image synthesizing means displays the real endoscope image and the virtual image which corresponds to the real endoscope image and which is generated by the virtual-image generating means such that the real endoscope image and the virtual image can be compared with each other. In this case, the real endoscope image and the virtual image can be compared with each other on the display means.

Preferably, the medical image observation assisting system is characterized in that the virtual-image generating means generates the virtual image such that the real-image observing position estimated by the first real-image observing-position estimating means is determined as the observing position of the virtual image. In this case, the virtual image is generated such that the observing position of the virtual image is the real-image observing position estimated by the first real-image observing-position estimating means. That is, the virtual image is obtained at the observing position which is estimated to be the real-image observing position at which the real endoscope image has been obtained.

Preferably, the medical image observation assisting system is characterized in that the virtual-image generating means generates the virtual image such that the real-image observing position estimated by the second real-image observing-position estimating means is determined as the observing position of the virtual image. In this case, the virtual image is generated such that the observing position of the virtual image is the real-image observing position estimated by the second real-image position-position estimating means. That is, the virtual image is obtained at the observing position which is estimated to be the real-image observing position at which the real endoscope image has been obtained.

Preferably, the medical image observation assisting system is characterized in that the above-described image synthesizing means displays the anatomical nomenclature of the luminal organ on a real endoscope image displayed on the display means, on the basis of correlation of the anatomical nomenclature by the anatomical-nomenclature correlating means. In this case, the luminal organ the real endoscope image of which is displayed on the display means is provided with the anatomical nomenclature correlated by the anatomical-nomenclature correlating means, so that the portion of the luminal organ the real endoscope image of which is displayed can be identified by the anatomical nomenclature.

Preferably, the medical image observation assisting system is characterized in that the virtual image and the real endoscope image corresponding to the luminal structure data have at least one feature selected from the number of luminal structural portions, the positions of the luminal structural portions, and the luminosity of the image of the luminal structural portions. In this case, the real endoscope image and the virtual image are verified or compared with respect to each other on the basis of at least one feature of the virtual image and endoscope image which corresponds to the luminal structure data and which is selected from the number and positions of the luminal structure portions and the luminosity of the image of the luminally structural portions. Thus, it is not necessary to verify the entirety of the images.

Preferably, the medical image observation assisting system is characterized in that the second real-image observing-position estimating means comprises virtual-image learning means for implementing learning modification of contents of the virtual-image storing means, on the basis of a result of the verification by the second real-image observing-position estimating means. In this case, the virtual-image learning means of the second real-image observing-position estimating means modifies the contents of the virtual-image storing means on the basis of the above-indicated verification, so that the accuracy of verification is improved as the verification is repeated.

Preferably, the medical image observation assisting system is characterized by (a) comprising navigating means for displaying an image for navigating a path from a position of insertion of an endoscope into the luminal organ to a target portion of the luminal organ, and (b) the navigating means displays an indication of one of a plurality of branches of the luminal organ open at a bifurcated portion thereof indicated on the real endoscope image displayed on the display means, the endoscope being advanced into said one of the plurality of branches. In this case, the operator can recognize one of the plurality of branches of the luminal organ at each bifurcated portion into which the endoscope should be advanced toward the target portion, owing to the navigating means which is configured to indicate that branch at the bifurcated portion indicated on the real endoscope image displayed on the display means, so that the endoscope can be easily inserted to the target portion.

Preferably, the medical image observation assisting system is characterized by (a) comprising navigating means for displaying an image for navigating a path from a position of insertion of an endoscope into the luminal organ to a target portion of the luminal organ, and (b) the navigating means automatically generates the path, and displays a plurality of anatomical names correlated by the anatomical-nomenclature correlating means with respective organs of the luminal organs defining the path, in the order from the position of insertion of the endoscope to the target portion. In this case, the displayed anatomical names permit the operator to recognize the path to the target portion of the luminal organ to which the endoscope is inserted, owing to the navigating means which is configured to automatically generates the path, and to display the plurality of anatomical names correlated with the respective organs of the luminal organ defining the path, in the order from the position of insertion of the endoscope to the target portion.

It is also preferable that (a) the medical image observation assisting system comprises extraluminal tissue extracting means for extracting extraluminal tissue structure information relating to a structure of an extraluminal tissue existing outside the luminal organ in the subject body, on the basis of the three-dimensional image data, and that (b) the virtual-image generating means displays the virtual image of the luminal organ and a virtual image of the extraluminal tissue within the same screen in the same scale while maintaining an actual positional relationship between the virtual images. In this case, it is possible to recognize in the above-indicated virtual images the position and size of the extraluminal tissue existing outside the luminal organ, on the basis of the above-described three-dimensional image data.

Preferably, (a) the anatomical-structure-information storing means stores anatomical structure information including at least anatomical nomenclature information for the luminal organ and at least an anatomical number for the extraluminal tissue, and (b) the anatomical-nomenclature correlating means correlates the anatomical nomenclature information of the luminal organ stored in the anatomical-structure-information storing means, with the luminal structure data, and correlates the anatomical number of the extraluminal tissue stored in the anatomical-structure-information storing means, with the extraluminal tissue structure information. In this case, the anatomical-nomenclature correlating means correlates the anatomical number with the extraluminal tissue, as well as correlates the anatomical nomenclature with the luminal organ.

Preferably, the medical image observation assisting system is characterized by comprising image synthesizing means for displaying anatomical name of the luminal organ and the anatomical number of the extraluminal tissue on the virtual images displayed on the display means, on the basis of correlation of the anatomical name and the anatomical number by the anatomical-nomenclature correlating means. In this case, the anatomical name of the luminal organ and the anatomical number of the extraluminal tissue are displayed on the virtual images displayed on the display means, by the image synthesizing and displaying means, so that the observation of the luminal organ is facilitated.

Preferably, the virtual-image generating means of the medical image observation assisting system changes an image processing method on the basis of at least one of the anatomical structure information, the luminal structure data and the extraluminal tissue structure information. In this preferred arrangement which permits automatic or manual change of the image processing method depending upon the specific part of the luminal organ or extraluminal tissue, the luminal region data can be accurately extracted.

It is also preferable that the medical image observation assisting system is characterized in that when the extraluminal tissue is set as a target portion, the navigating means sets a portion of the luminal organ which is located close to the extraluminal tissue and into which the endoscope can be inserted, as the target portion of the luminal organ. In this case, the operator is merely required to set the extraluminal tissue as the target position, for assistance by the navigating means to insert the endoscope to the portion of the luminal organ which is located close to the extraluminal tissue and into which the endoscope can be inserted.

Preferably, the medical image observation assisting system is characterized in that the extraluminal tissue is a lymph node, while the luminal organ is a blood vessel. In this case, the endoscope can be inserted through the blood vessel up to the portion which is located close to the lymph node and into which the endoscope can be inserted, by setting that portion of the blood vessel as the target portion, even where it is difficult to insert the endoscope directly into a lymphatic duct leading to the lymph node which is the luminal organ.

BRIEF DESCRIPTION OF THE DRAWINGS

FIG. 37 is a view for explaining a plurality of points of interest positions, and a generated external profile image of a luminal organ.

FIG. 49 is a view for explaining features in the image corresponding to the organ structure information.

NOMENCLATURE OF ELEMENTS

1: Medical image observation assisting system (Computer)
2: Display means (Monitor)
12: Information extracting portion (Volume-region setting means)
12: Information extracting portion (Luminal-organ-region-information calculating means)
12: Information extracting portion (Luminal-organ-structure-information calculating means)
12: Information extracting portion (Virtual-centerline generating means)
12: Information extracting portion (Anatomical-nomenclature correlating means)
13: Anatomical-structure-information storing means (Anatomical information database)
14: Point of view/line of view setting portion (Observing-position specifying means)
15: Luminal organ image generating portion (Virtual-image generating means)
18: Image synthesizing and displaying portion (Image synthesizing means)
35: Luminal region data (Organ region information)
37: Luminal structure data (Organ structure information)
75: Observing position
82: Endoscope position detecting portion (Endoscope position detecting means)
84: Endoscope
102: Virtual image learning portion (Virtual image learning means)
110: Virtual image memory portion (Virtual image memory means)
112: First real image observing position estimating portion (First real-image observing-position estimating means)
114: Second real image observing position estimating portion (Second real-image observing-position estimating means)
116: Navigation portion (Navigating means)
12h: Extraluminal tissue extracting portion (Extraluminal tissue extracting means)
VOI: Volume of interest region
c: Virtual centerline

BEST MODE FOR CARRYING OUT THE INVENTION

There will be described the embodiments of this invention by reference to the drawings.

Embodiment 1

Figure 1:
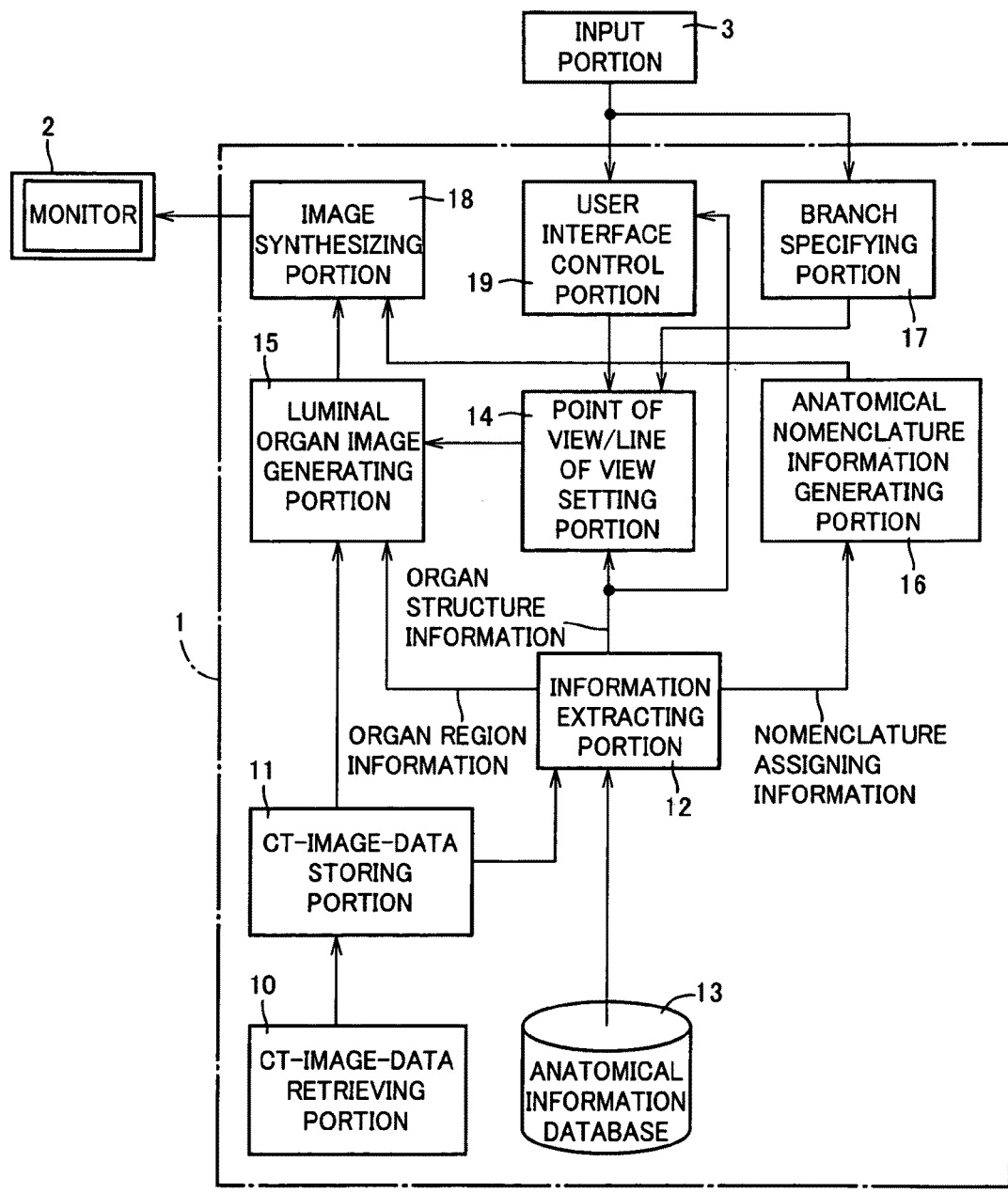
FIG. 1 is a functional block diagram showing major functions of a medical image observation assisting system according to Embodiment 1 of this invention.
Figure 2:
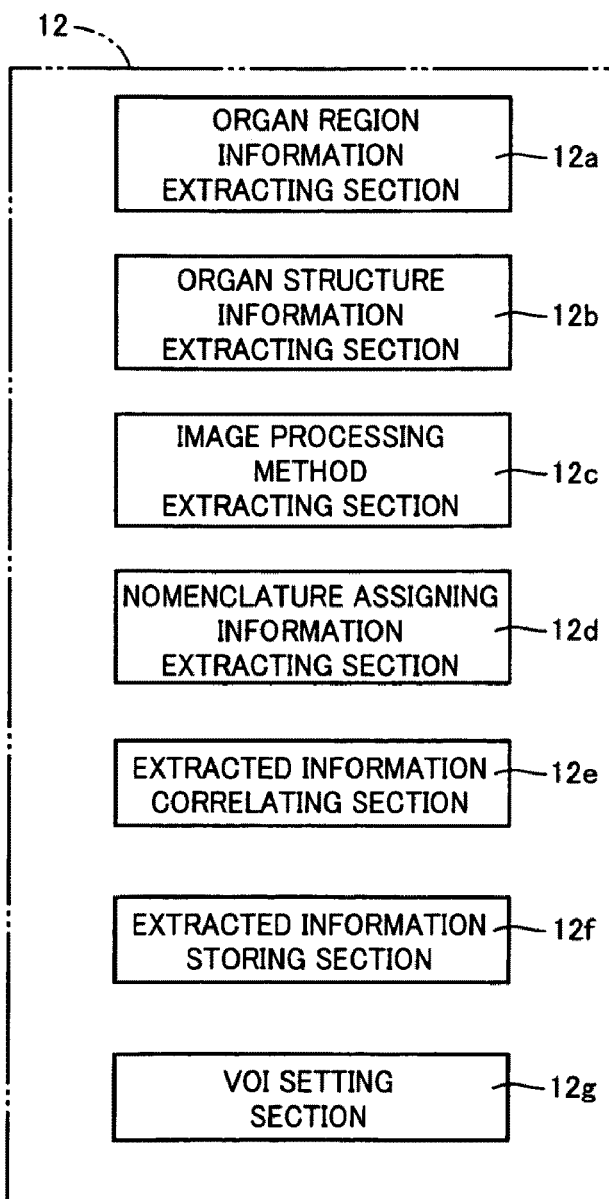
FIG. 2 is a block diagram showing functions of an information extracting portion shown in FIG. 1.
Figure 3:
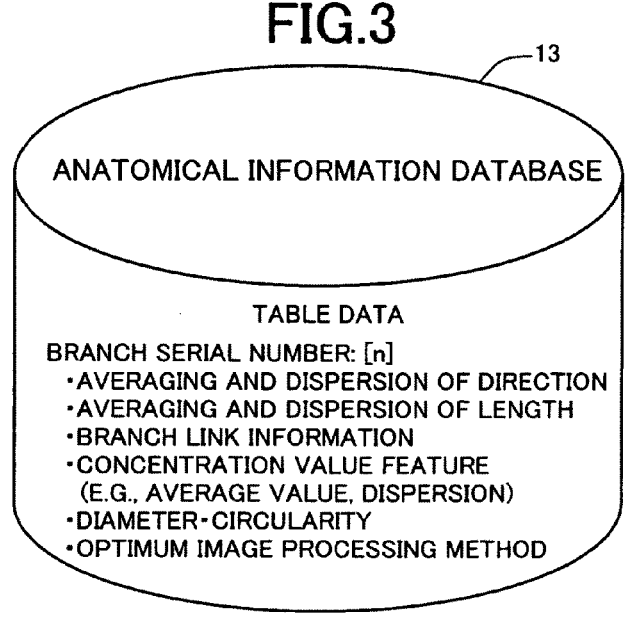
FIG. 3 is a view for explaining information stored in an anatomical information database shown in FIG. 1.
Figure 4:
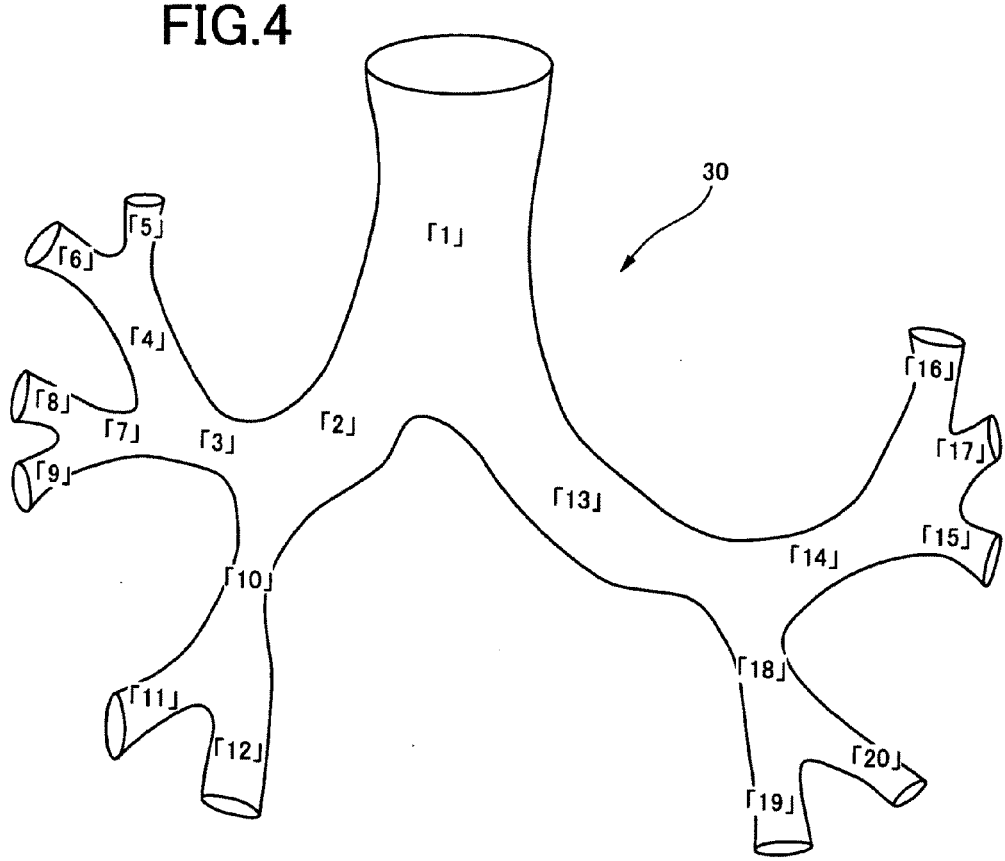
FIG. 4 is a view showing an exemplary model various portions of a luminal organ, which portions are represented by respective branch serial numbers.

FIGS. 1-38 relate to Embodiment 1 of the present invention. FIG. 1 is a functional block diagram showing major functions of a medical image observation assisting system, and FIG. 2 is a block diagram showing functions of an information extracting portion shown in FIG. 1. FIG. 3 is a first view for explaining an anatomical information database shown in FIG. 1, and FIG. 4 is a second view for explaining the anatomical information database shown in FIG. 1.

Figure 5:
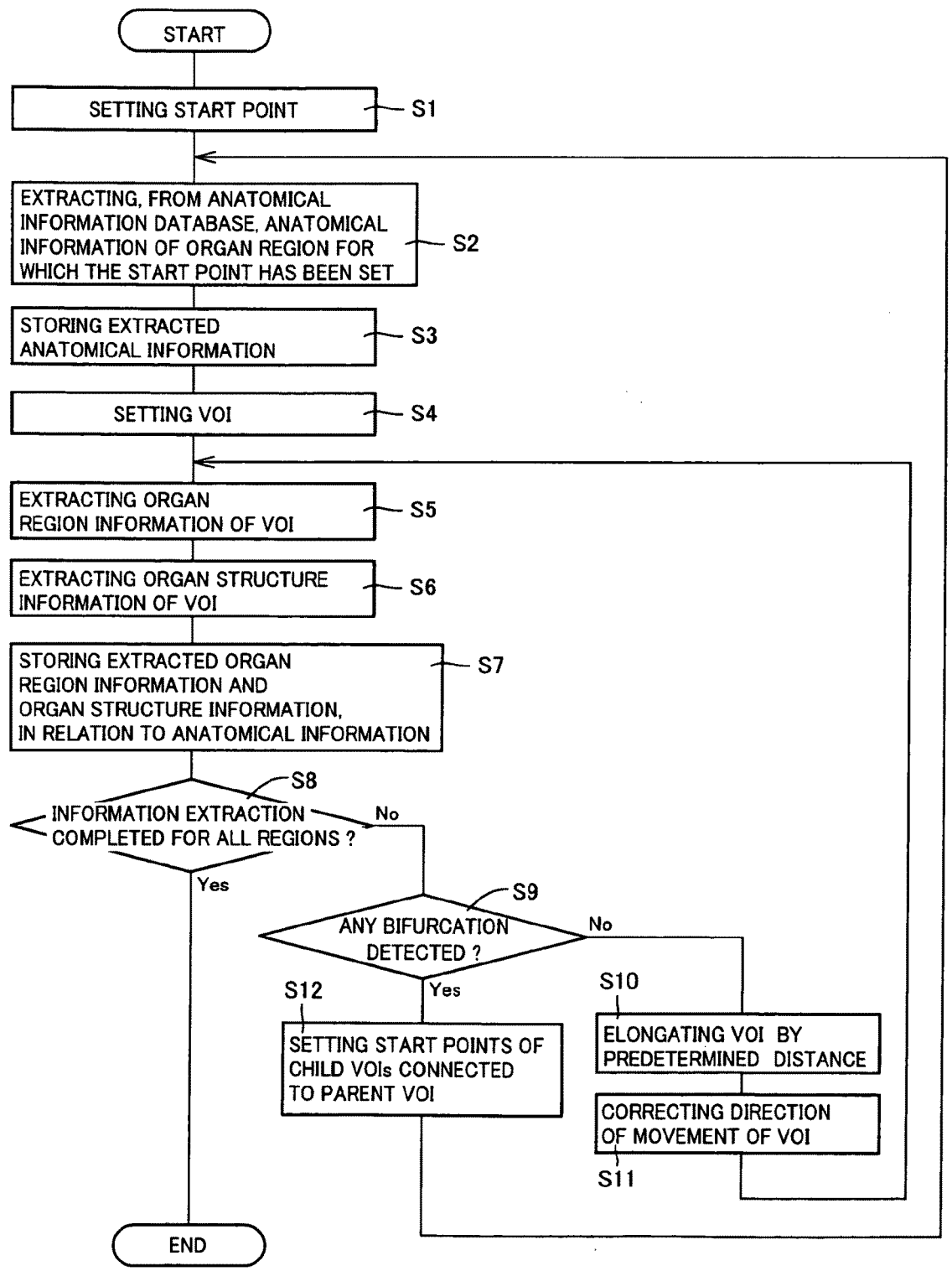
FIG. 5 is a flow chart illustrating a flow of extraction of organ region information and nomenclature of the organ structure information and branch portions by the information extracting portion shown in FIG. 1.
Figure 6:
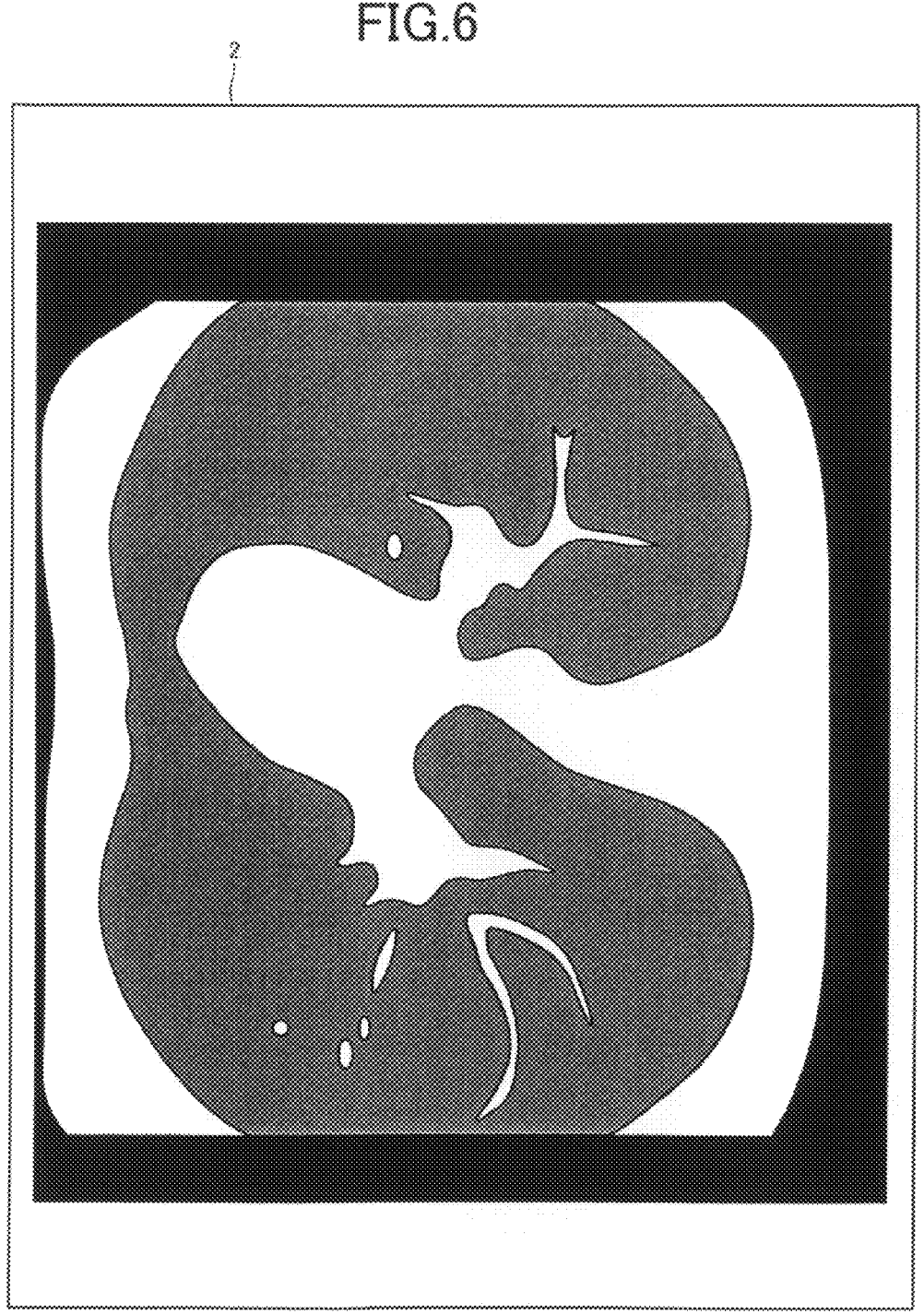
FIG. 6 is a view showing an exemplary three-dimensional image in the form of a tomographic image based on CT image data.

FIG. 5 is a flow chart illustrating a flow of extraction of organ region information, organ structure information and nomenclature of branch portions by the information extracting portion shown in FIG. 1, and FIGS. 6-31 are views indicating details of the flow illustrated in FIG. 5.

Figure 32:
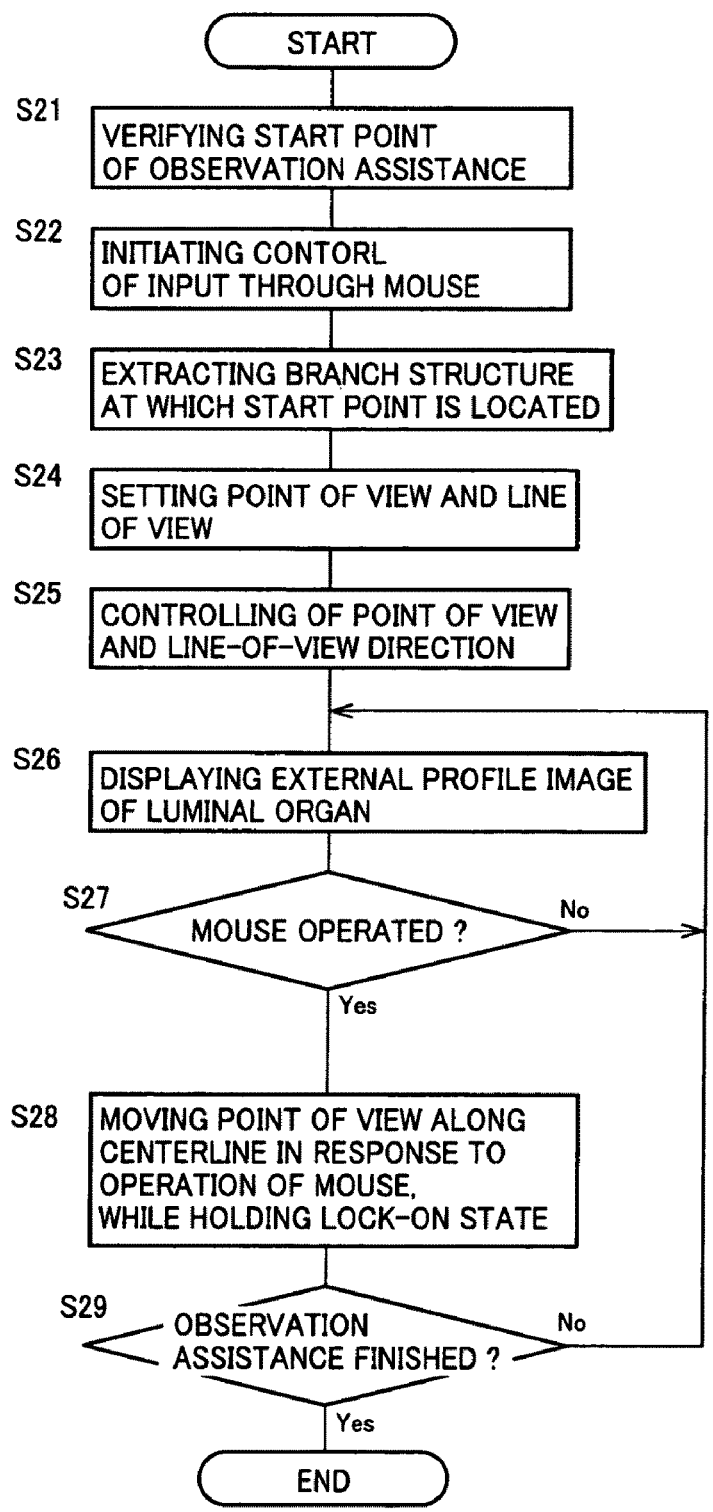
FIG. 32 is a flow chart illustrating an observation assisting operation of the luminal organ observation assisting system of FIG. 1.
Figure 33:
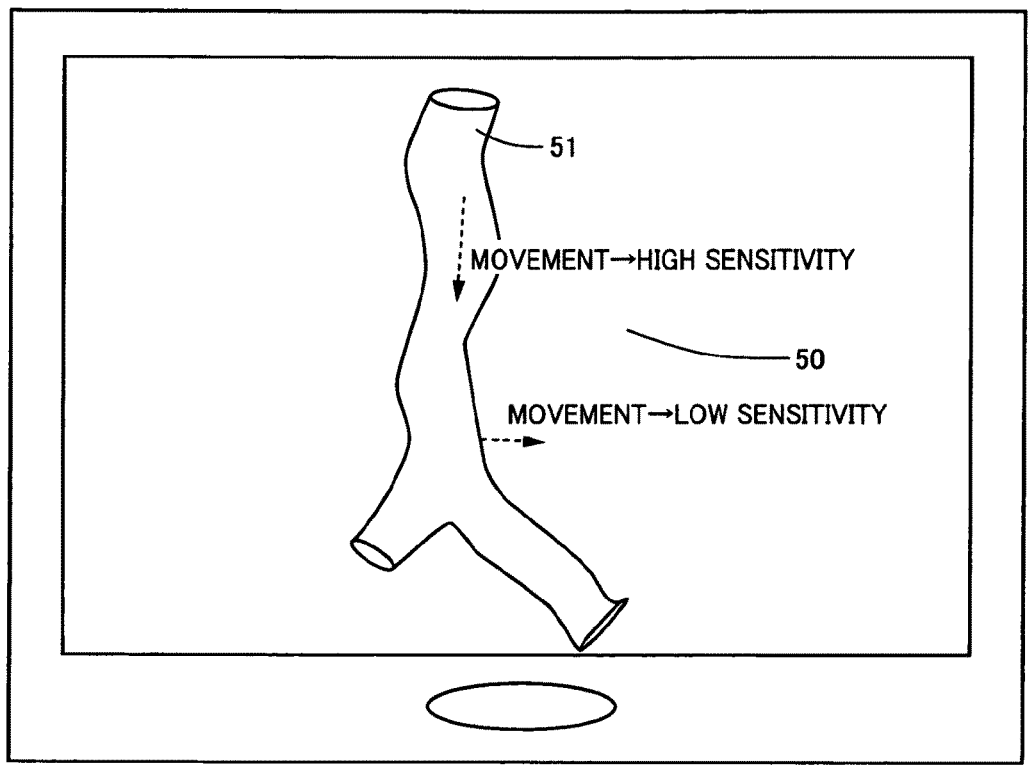
FIG. 33 is a view showing a generated external profile of a luminal organ as displayed on a monitor.
Figure 34:
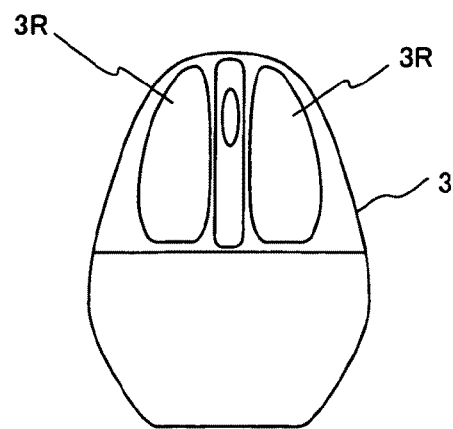
FIG. 34 is a view showing an example of a mouse which constitutes an input portion.

FIG. 32 is a flow chart illustrating a flow of an operation to assist observation of a luminal organ in the medical image observation assisting system of FIG. 1, and FIGS. 34-38 are views indicating details of the flow illustrated in FIG. 33.

The medical image observation assisting system 1 of the present embodiment is constituted by a so-called computer which incorporates a ROM storing predetermined information such that the stored information is readable, a RAM for storing information such that the information is readable and writable as needed, and a CPU (central processing unit) operable to implement arithmetic operations on the information according to stored control programs. The computer 1 serving as the medical image observation assisting system extracts region information and structure information of the luminal organ specified by an input portion 3 having a pointing device such as a mouse, on the basis of CT image data. The computer 1 controls a point of view and line-of-view direction for generating a virtual image. Described in detail, the computer 1 moves the point of view as an observing position along a virtual centerline which is a longitudinal direction of the luminal organ, and calculates the line-of-view direction as a direction from the point of view toward a point of interest lying on the virtual centerline. The point of interest is a center point of a region to be observed, and is a center of the virtual image. Accordingly, the line-of-view direction is the direction from the point of view toward the point of interest. A state of the system in which the point of interest is located on the virtual centerline and the point of view and the line-of-view direction are controlled will be hereinafter referred to as a "lock on state". The luminal organ is represented by the virtual image displayed on display means in the form of a monitor 2, for imaging diagnosis, laparotomy or abdominal incision, surgical operation under endoscopic observation, or preparation for the surgical operation under endoscopic observation.

The medical image observation assisting system 1 includes: a CT-image-data retrieving portion 10; a CT-image-data storing portion 11; an information extracting portion 12 functioning as volume-region setting means, luminal-organ-region-information calculating means, luminal-organ-structure-information calculating means, virtual-centerline generating means and anatomical-nomenclature correlating means; an anatomical information database (hereinafter abbreviated as "DB") 13 functioning as anatomical-structure-information storing means; a point of view/line of view setting portion 14 functioning as observing-position specifying means; a luminal organ image generating portion 15 functioning as virtual-image generating means; an anatomical nomenclature information generating portion 16; a branch specifying portion 17 functioning as start point specifying means; an image synthesizing and displaying portion 18 functioning as image synthesizing means; and a user interface (hereinafter abbreviated as "I/F") control portion 19 functioning as point-of-interest movement control means.

The CT-image-data retrieving portion 10 is configured to retrieve, from a MO (magnetic optical disc) device, a DVD (digital versatile disc) device or other portable memory medium, three-dimensional image data generated by a known CT device operable to take an X-ray tomographic image of a patient.

The CT-image-data storing portion 11 is configured to store the CT image data retried by the CT-image-data retrieving portion 10.

The information extracting portion 12 is configured to select a volume region in the form of a VOI (volume of interest) of the luminal organ described below, and to extract region information (organ region information) and structure information (organ structure information) of the luminal organ within the VOI. The information extracting portion 12 is further configured to correlate the region information and structure information of the luminal organ with the anatomical information stored in the anatomical information DB 13. On the basis of the structure of the luminal organ in connection with the VOI correlated with the anatomical information, the information extracting portion 12 generates a new VOI, and extract the organ region information and organ structure information of this new VOI. The information extracting portion 12 is further configured to provide the anatomical nomenclature information generating portion 16 with nomenclature assigning information for assigning nomenclature to the structure information of the VOI correlated to the anatomical information.

The point of view/line of view setting portion 14 is configured to set the point of interest on the virtual centerline of the luminal organ, and set the point of view and the line of view for observing an external profile of the luminal organ, on the basis of the stricture information of the organ extracted by the information extracting portion 12. The observing position specifying means is constituted by this point of view/line of view setting portion 14.

The luminal organ image generating portion 15 is configured to process the CT-image data stored in the CT-image-data storing portion 11, on the basis of the organ region information extracted by the information extracting portion 12, and to generate a virtual external profile image of the luminal organ as viewed from the point of view and line-of-view direction specified by the point of view/line of view setting portion 14. The virtual-image generating means is constituted by this luminal image generating portion 15.

The anatomical nomenclature information generating portion 16 is configured to generate character image data on the basis of the nomenclature assigning information received from the information extracting portion 12.

The branch specifying portion 17 is configured to specify branches of a tree structure (bifurcated structure) of the luminal organ, through a mouse or the like of the input portion 2.

The image synthesizing and displaying portion 18 is configured to combine together the virtual image of the luminal organ generated by the luminal organ image generating portion 15, and the character image data received from the above-described anatomical nomenclature information generating portion 16, and display the thus synthesized image on the monitor 2.

The user I/F control portion 19 is configured to control an input through the input portion 3 according to the settings by the point of view/line of view setting portion 14. Described more specifically, the user I/F control portion 19 controls the input through the input portion 3 such that the information input through the mouse of the input portion 3 is utilized only as information for vertically moving the image, when the lock-on state is established by the point of view/line of view setting portion 14. This aspect will be detailed later. When the lock-on state is not established by the point of view/line of view setting portion 14, the control of the information input through the mouse of the input portion 3 is cancelled.

As shown in FIG. 2, the information extracting portion 12 incorporates an organ region information extracting section 12a, an organ structure information extracting section 12b, an image processing method extracting section 12c, a nomenclature assigning information extracting section 12d, an extracted information correlating section 12e, an extracted information storing section 12f, and a VOI setting section 12g. These sections will be described in detail. Luminal-region-information calculating means is constituted by the organ region information extracting portion 12a, and luminal-organ-structure-information calculating means is constituted by the organ structure information extracting portion 12b, while volume-region setting means is constituted by the VOI setting portion 12g.

The anatomical information DB 13 consists of sets of data for respective branches of the tree structure of the luminal organ, which branches are identified by respective branch serial numbers, as indicated in FIG. 3. Described in detail, the anatomical information DB 13 consists of sets of data which corresponds to the branch serial numbers [n=natural number] and each of which consists of the following items of anatomical model information (1)-(6) as anatomical structure information:

(1) Average value information and dispersion information of the direction of extension of the branch number [n]
(2) Average value information and dispersion information of the length of the branch number [n]
(3) Branch link information indicative of the serial numbers of branches linked with the branch number [n]
(4) Concentration value features (e.g., average value information and dispersion information) of image data of the branch number [n]
(5) Diameter and sphericity (degree of sphere) of the branch number [n]
(6) Optimum image processing method of the branch number [n]

The information extracting portion 12 determines the tree structure to which the extracted VOI belongs, and stores the region information and structure information in the extracted information storing section 12f, in relation to the items of information (1)-(6) in the anatomical information DB 13, according to the determined tree structure.

There will be described an operation of the medical image observation assisting system of the present embodiment to extract the organ region information, organ structure information and branch nomenclatures, in the case of a bronchi 30 shown in FIG. 4 as the luminal organ, by reference to the flow chart of FIG. 5.

FIG. 4 shows an anatomical model in the form of the bronchi 30 having a tree structure the branches of which are identified by the respective serial numbers [n], namely, number 1 through number 20 in the specific example of FIG. 4. On the bases of the serial number [n], the anatomical information DB 13 stores the above-indicated items of information (1)-(6) for each branch of the bronchi.

The luminal organs to which the present embodiment is applicable include not only the bronchi 30, but also esophagus, blood vessels, large intestine (colon), small intestine, intestinum duodenum, stomach, bile duct, pancreatic duct proper, lymphatic duct, etc.

Figure 7:
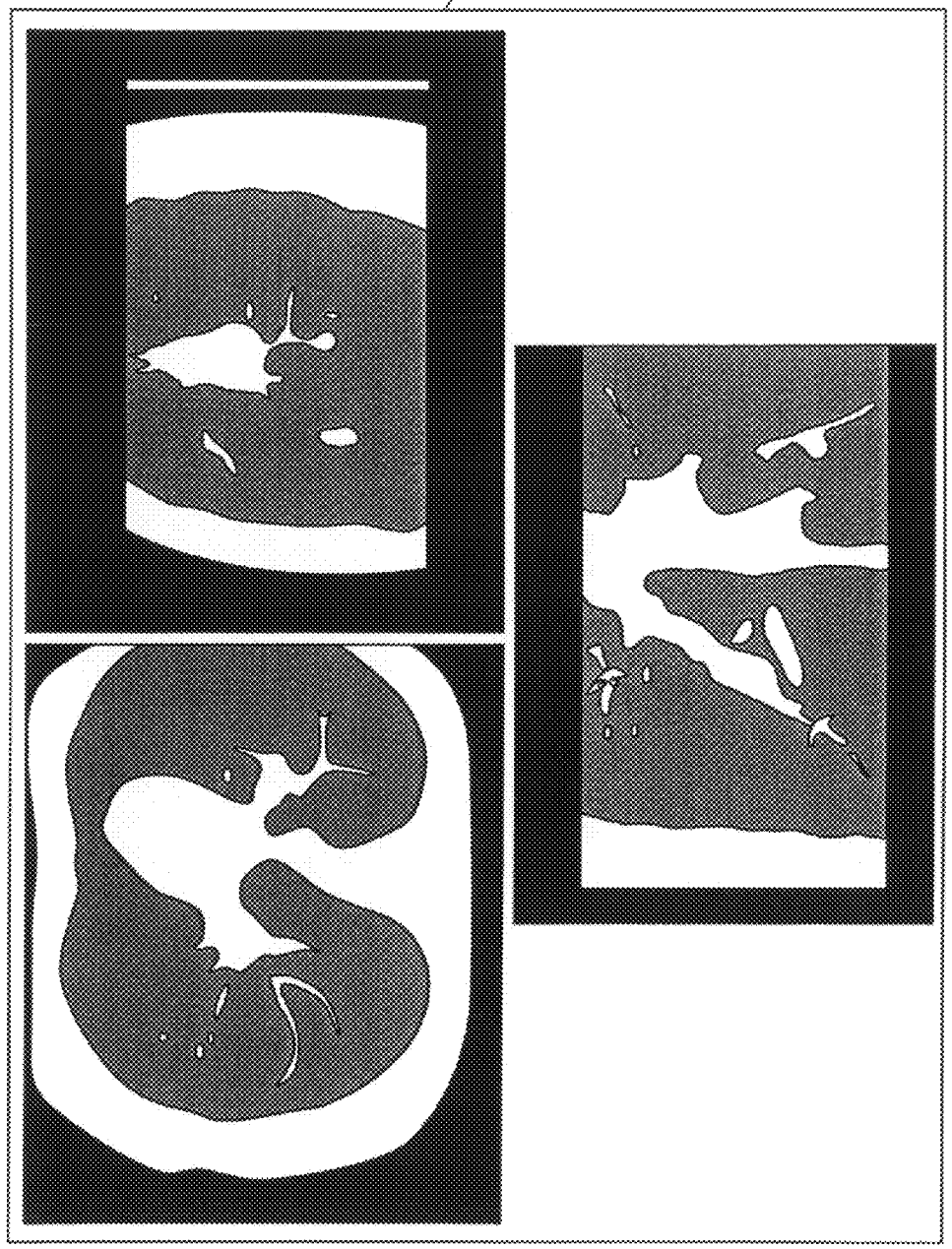
FIG. 7 is a view showing an exemplary three-dimensional image in the form of MPR (multi-plane restructured image).

The flow chart of FIG. 5 indicates a major control operation of the medical image observation assisting system 1. The control operation is initiated with step S1 (hereinafter "step" being omitted) corresponding to the branch specifying portion 17, to detect entry of a start point through the input portion 3 having the pointing device in the form of the mouse or the like. The start point is a point which lies on the tomographic image (e.g., image shown in FIG. 6) or MPR image (multiple-plane restructured image as shown in FIG. 7) displayed on the monitor 2 on the basis of the CT image data and at which the extraction of the organ region information and organ structure information is initiated.

When the entry of the start points is detected in S1, the control flow goes to S2 corresponding to the information extracting portion 12, in which the items of anatomical information (1)-(6) of all the branches of the bronchi 30 (organ regions) for which the start point has been set are extracted from the anatomical information DB 13. Then, the control flow goes to S3 in which the extracted items of anatomical information (1)-(6) are stored in the extracted information memory storing section 12f.

Figure 8:
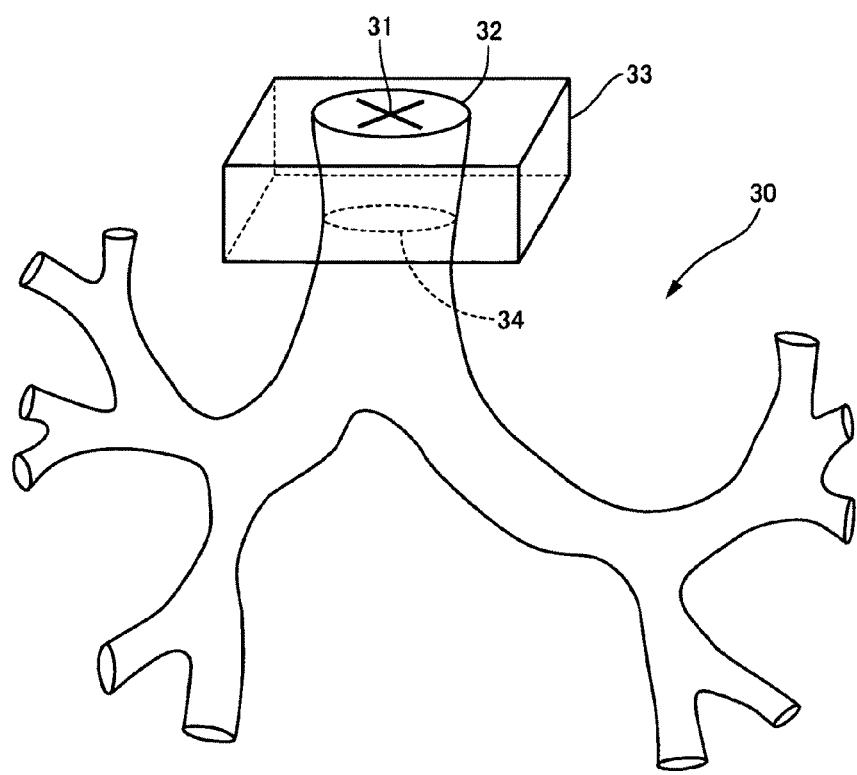
FIG. 8 is a view for explaining setting of VOI by a VOI setting portion.

In S4 corresponding to the VOI setting section 12g of the information extracting portion 12, a VOI 33 having on its upper surface a cross sectional surface 32 including the start point 31 is set as indicated in FIG. 8. The size of the upper surface of the VOI 33 is set on the basis of a radius of the cross sectional surface 32. Where the cross sectional surface 32 has a radius r, the upper surface of the VOI 33 is a square of 5r×5r.

Figure 9:
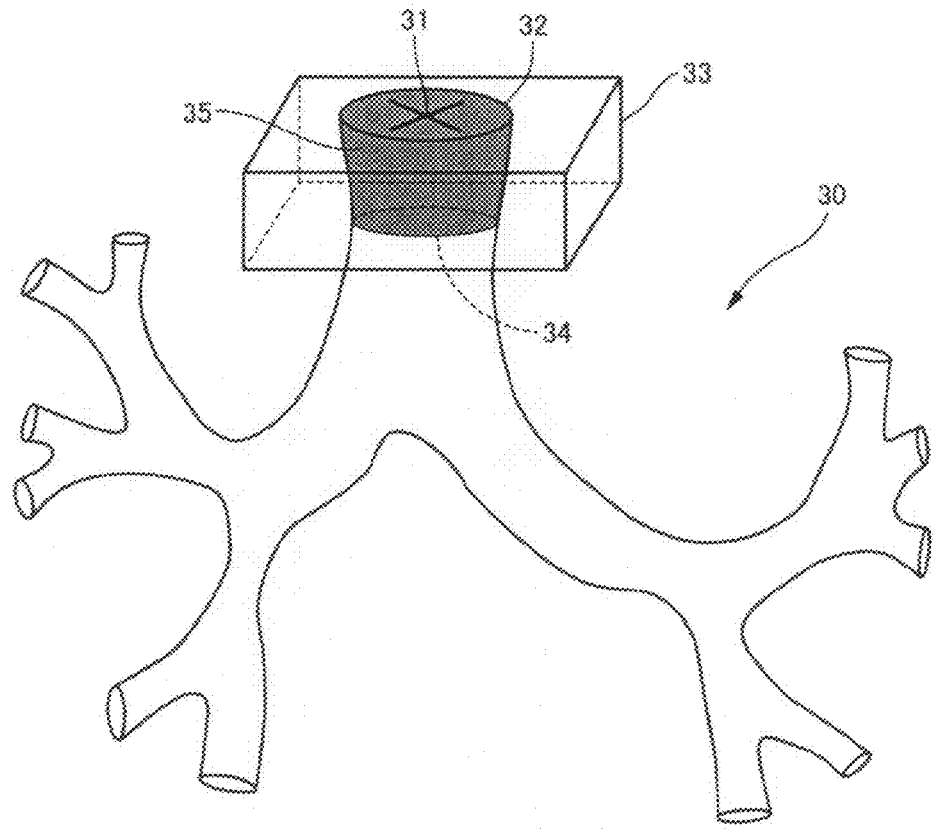
FIG. 9 is a view for explaining extraction of organ region information by an organ region information extracting section.

In S5 corresponding to the organ region information extracting section 12a of the information extracting portion 12, organ region information 35 of the VOI 33 (including inner wall information and outer wall information of the luminal organ) is extracted as indicated in FIG. 9. At this time, an image processing method is changed on the basis of the anatomical structure information stored in the anatomical information DB 13. For example, the image processing method may be selected from among the following methods:

Threshold-value processing method

Sharpening processing and threshold-value processing method

Averaging processing and threshold-value processing method

Differential-filter processing and threshold-value processing method

Hessian filter processing and threshold-value processing method

The selection of the image processing method includes selection of optimum parameters used for the processing operation.

Figure 10:
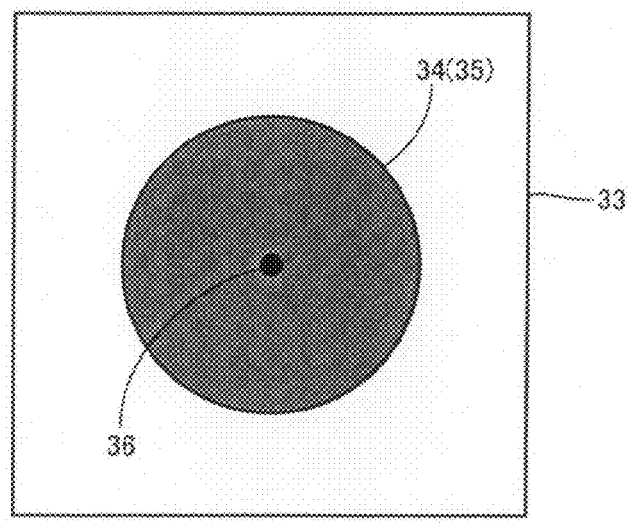
FIG. 10 is a view for explaining extraction of the organ region information in lower cross section of the VOI.

S5 is further formulated to extract also the organ region information 35 on a lower cross sectional surface 34 of the bronchi 30 corresponding to the lower surface of the VOI 33. Described in detail, a center of gravity 36 of the organ region information 34 on the lower cross sectional surface 34 is calculated as shown in FIG. 10.

Figure 11:
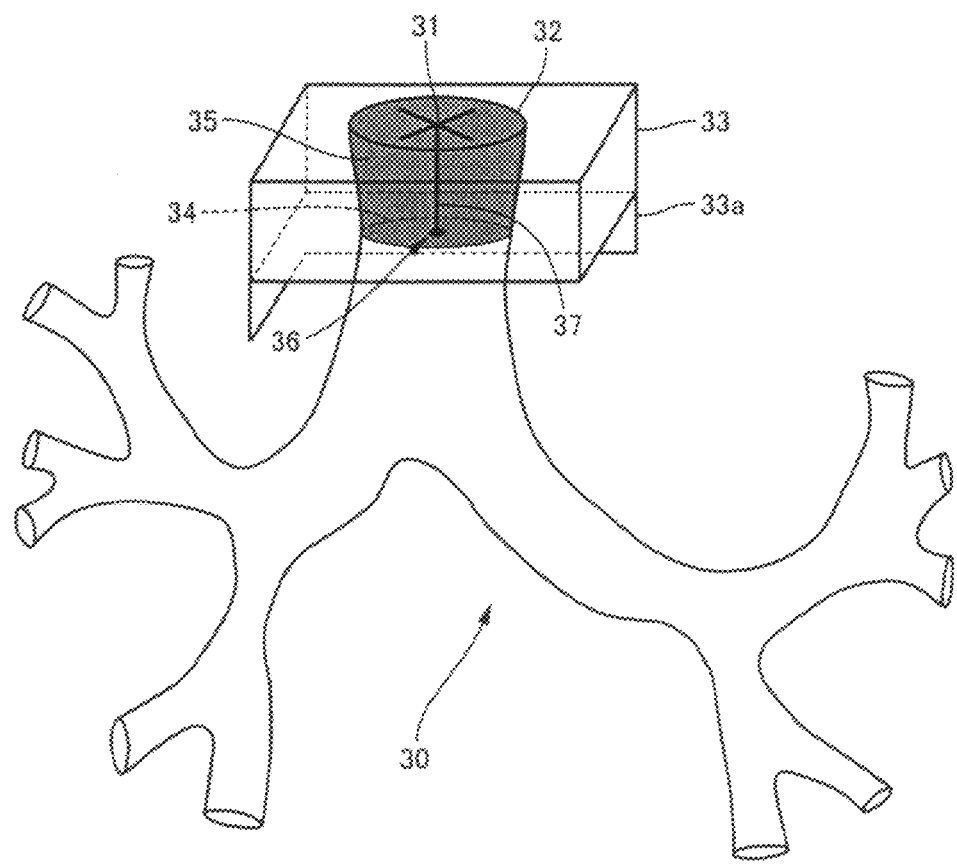
FIG. 11 is a view for explaining extraction of organ structure information by an organ structure information extracting section.

The control flow then goes to S6 corresponding to the organ structure information extracting section 12b of the information extracting portion 12, to extract, as organ structure information 37, a segment connecting the center of gravity 36 and start point 32 calculated by the organ region information extracting portion 12a, as indicated in FIG. 11.

Then, the control flow goes to S7 corresponding to the extracted information correlating section 12e of the information extracting portion 18, in which the organ region information 35 calculated in S5 and the organ structure information 37 extracted in S6 are stored in the extracted information storing section 12f, in relation to the items of anatomical information (1)-(6) stored in the anatomical information DB 13. Thus, the organ region information 35 and organ structure information 37 are correlated with the anatomical information item (1) consisting of the average value information and dispersion information regarding the direction of the branch number [n], so that the start point 32, that is, the branch of the bronchi 30 to which the VOI 33 belongs is specified.

In S7, only the items of anatomical information (1)-(6) on the specified branches are retained in the extracted information storing section 12f, and the items of anatomical information (1)-(6) on the other branches are erased from the extracted information storing section 12f.

Then, S8 corresponding to the information extracting portion 18 is implemented to determine whether the information extraction in S2 through S7 is completed for all regions of the bronchi 30. Described in detail, a determination is initially made as to whether the organ region information 35 regarding the lower cross sectional surface 34 of the bronchi 30 on the lower surface of the VOI 33 has been obtained. If a negative determination is obtained, this indicates that the lower surface of the VOI 33 has reached an end of the bronchi 30, that is, the information extraction is completed for all regions of the bronchi 30.

If it is determined in S8 that the information extraction is not completed for all regions of the bronchi 30, the control flow goes to S9 corresponding to the information extracting portion 18, to determine whether the VOI 33 has reached any bifurcation or branching point of the bronchi 30. For example, an affirmative determination that the VOI 33 has reached any bifurcation is obtained in S8 if a plurality of sets of organ region information 35 have been detected regarding the lower cross sectional surface 34 on the lower surface of the VOI 33.

Figure 12:
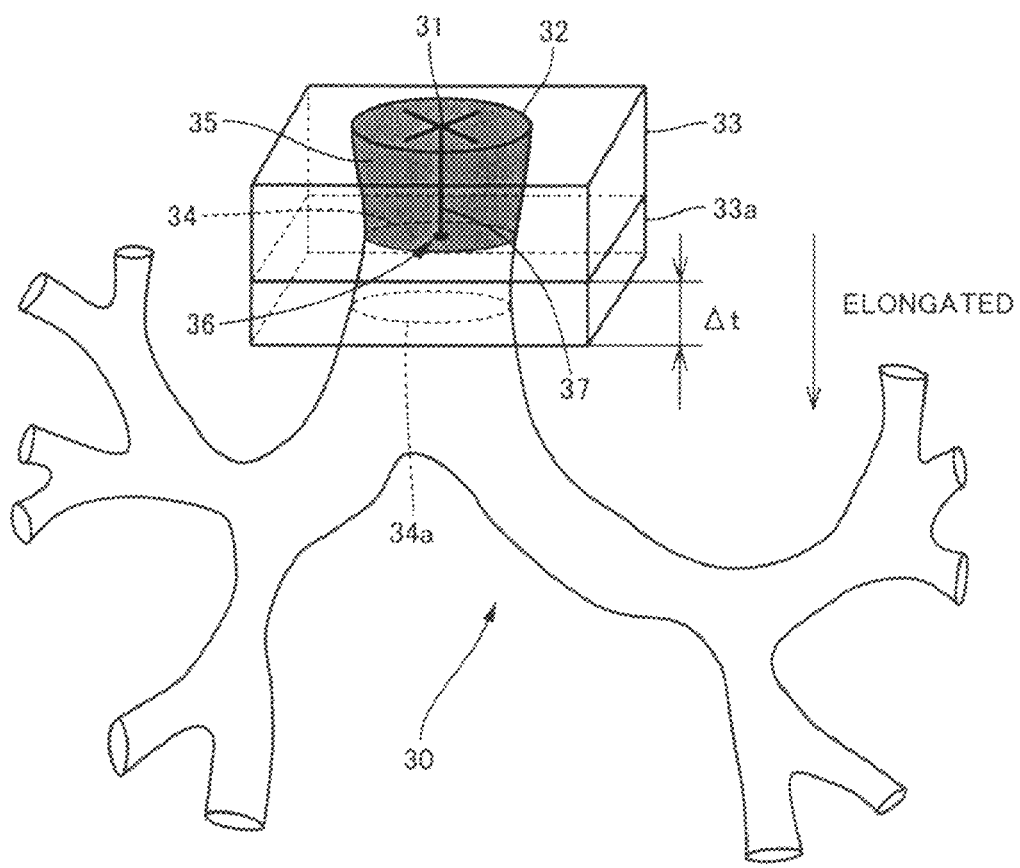
FIG. 12 is a view for explaining elongation of the VOI by the information extracting portion.

If a negative determination that the VOI 33 has not reached any bifurcation is obtained in S8, the control flow goes to S10 corresponding to the information extracting portion 12, in which the lower surface of the VOI 33 is moved by a predetermined distance Δt to elongate the VOI 33 as indicated in FIG. 12. The control flow then goes to S11 corresponding to the information extracting portion 12, to correct the direction of movement of the VOI 33 as needed, and goes back to S5 and the subsequent steps. The correction of the direction of movement of the VOI 33 will be described later.

Figure 13:
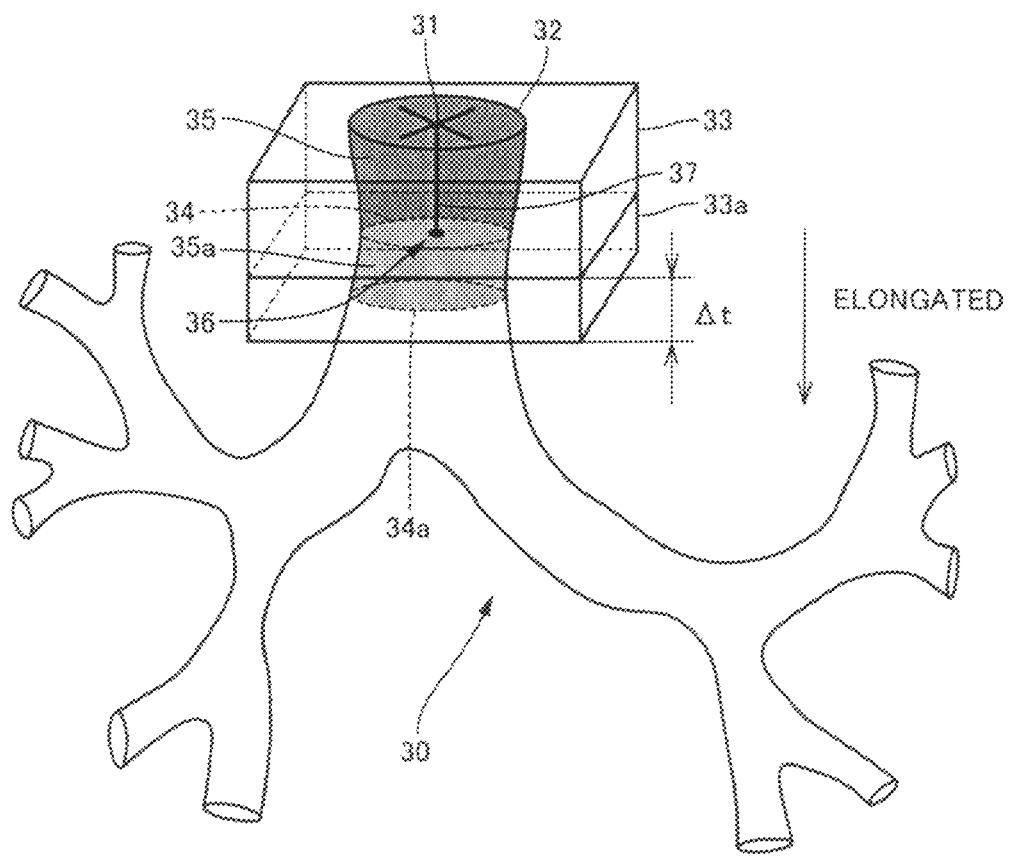
FIG. 13 is a view for explaining extraction of the organ region information with respect to the elongated VOI.
Figure 14:
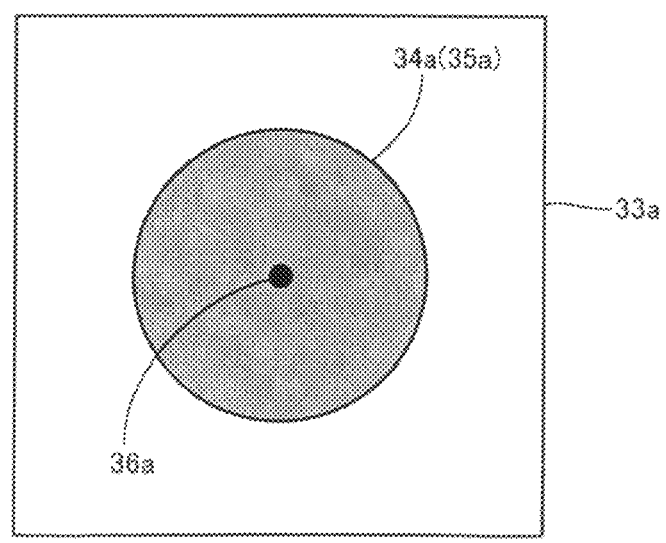
FIG. 14 is a view for explaining extraction of the organ region information in the lower cross section of the elongated VOI.
Figure 15:
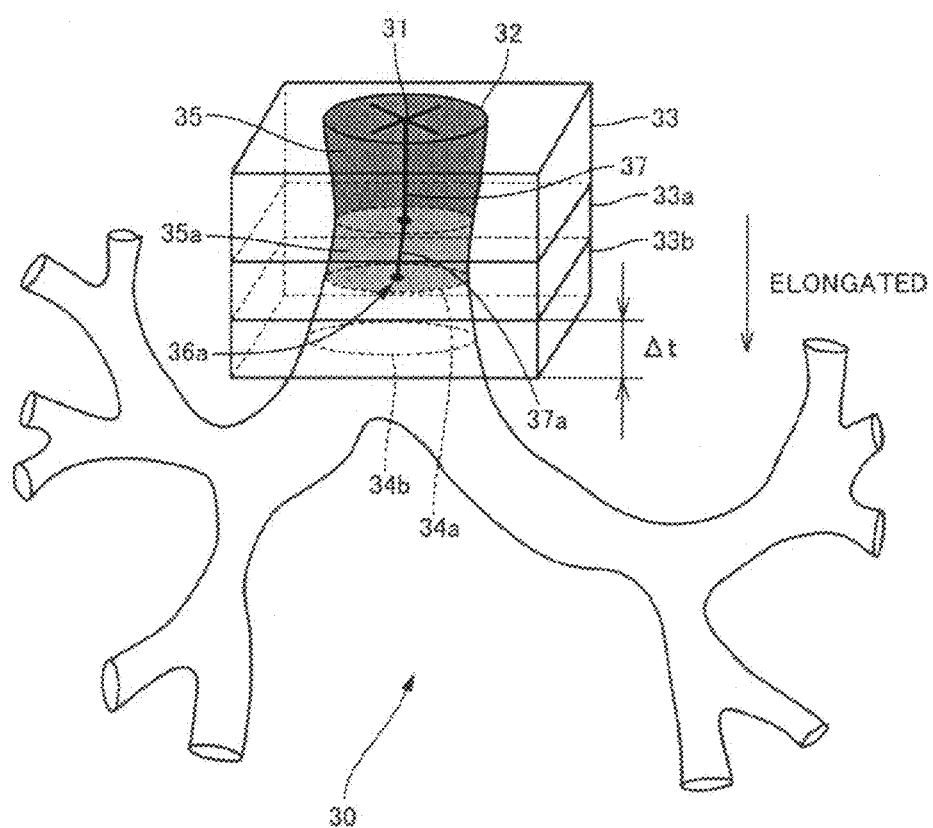
FIG. 15 is a view corresponding to that of FIG. 12, explaining further elongation of the VOI by the information extracting portion.
Figure 16:
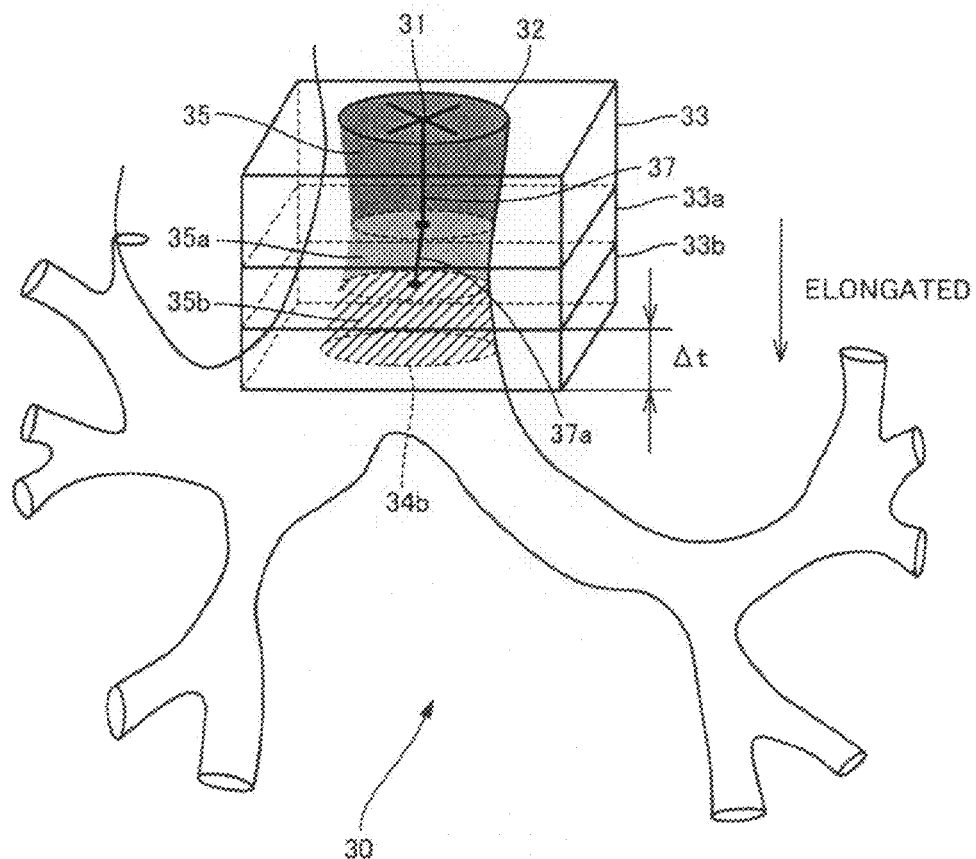
FIG. 16 is a view corresponding to that of FIG. 13, explaining extraction of the organ region information with respect to the further elongated VOI.
Figure 17:
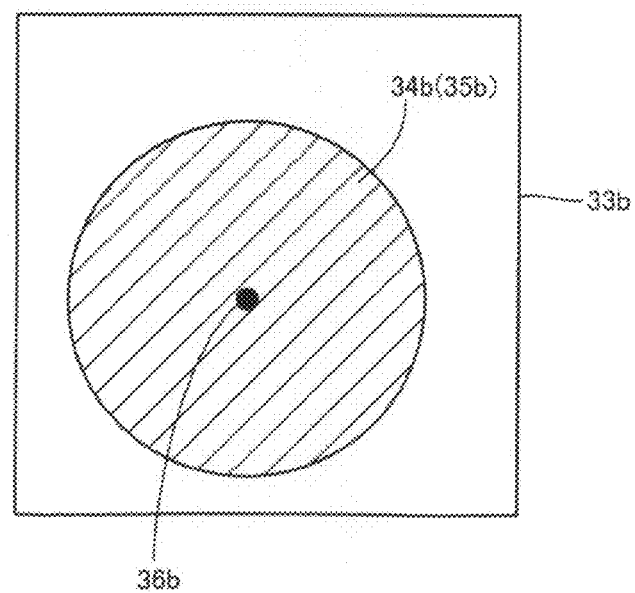
FIG. 17 is a view corresponding to that of FIG. 14, explaining extraction of the organ region information in the lower cross section of the further elongated VOI.
Figure 18:
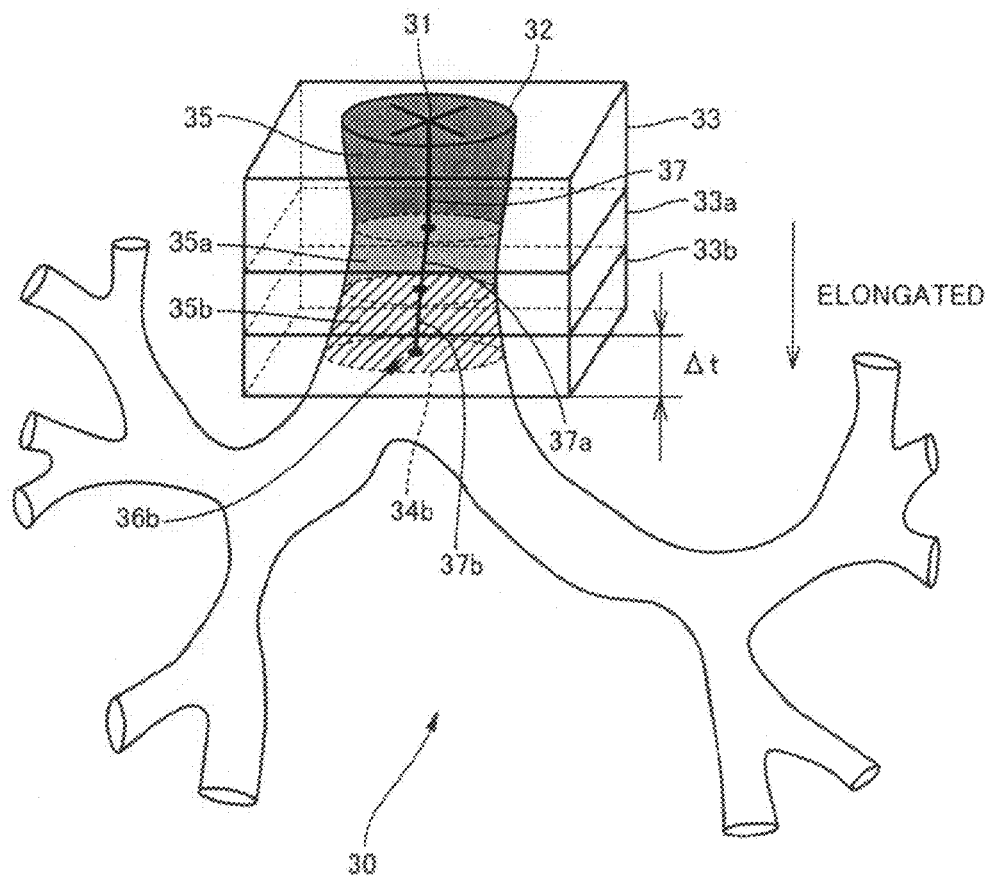
FIG. 18 is a view corresponding to that of FIG. 11, explaining extraction of the organ structure information with respect to the further elongated VOI.

In S5 corresponding to the organ region information extracting section 12a of the information extracting portion 12, organ region information 35a within the VOI 33a elongated by the predetermined distance Δt is extracted, as indicated in FIG. 13. In S5, too, the organ region information 35a on the lower cross sectional surface 34 of the bronchi 30 corresponding to the lower surface of the elongated VOI 33a is also extracted, and the center of gravity 36a of the organ region information 35a on the lower cross sectional surface 34a is calculated, as indicated in FIG. 14.

The control flow then goes to S6 in which a segment connecting the center of gravity 36 and the center of gravity 36a is extracted as organ structure information 37a. In S7, the organ region information 35a calculated in S5 and the organ structure information 37a extracted in S6 are stored in the extracted information storing section 12f, in relation to the items of anatomical information (1)-(6) of the anatomical information DB 13.

In the state of FIG. 13, all regions have not been extracted, and the VOI 33a have not reached any bifurcation, so that the control flow goes to S10 and S11 through S8 and S9, and goes back to S5. FIGS. 15-18 indicate the extraction of organ region information 35b and organ structure information 37b of the VOI 33b which is further elongated by the predetermined distance Δt by moving the lower surface of the VOI 33a. Reference sign 36b in FIGS. 15-18 denotes the center of gravity of the organ region information 35b on the lower cross sectional surface 34b of the VOI 33b.

Figure 19:
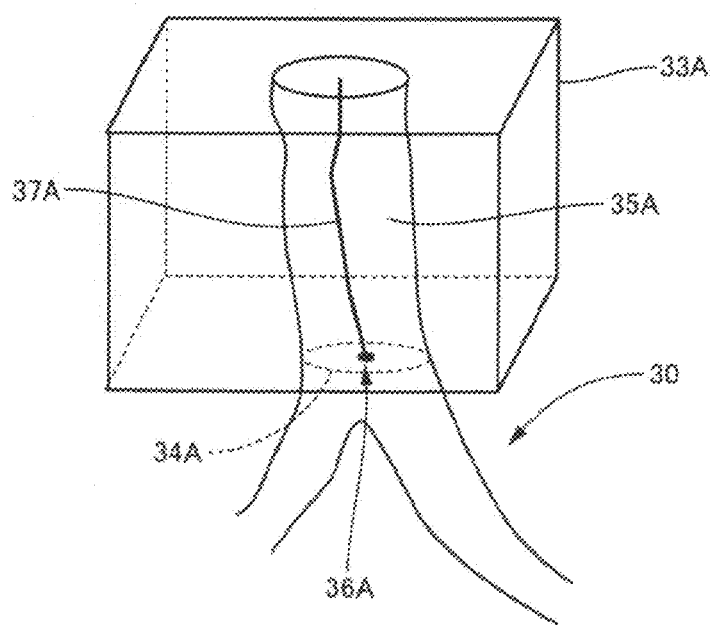
FIG. 19 is a view indicating shifting of the VOI with respect to the luminal organ.
Figure 20:
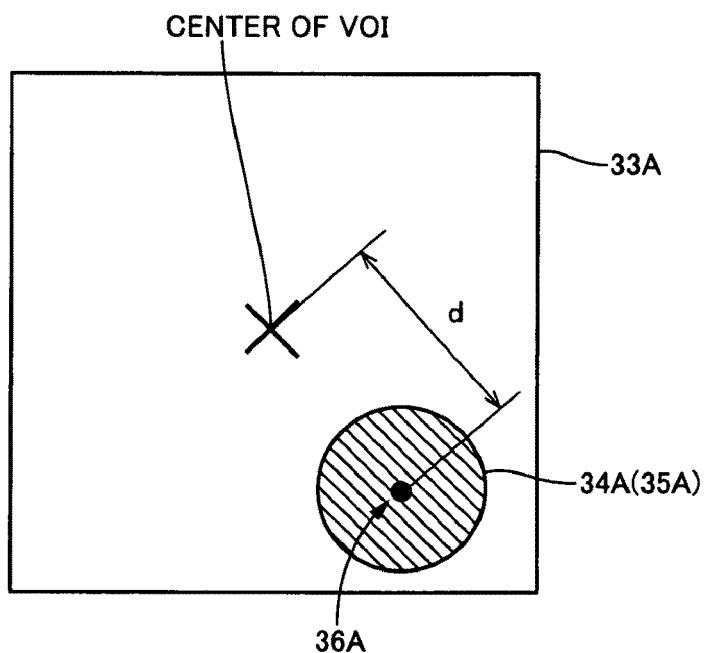
FIG. 20 is a bottom plan view indicating the shifting of the VOI with respect to the luminal organ.

Thus, S5-S11 are repeatedly implemented, and the VOI 33 is further elongated. When a VOI 33A is obtained by elongation by a certain total distance, as indicated in FIG. 19 by way of example, the center of gravity 36A of the organ region information 35A on the lower cross sectional surface 34A at the lower end of the segment which extends from the start point and which corresponds to the organ structure information 37a within the VOI 33A may be offset with respect to the center of the lower cross sectional surface 34A of the VOI 33A. When an offset distance "d" of the center of gravity 36A from the center of the center of the VOI 33A has exceeded a predetermined threshold value ϵ, as indicated in FIG. 20 by way of example, the direction of movement of the VOI 33 is corrected in the above-described step S11.

Figure 21:
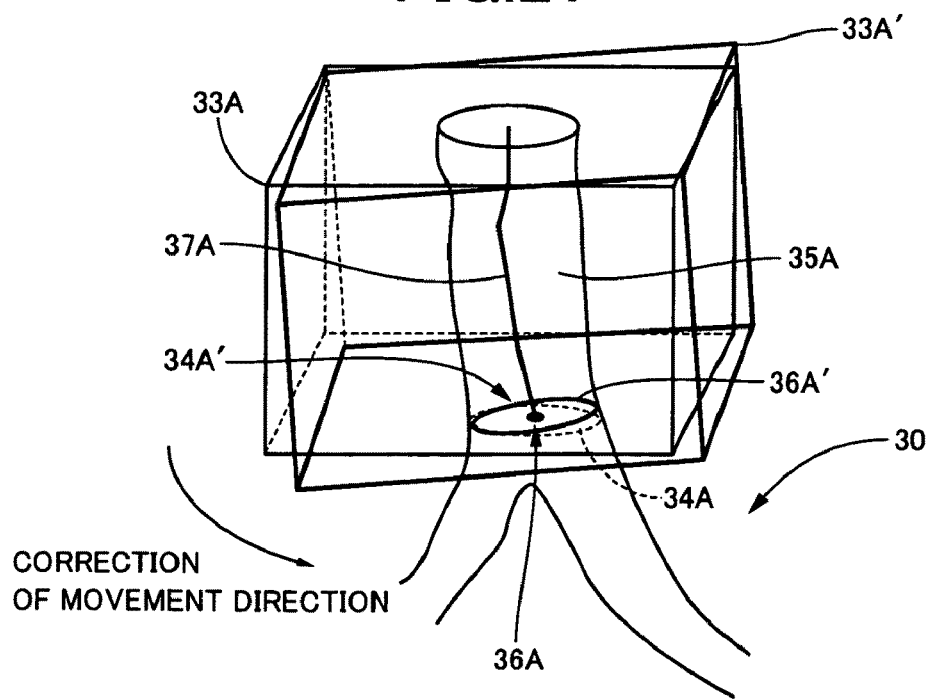
FIG. 21 is a view for explaining a direction correcting operation of the VOI.
Figure 22:
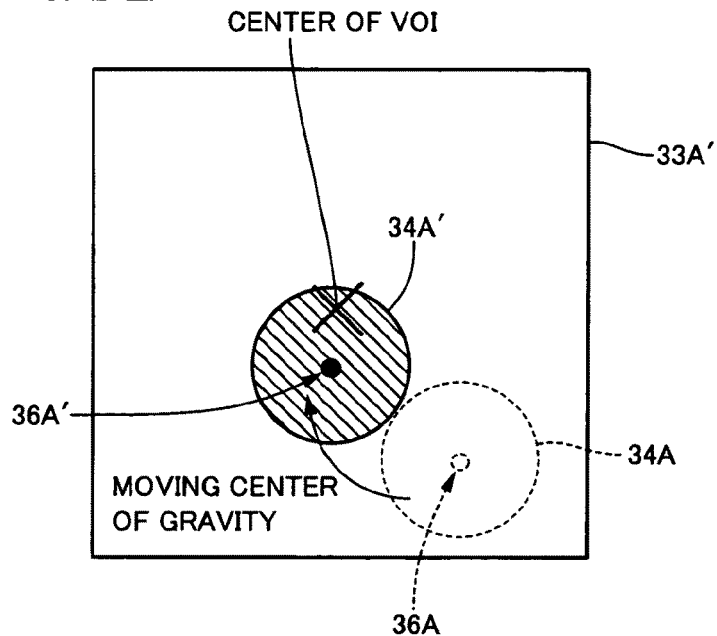
FIG. 22 is a view for explaining a direction correcting operation of the VOI.

Described more specifically, S11 corresponding to the VOI setting section 12g is formulated such that when the offset distance "d" has exceeded the predetermined threshold value ϵ, the direction of movement of the VOI 33A is corrected so as to move the center of gravity 36A to come closer to the center of the VOI 33A while the appropriate part of the bronchi 30 is kept enveloped within the thus moved VOI 33A', as indicated in FIG. 21. In this manner, the center of gravity of the organ region information 35A' on the lower cross sectional surface 34A' is located close to the center of the VOI 33A', so that at least a part of the bronchi 30 near the lower cross sectional surface 34A' is prevented from being located outside the VOI 33A.

Figure 23:
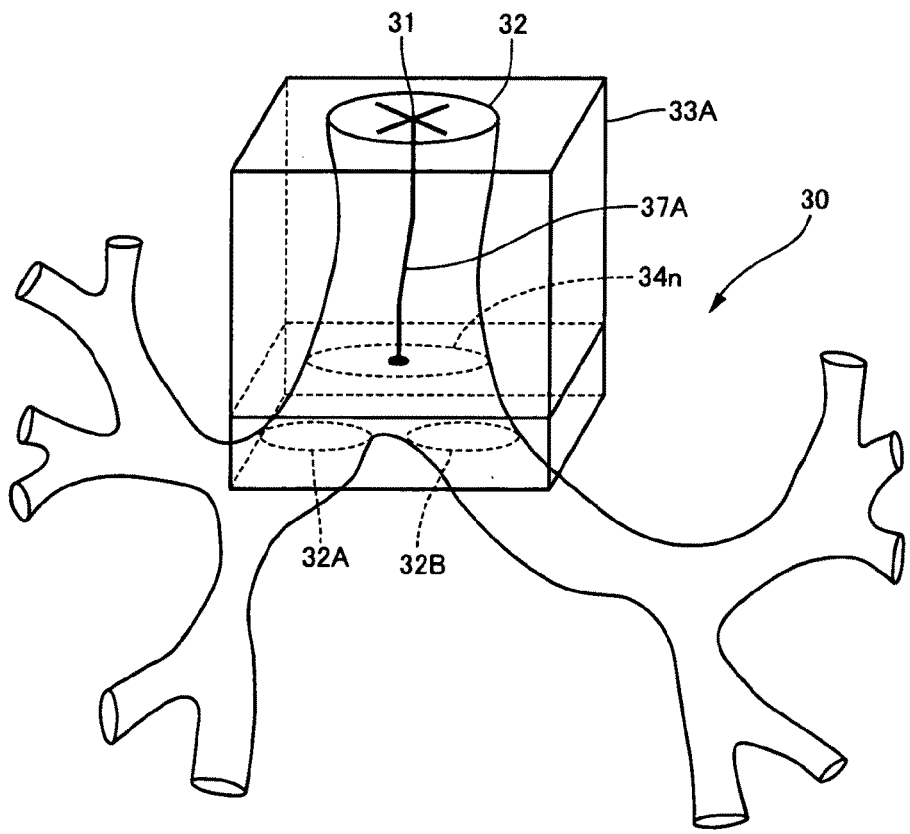
FIG. 23 is a view showing an example of a VOI when a bifurcation of the luminal organ is detected.
Figure 24:
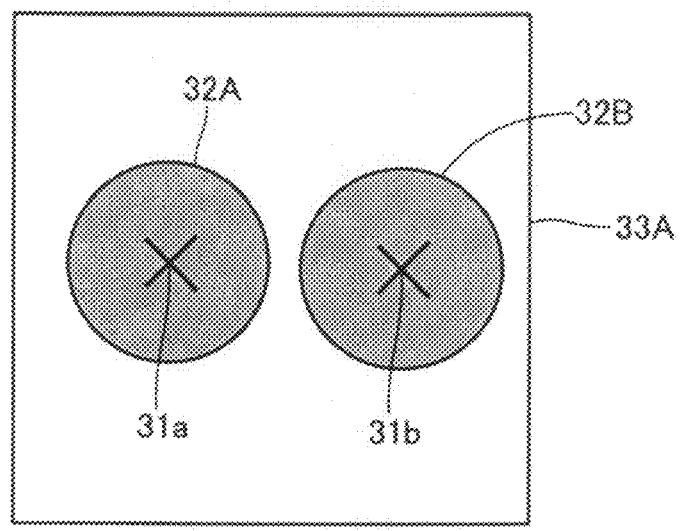
FIG. 24 is a view showing an example of a VOI when a bifurcation of the luminal organ is detected.

Then, there will be described an operation to be performed when it is determined in S8 that the VOI 33A has reached any bifurcation or branching point. When the VOI 33A has the lower cross sectional surface 34n as indicated in FIG. 23 as a result of elongation of the VOI 33A, the VOI 33A has not reached a bifurcation. When the VOI 33A is further elongated by the predetermined distance Δt from the position of the lower cross sectional surface 34n, two branch cross sectional surfaces 32A and 32B are extracted in S9, on the lower cross sectional surface of the VOI 33A, as indicated in FIG. 24. In this case, it is determined that the VOI 33A has reached a bifurcation, and the control flow goes to S12.

In S12 corresponding to the organ region information extracting section 12a, centers of gravity 31a, 31b of the organ region information on the two branch cross sectional surfaces 32A, 32B are calculated. These centers of gravity 31a and 31b are respectively set as start points of child VOI 33(1)a and VOI 33(1)b connected to the parent VOI 33A. Then, the control flow goes back to S2 and the subsequent steps.

In this case, the items of anatomical information (1)-(6) of branches of the bronchi 30 enveloped within the child VOI 33(1)a and 33(1)b connected to the parent VOI 33A are extracted in S2. In S3, the items of anatomical information (1)-(6) of the branches thus extracted in S2 are stored in the extracted information storing section 12f, and correlation of anatomical nomenclature is implemented. Described in detail, one of the bronchial branches stored in the anatomical information DB 13, which is most similar to the child VOIs 33(1)a, 33(1)b, is selected on the basis of the directions of extension and lengths of the child VOIs calculated from the organ structure data obtained by the information extracting portion 12, and on the basis of the anatomical information of the parent branch and any preceding branches. The thus selected branch is correlated with the appropriate anatomical nomenclature. The sizes of the upper surfaces of the child VOI 33(1)b and VOI 33(1)b are set on the basis of the radii of the branch cross sectional surfaces 32A, 32B.

Figure 25:
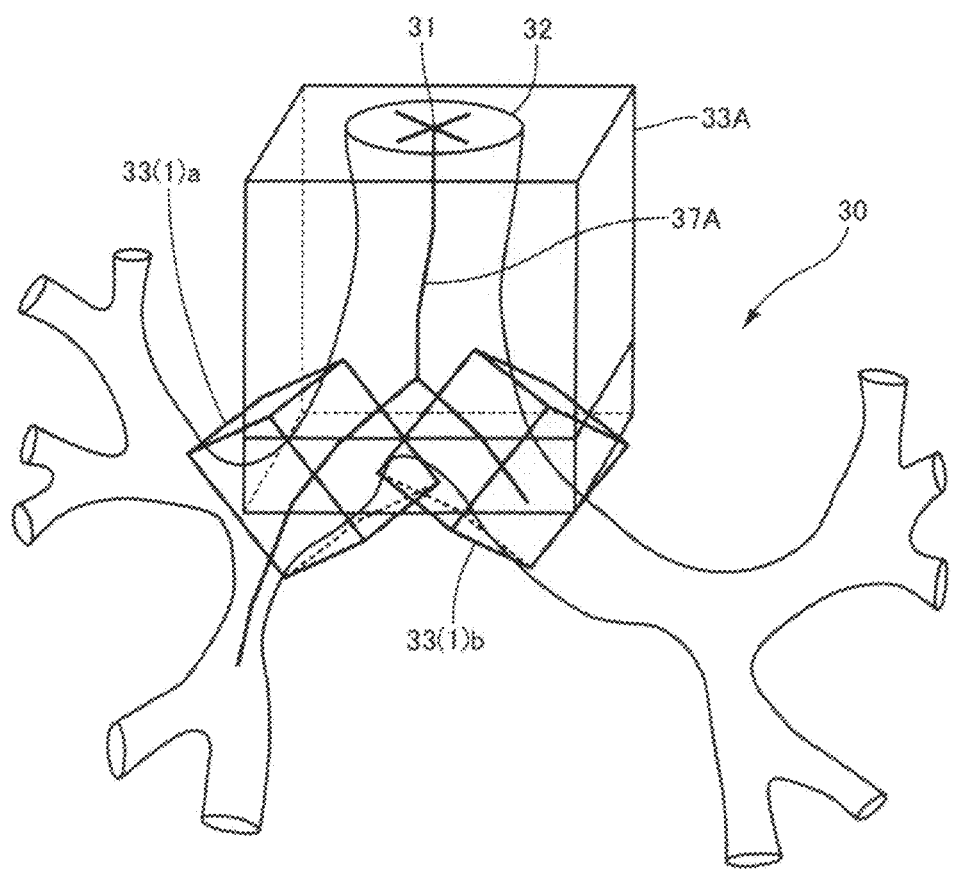
FIG. 25 is a view for explaining setting of child VOIs by a VOI setting section.

In S4 corresponding to the VOI setting section 12g of the information extracting portion 12, the two child VOIs 33(1)a, 22(1)b having on their upper surfaces respective cross sectional surfaces 32a, 32b including respective start points 31a, 31b are set, as indicated in FIG. 25. The size of the upper surface of each child VOI 33(1)a, 33(1)b is set on the basis of the radius of the corresponding cross sectional surface 32a, 32b. The control flow then goes to S5 to calculate the organ region information, and to S6 to extract the organ structure information. The extracted organ structure information is stored in the extracted information storing section 12f, as segments connected to the segment which corresponds to the organ structure information 37A obtained prior to the setting of the child VOIs 33(1)a, 33(1)b and which extends from the start point 31 to the center of gravity of the lower cross sectional surface 34n of the VOI 33A. Namely, the segments represented by the organ structure information of the child VOIs 33(1)a, 33(1)b obtained upon the present execution of S6 connect the center of gravity of the lower cross sectional surface 34n to the centers of gravity of the cross sectional surfaces 32A, 32B at the upper ends of the child VOIs 33(1)a, 33(1)b.

Figure 26:
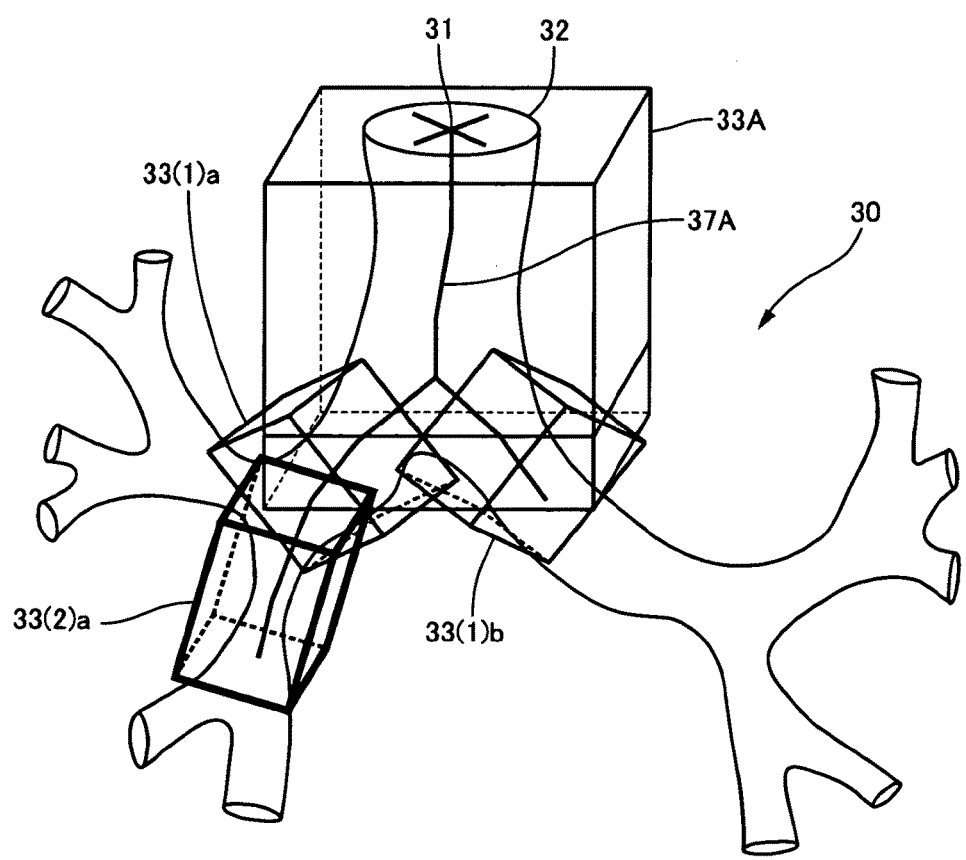
FIG. 26 is a view for explaining setting of grandchild VOIs by the VOI setting portion.

S5 through S11 are repeatedly implemented for the thus set child VOI 33(1)a and VOI 33(1)b, to incrementally elongate the child VOIs 33(1)a, 33(1)b. When one of the two child VOIs, for instance, the child VOI 33(1)a, has reached any bifurcation or branching point, the affirmative determination is obtained in S9, and the control flow goes to S12 and the subsequent steps, as described above. As a result, a grand child VOI 33(2)a connected to the child VOI 33(1)a is set, as indicated in FIG. 26.

If it is determined in step S8 corresponding to the information extracting portion 12 that extraction of all of the organ regions is completed, the processing operation according to the present flow chart is terminated.

Figure 27:
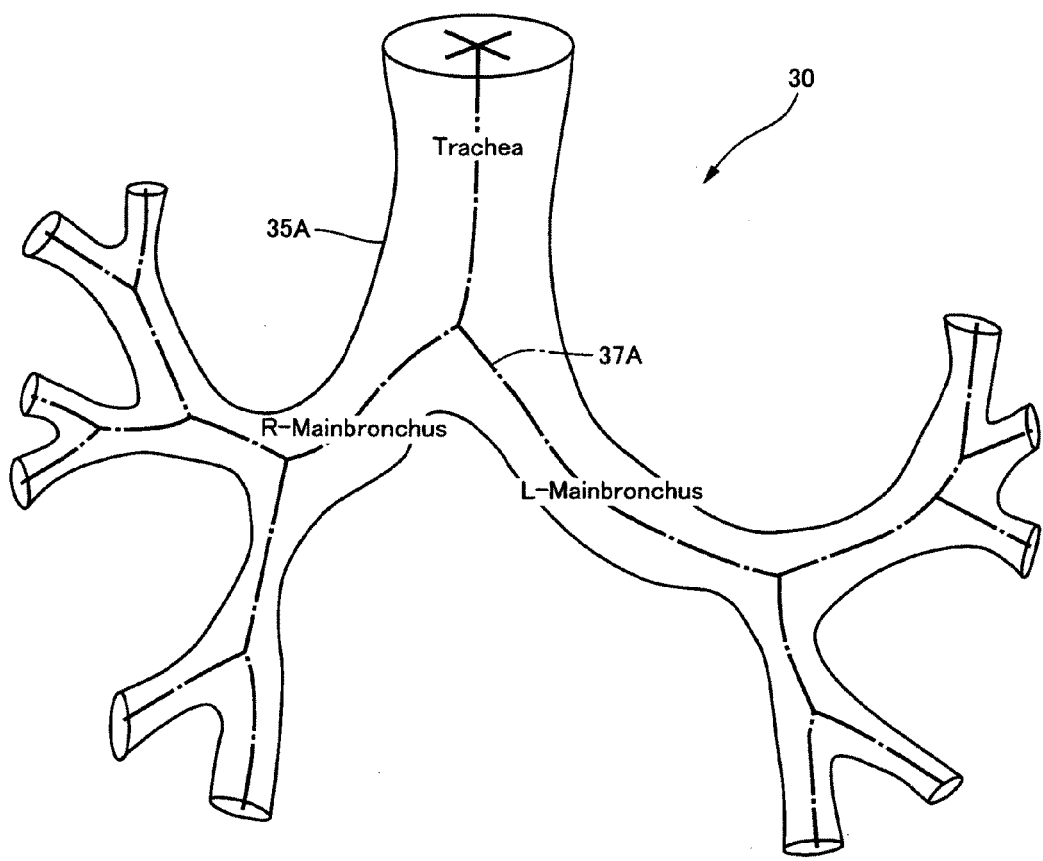
FIG. 27 is a view showing an example of generated organ structure information.
Figure 28:
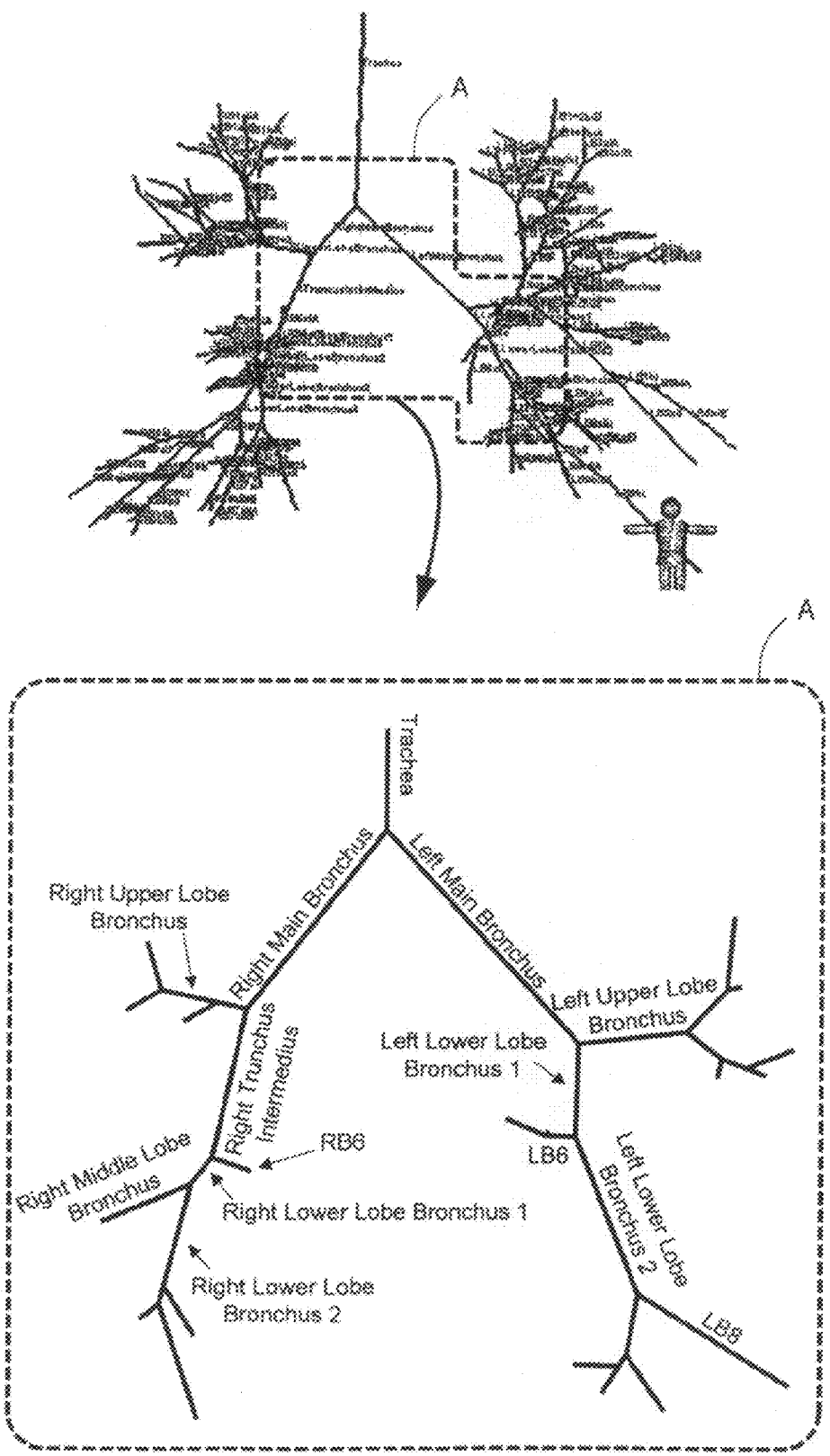
FIG. 28 is a view showing an example of the organ structure information displayed on display means.

According to the processing operation described above, the information extracting portion 12 stores the organ structure information 37A corresponding to each of all branches of the bronchi 30, in the extracted information storing section 12f, as indicated in FIG. 27. FIG. 27 schematically shows a result of the above-described processing operation. The extracted information storing section 12f stores the organ structure information 37A, in relation to the corresponding organ region information 35A and the anatomical nomenclature of the corresponding branch. FIG. 28 shows an example of images actually displayed on the monitor 2, which image represents the organ structure information 37A correlated with the anatomical nomenclature of the branches generated by the anatomical nomenclature information generating portion 16. The anatomical nomenclature of each branch is represented by character image data generated by the anatomical nomenclature information generating portion 16 on the basis of the nomenclature assigning information received from the information extracting portion 12, and is superimposed on the organ region information 35A and organ structure information 37A, or on virtual external profile image data of the luminal organ generated based on the organ region information 35A and organ structure information 37A. An upper one of the two images in FIG. 28 indicates this anatomical nomenclature displayed on the monitor 2, while a lower one of the two images which is enclosed by a square indicated by broken line is an enlarged view of a part of the upper image enclosed by the corresponding square.

Figure 29:
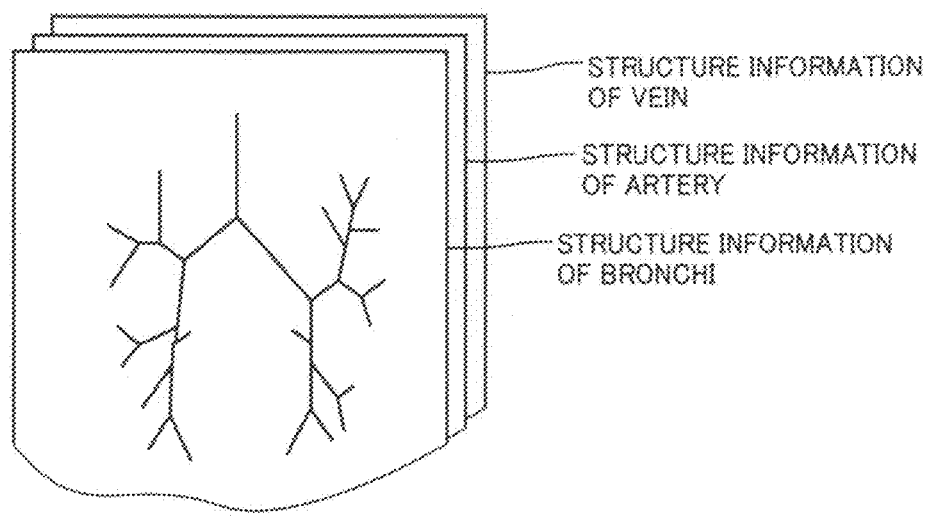
FIG. 29 is a view for explaining a concept of correlating a plurality of sets of structure information of the luminal organ.

As previously described, the luminal organs include not only the bronchi 30, but also esophagus, blood vessels, large intestine, small intestine, intestinum duodenum, stomach, bile duct, pancreatic duct proper, lymphatic duct, etc. The extracted information storing section 12f stores the structure information of the bronchi, structure information of artery and structure information of vein, in relation to the nomenclature of the branches, as indicated in FIG. 29.

Figure 30:
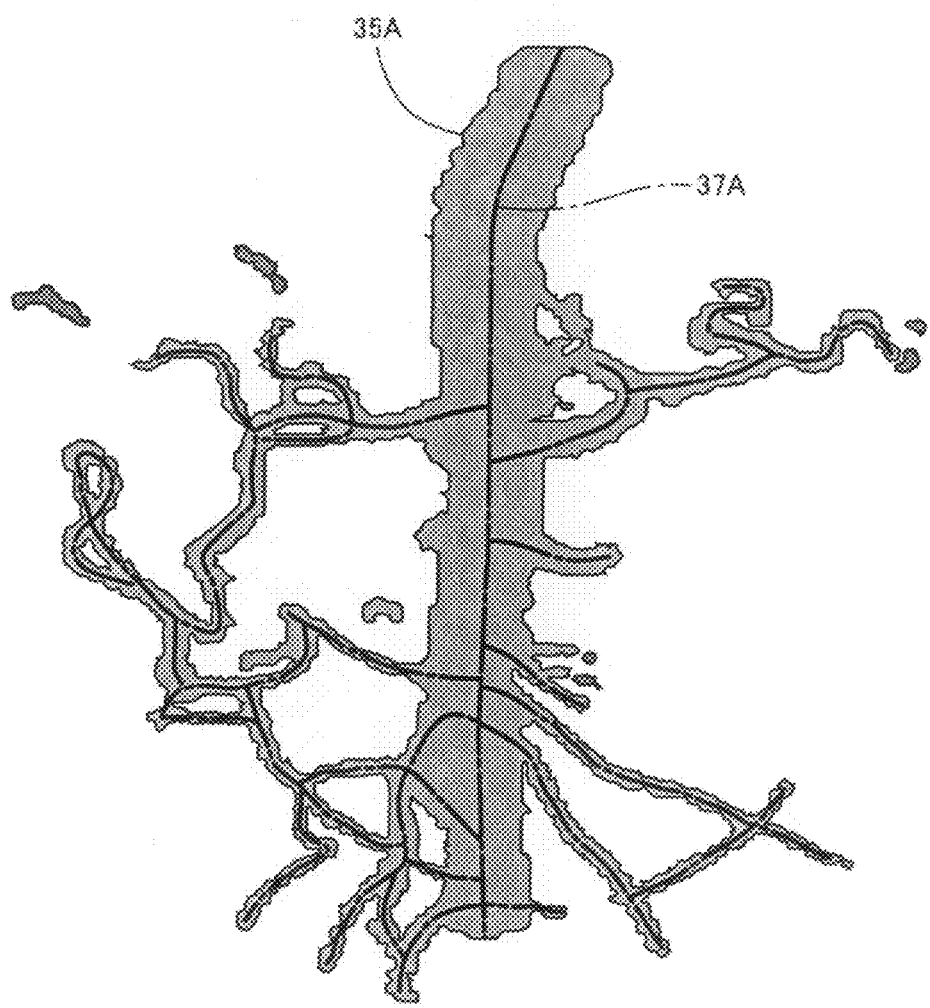
FIG. 30 is a view showing a three-dimensional image of artery and structure information of the artery superimposed on each other.
Figure 31:
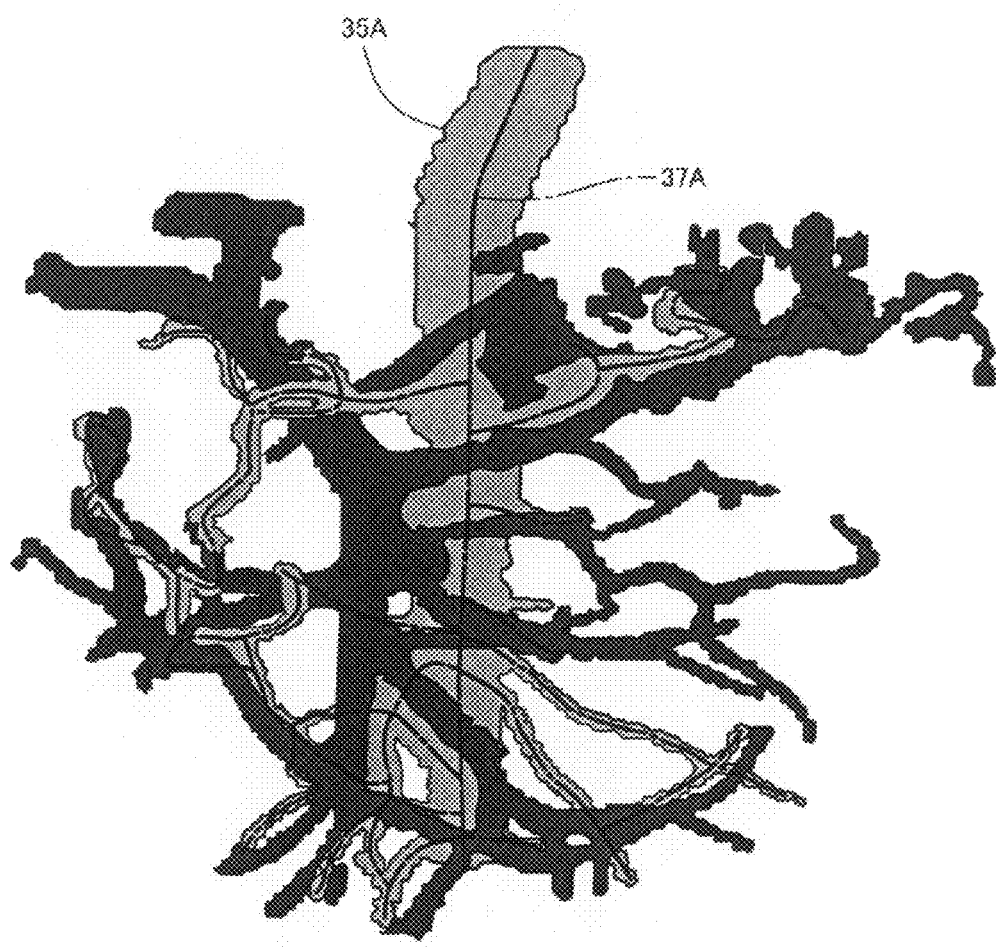
FIG. 31 is a showing a three-dimensional image of vein superimposed on the three-dimensional image of the artery and the structure information of the artery.

FIG. 30 shows the structure information of the artery and a three-dimensional image of the artery which are superimposed on each other, while FIG. 31 shows a three-dimensional image of the vein superimposed on the superimposed structure information and three-dimensional image of the artery of FIG. 30. These structure information and three-dimensional images are those displayed on the monitor 2. Like the items of information of the bronchi, the items of information of the artery, for example, can be extracted.

Referring to the flow chart of FIG. 32, there will be described an observation assisting operation of the medical image observation assisting system 1, for imaging diagnosis, laparotomy or abdominal incision, surgical operation under endoscopic observation, or preparation for the surgical operation under endoscopic observation, using the extracted organ region information, organ structure information and branch nomenclature, in connection with the artery.

Prior to initiation of the observation assisting operation, the luminal organ image generating portion 15 generates an external profile image 50 of the luminal organ as indicated in FIG. 33, on the basis of the organ region information and organ structure information received from the information extracting portion 12, and the CT image data received from the CT-image-data storing portion 11. The generated external profile image 50 is displayed on the monitor 2, together with a pointer 51.

The observation assisting operation of the flow chart of FIG. 32 is initiated with S21 corresponding to the user I/F control portion 19, in which selection of a start point by an operation of the input portion 3 in the form of a mouse, for example, to move the pointer 51 is detected The direction of movement of the pointer in response to the operation of the input portion 3 is controlled on the basis of the organ region information and organ structure information. Described in detail, sensitivity of movement of the pointer in a direction intersecting a virtual centerline, and sensitivity of movement of the pointer in the virtual centerline are set such that the sensitivity of movement in the virtual centerline is higher than that in the direction intersecting the virtual centerline. When the pointer has been moved into the luminal organ in the external profile image of the organ, for example, the pointer cannot be moved out of the organ unless the pointer is moved by a large distance, but can be easily moved in the direction of extension of the organ. Thus, the observer feels that the pointer tends to move on the luminal organ, and can easily select a point on the organ as the start point.

In S22 corresponding to the user I/F control portion 19, input information through the input portion 3 is controlled. Described in detail, an operation of a left pushbutton 3L of the mouse of the input portion 3 shown in FIG. 34 causes the external profile image 50 of the luminal organ to be moved downwards, while an operation of a right pushbutton 3L of the mouse causes the external profile image 50 to be moved upwards.

Figure 35:
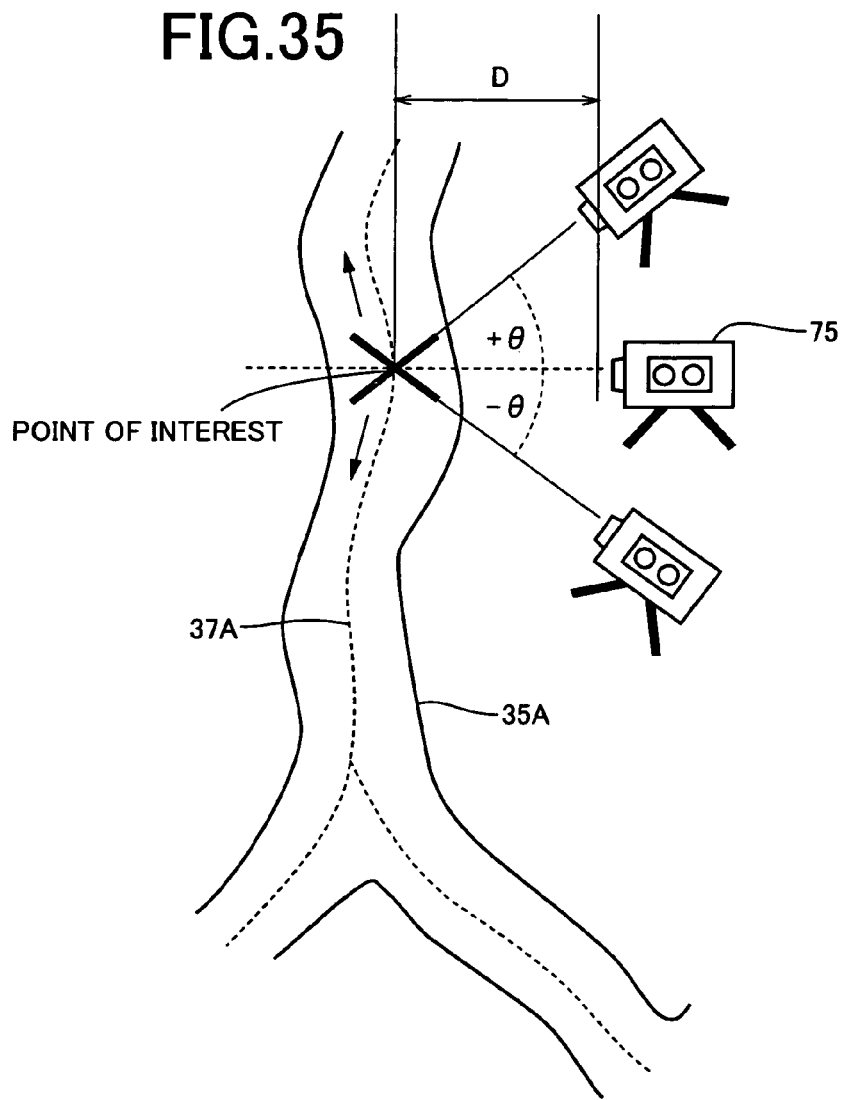
FIG. 35 is a view indicating an exemplary relationship among a point of interest, a point of view and a line of view.

The control flow then goes to S23 corresponding to the point of view/line of view setting portion 14, in which the branch at which the start point is located is extracted. Then, the control flow goes to S24 corresponding to the point of view/line of view setting portion 14, in which the point of view and the line of view are set for the branch extracted in S23. In S25 corresponding to the point of view and line-of-view direction setting portion 14, a point of view 75 is located at a position which is spaced apart by a predetermined distance D from a point of interest lying on the centerline of the artery represented by the organ structure information 37A, in the direction perpendicular to the centerline, as indicated in FIG. 35. The line of view can be changed in the vertical and horizontal directions within an angular range of θ with respect to a segment connecting the point of view and the point of interest.

Upon determination of the point of view 75 in S25, the distance D between the point of view 75 (observing position) and the point of interest is calculated so that the blood vessel displayed on the monitor 2 has a size desired by the observer, irrespective of its portions, and the point of view 75 is determined on the basis of the calculated distance D. Then, point-of-view information indicative of the point of view 75 and line-of-view direction information indicative of the line-of-view direction are calculated. Described in detail, the observer enters a numerical value representing a desired actual width dimension (e.g., 10 mm) of the displayed image of the blood vessel or a desired ratio (e.g., 10%) of the width dimension of the displayed blood vessel to the width dimension of the monitor screen, through a keyboard or mouse of the input portion 3. As a result, a ratio of magnification of the diameter of the blood vessel obtained from the organ region information, for instance, is automatically calculated, and the distance D is calculated. In S26 corresponding to the luminal organ image generating portion 15, the luminal organ external profile image data are generated on the basis of the point-of-view information and line-of-view direction information calculated in S25. The point-of-view information and line-of-view direction information calculated in S25 may be displayed on the monitor 2, together with the external profile image data of the luminal organ.

In S25 in which the distance D is calculated, the observer may operate the keyboard, mouse or any other input device of the input portion 3, to increase or decrease the distance D, such that the displayed external profile image of the blood vessel is enlarged or contracted as the input portion 3 is operated by the observer. For example, the mouse is moved right and left while a pointer button of the mouse is kept pressed and while a certain key (e.g., "z" key) on the keyboard is kept pressed. Thus, the user can select the magnification ratio of the external profile image of the blood vessel. In other words, S24 through S26 may be repeatedly implemented until the desired size of the external profile image is obtained.

Figure 36:
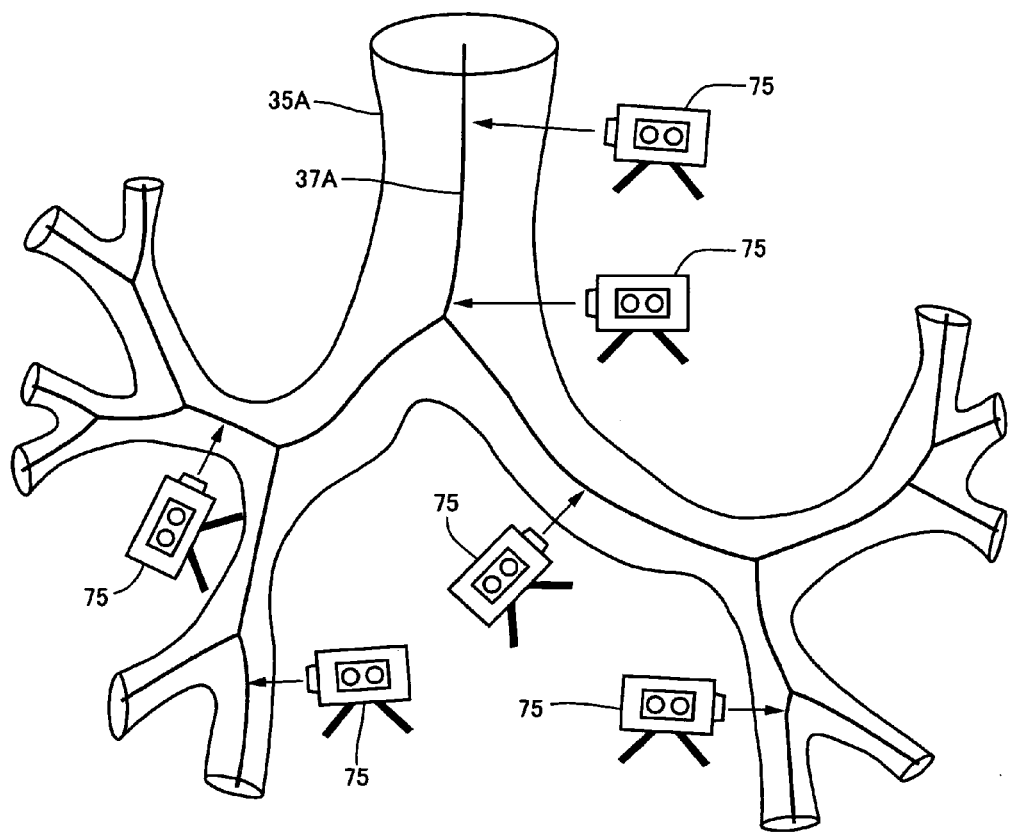
FIG. 36 is a view for explaining an example of change of the point of view.

In S27 corresponding to the luminal organ image generating portion 15, a determination is made as to whether the mouse of the input portion 3 has been operated. If the mouse has been operated, an affirmative determination is obtained in S27, and the control flow goes to S28 in which the distance D between the point of view 75 and the point of interest is changed according to the diameter of the blood vessel, in response to the detected operation of the mouse, and the observing position (point of view 75) is moved with respect to the external profile image 50, in the longitudinal direction of the blood vessel, on the basis of the organ structure information, as indicated in FIG. 36. At the new point of view thus obtained, virtual external profile data of the blood vessel is generated. Thus, a portion of the blood vessel near the point of interest is displayed with a size desired by the observer.

Figure 38:
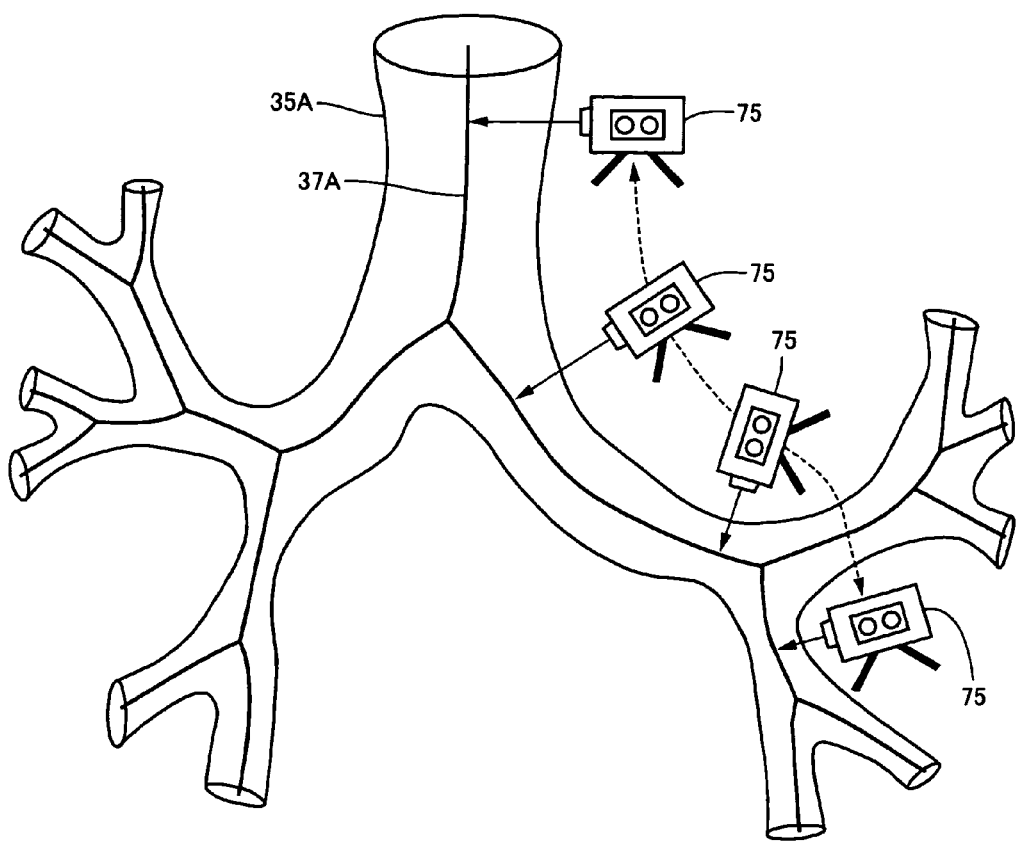
FIG. 38 is a view for explaining movements of the point of view.

The processing operations in S25 through S29 are repeatedly implemented until the operation of the mouse is detected, or until the termination of the observation assisting operation is detected in S29. FIG. 37 shows images as viewed from a plurality of points of view 75 (three points of view in this specific example), which are obtained by moving the viewing position (point of view 75) in the lock-on state, as indicated in FIG. 38. At this time, the point of interest is fixed on the centerline corresponding to the organ structure information 37A. Thus, S26 corresponding to the luminal organ image generating portion 15 is formulated to generate the virtual external profile image such that the point of interest is located at a center of the generated image.

In the prior art, the organ structure information is calculated after the organ region information is extracted, so that it is difficult to align the organ structure information with the centerline of the luminal organ. In the present embodiment, on the other hand, the information extracting portion 12 is configured to extract concurrently the organ region information and the organ structure information, so that the organ structure information can be substantially aligned with the centerline of the luminal organ. In addition, the suitable image processing method can be selected on the basis of the anatomical information for each branch of the organ stored in the anatomical information DB 13, so that the regions and structures of the individual branches of the organ can be accurately extracted.

The present embodiment is further configured to use the extracted organ structure information as the centerline of the luminal organ, and calculate the distance between the point of view and the point of interest such that the displayed blood vessel has a predetermined size irrespective of different portions of the blood vessel, and to generate and display the virtual external profile image of the luminal organ such that the center of the image is located at the point of interest. Accordingly, the luminal organ can be exactly observed with the desired size of the displayed image, without the observer having to perform a cumbersome operation to change the point of view and the line-of-view direction. Therefore, the observer can easily detect a change of the direction of extension and shape of the luminal organ, during imaging diagnosis, laparotomy or abdominal incision, surgical operation under endoscopic observation, or preparation for the surgical operation under endoscopic observation. Thus, the present Embodiment 1 of this invention facilitates external profile observation of the luminal organ.

According to the embodiment described above, the VOI setting section 12g sets the volume region enveloping a part of the luminal organ extending within the subject body, on the basis of the three-dimensional image data of the subject body, and the organ region information extracting section 12a repeatedly calculates the luminal region information 35 in the form of specific region information of the luminal organ within the volume region, on the basis the three-dimensional image data of the luminal organ within the volume region, while the organ structure information calculating section 12b calculates the luminal structure information 37 in the form of structure information of the luminal organ within the volume region, for each set of the luminal region information. The organ structure information calculating section 12b functioning as the virtual-centerline generating means generates the virtual centerline extending in the longitudinal direction of the luminal organ, on the basis of the luminal structure information 37 and the luminal organ image generating portion 15 generates the virtual image of the luminal organ along the virtual centerline. The point of view/line of view setting portion 14 determines the observing position for generating the virtual image, on the basis of at least one of the virtual centerline, the luminal region information 35 and the luminal structure information 37, such that the region of the luminal organ displayed on the monitor 2 has a desired size, and moves the observing position in the longitudinal direction of the luminal organ, on the basis of the virtual centerline or the luminal structure data, and the display means displays the virtual image. Accordingly, the virtual image of the luminal organ reflecting the structure information can be obtained from the three-dimensional image data. Further, the structure of the luminal organ can be exactly observed from the desired point of view of the organ, without a cumbersome operation to change the point of view. In addition, the observing position is calculated such that the region of the luminal organ displayed on the display means has a desired size, and the ratio of magnification of the external profile image of the luminal organ displayed on the display means is automatically adjusted, so that the observer can easily observe the luminal organ along its direction of extension, even where the organ has a large length. The desired size of the displayed region of the luminal organ is selected by the observer according to the specific application or use of the present assisting system. When the observer wants to check a blood vessel over the entire length, for example, the blood vessel is displayed with a comparatively small size. When the observer wants to observe the condition of a portion of the wall surface of the blood vessel, that portion is displayed with a comparatively large size.

The present embodiment is further configured such that the anatomical nomenclature information stored in the anatomical information database 13 provided for storing the anatomical structure information including at least the anatomical nomenclature information is correlated with the luminal structure information 37, by the information extracting portion 12. Thus, the luminal structure information 37, and the anatomical structure information correlated with the luminal structure information 37 can be handled as a set of data.

The present embodiment is further configured such that the anatomical nomenclature of the luminal organ is displayed by the image synthesizing and displaying portion 18, on the virtual image displayed on the monitor 2, so that the observation of the luminal organ can be facilitated.

The present embodiment is further configured such that the luminal organ image generating portion 15 changes the image processing method on the basis of the anatomical structure information or the luminal structure information 37. Thus, the luminal organ image generating portion 15 permits automatic or manual change of the image processing method depending upon the specific part of the luminal organ, so that the luminal region data can be accurately extracted.

Other embodiments of this invention will next be described. In the following description, the same reference signs will be used to identify the same elements in the different embodiments, which will not be described redundantly.

Embodiment 2

Figure 39:
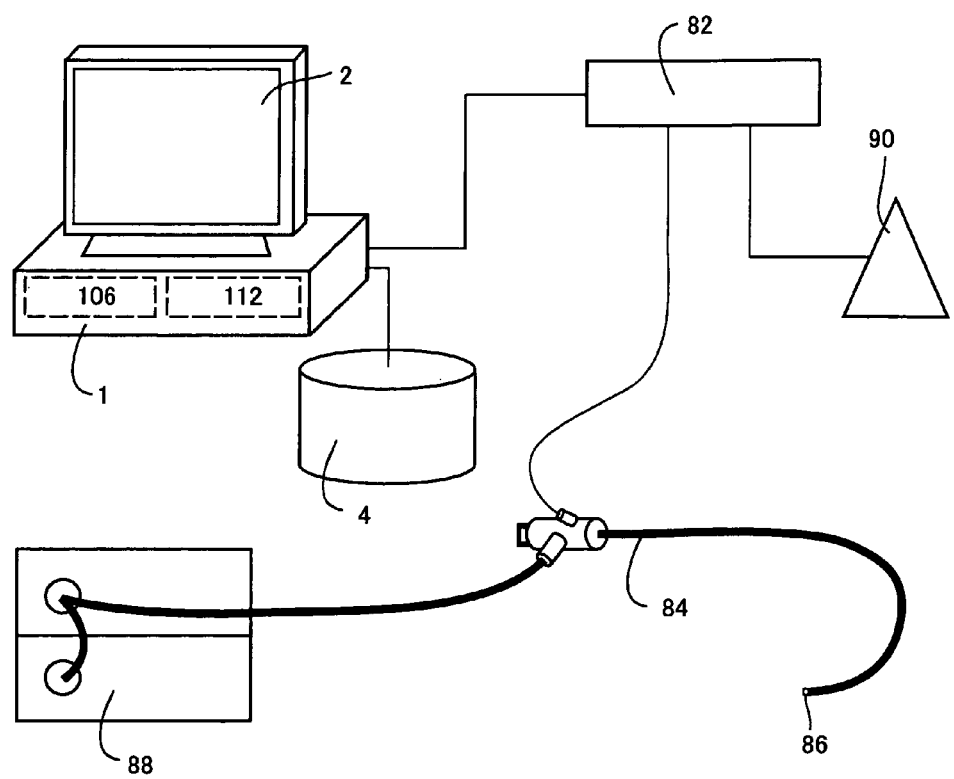
FIG. 39 is a view showing devices in Embodiment 2.

FIG. 39 is a schematic view for explaining a medical image observation assisting system in the form of the computer 1 according to the present invention. The computer 1 includes an endoscope position detecting portion 106 functioning as endoscope-position detecting means, and a first real image observing position estimating portion 112 functioning as first real-image observing-position estimating means. Also shown in FIG. 39 is an endoscope 84 which is provided at its leading end with a position sensor 86. This position sensor 86 may be a magnetic position sensor, for example. The endoscope 84 is connected to an endoscope device 88, which is configured to output an image according to an output of a small video camera provided at the leading end of the endoscope 84. A magnetic-field generating coil 90 is provided to generate a predetermined magnetic field on the basis of a command received from a position detecting device 82, and the position sensor 86 detects information relating to the generated magnetic field. The position detecting device 82 sends to the endoscope position detecting portion 106 the information relating to the magnetic field generated by the magnetic-field generating coil 90, and the information relating to the magnetic field received from the position sensor 86. On the basis of these sets of information, the endoscope position detecting portion 106 detects a relative position between the magnetic-field generating coil 90 and the position sensor 86. The endoscope position detecting portion 106 has three kinds of freedom regarding the linear position and three kinds of freedom regarding the angular position of the position sensor 86. For example, the position sensor 86 is provided by "micro BIRD" available from Assention Technology Inc. Since the position sensor 86 is extremely small and built in the leading end portion of the endoscope 84, the position detected by the position sensor 86 can be considered as the position of the leading end portion of the endoscope 84.

The control computer 1 serving as the medical image observation assisting system compares the leading end position of the endoscope 84 detected by the position detecting device 82 with the structure data of the luminal organ in the form of the organ structure information 37, to estimate the position of the leading end portion of the endoscope 84 within the luminal organ in the form of the bronchi 30.

Figure 40:
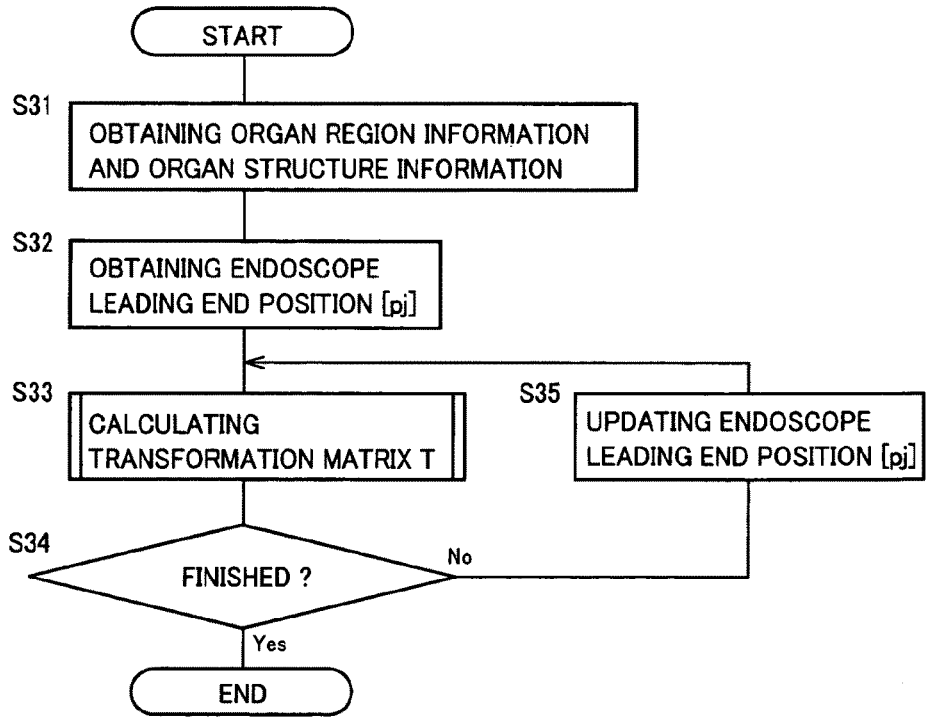
FIG. 40 is a flow chart illustrating an operation to calculate a transformation matrix T in Embodiment 2.

FIG. 40 is a flow chart illustrating a major control operation of the computer 1 according to the present embodiment, that is, an operation to estimate the position of observation of a real image. The operation is initiated with step S31 ("step" being hereinafter omitted) to read out the organ region information 35 and organ structure information 37 which have been extracted by the organ region information extracting section 12a and organ structure information extracting section 12b and which have been stored in the extracted information storing section 12f.

Figure 42:
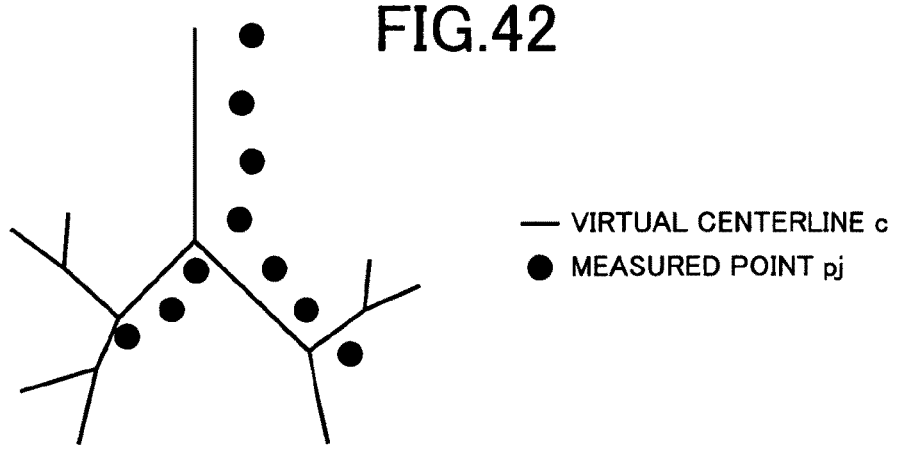
FIG. 42 is a view for explaining a relationship between a measured leading edge of an endoscope and a virtual centerline.

Then, the control flow goes to S32 corresponding to the endoscope position detecting portion 106, to retrieve from a memory device 4 a set of information relating to the position pj of the leading end portion of the endoscope 84 which was detected last by the position detecting device 82. FIG. 42 indicates a relationship between the virtual centerline "c" of the organ structure information 37 and the position pj of the endoscope 84.

Figure 41:
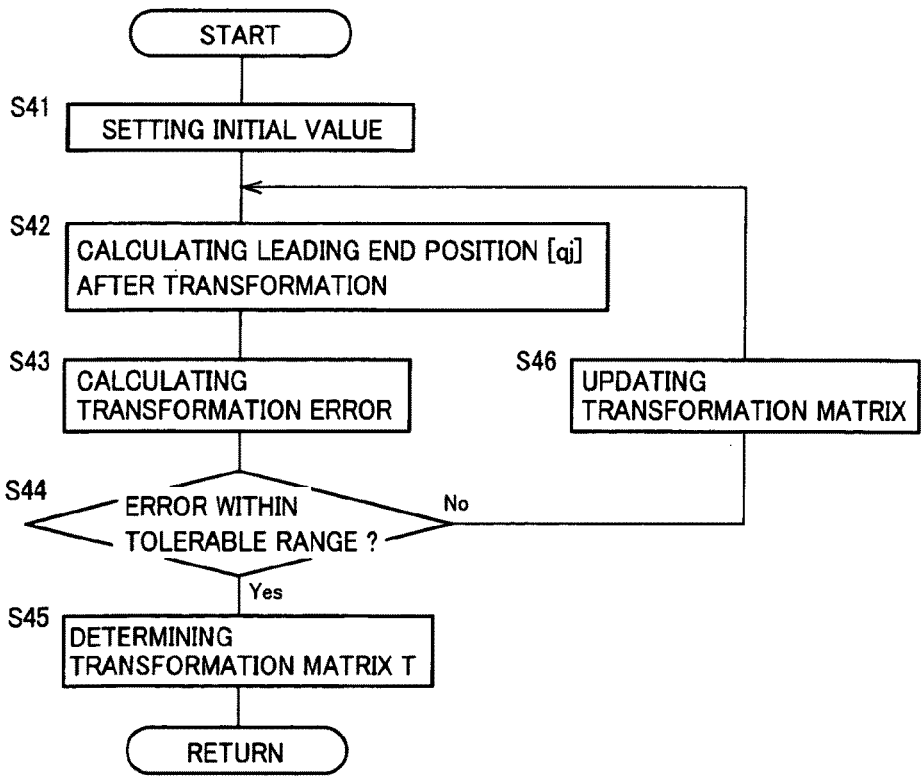
FIG. 41 is a flow chart illustrating a transformation matrix calculating routine executed in the flow chart of FIG. 40.
Figure 43:
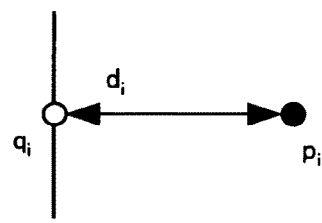
FIG. 43 is a view for explaining the measured leading end position of the endoscope, and the leading end position after transformation, and a distance therebetween.

S33 through S35 correspond to the above-descried first real image observing position estimating portion 112. In S33, a sub-routine of FIG. 41 for calculating a transformation matrix T is executed. The transformation matrix T satisfies a relationship qj=T·pj. That is, the transformation matrix T is a matrix for transforming the coordinate system in which the position detected by the position detecting device 82 is indicated, into the coordinate system in which the three-dimensional image is provided. In S41 of FIG. 41, an initial value of the transformation matrix T is determined. Then, the control flow goes to S42 to transform the coordinate values of the position pj of the leading end portion according to the transformation matrix T, into coordinate values of a position qj. The control flow then goes to S43 to calculate a transformation error "e". Initially, a distance dj between the position qj after the transformation and the virtual centerline "c". Described in detail, the distance dj is a distance between the position qj and a point of intersection between the virtual centerline "c" and a straight line which is normal to the centerline "c" and which passes through the position qj of the leading end portion, as indicated in FIG. 43. Successively, the transformation error "e" is calculated on the basis of the calculated distance dj, according to the following mathematical formula 1;

$$e = \sum_{j=1}^{l} \|w_i d_i\|^2 \quad \text{[Formula 1]}$$

Namely, the transformation error is a square sum of the weighted distance dj. In the above-indicated formula 1, "wj" represents a weight, which is set such that an influence on the error "e" decreases with an increase of the time from the present moment to a moment at which the position pj of the leading end portion was detected.

Then, the control flow goes to S44 to determine whether the transformation error "e" calculated in S43 is held within a predetermined tolerable range. If an affirmative determination is obtained in S44, the control flow goes to S46 to determine the value T at the time of implementation of S43 as the transformation matrix T, and one cycle of execution of the present routine is terminated. If a negative determination is obtained in S44, the control flow goes to S46.

In S46, the value T at the time of implementation of S43 is updated by a suitable amount, and the control flow goes back to S42 and the subsequent steps. The value T is updated by the suitable amount in the direction that causes reduction of the transformation error "e". Namely, S42-S44 and S46 are repeatedly implemented to determine the transformation matrix T with the transformation error "e" reduced to within the tolerable range.

Referring back to FIG. 40, S34 is implemented to determine whether the present routine has been repeatedly executed a predetermined sufficient number of times. If an affirmative determination is obtained in S34, the present routine is terminated. If a negative determination is obtained in S34, the control flow goes to S35. For example, the predetermined sufficient number of times is equal to the number of the endoscope positions detected by the endoscope position detecting portion 106. In this case, which S33-S35 corresponding to the first real image observing position estimating portion 112 are repeatedly implemented by this number of times.

In S35, the leading end position pj of the endoscope 84 is updated. Described in detail, the newly detected of position information is retrieved, and the oldest position information is erased such that the number of the erased set or sets is equal to the number of the retrieved set or sets.

Figure 44:
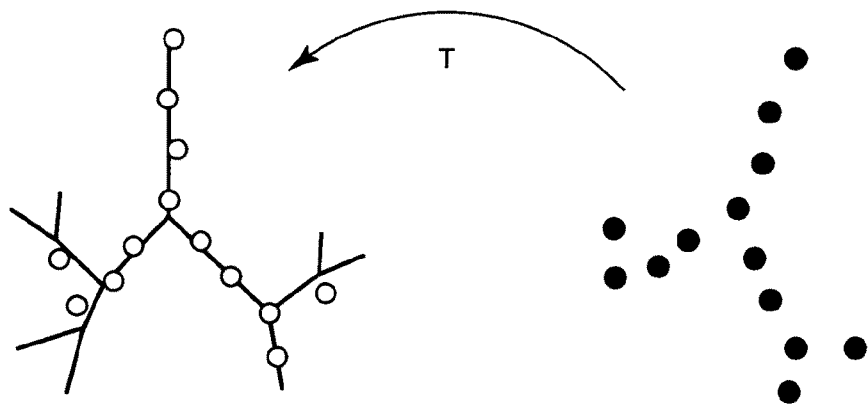
FIG. 44 is a view for explaining a concept of the transformation.

Thus, the positions pj of the leading end portion of the endoscope 84 detected in S32 corresponding to the endoscope position detecting portion 106 are converted into points on the three-dimensional image of the structure of the luminal organ represented by the organ structure information, according to the transformation matrix T calculated in S33-S35 corresponding to the first real image observing position estimating portion 112, as indicated in FIG. 44. The present embodiment permits conversion of the positions pj of the leading end portion of the endoscope 84 into the points on the three-dimensional image according to the transformation matrix T, making it possible to deal with a difference between the position of the luminal organ of the subject body when the three-dimensional CT image is generated and the position when the endoscope 84 is inserted into the luminal organ.

The present embodiment is configured such that the relative position pj of the position sensor 86 provided at the lead end portion of the endoscope 84 actually inserted into the subject body is detected by the position detecting portion 106, and the detected leading end position pj of the endoscope 84 is compared with the luminal structure data in the form of the organ structure information 37, to thereby estimate the real image observing position in the form of the observing position 75 which is the position of the leading end portion of the endoscope 84 within the luminal organ, so that the real image observing position corresponding to the leading end position of the endoscope can be further exactly detected.

In the embodiment described above, the relative position of the leading end portion of the endoscope detected by the position detecting portion 106 is compared with the above-described luminal structure data, by the first real image observing position estimating portion 112, to estimate the real image observing position, so that the position of the leading end portion of the endoscope corresponding to the real image observing position can be further exactly detected.

Embodiment 3

Figure 45:
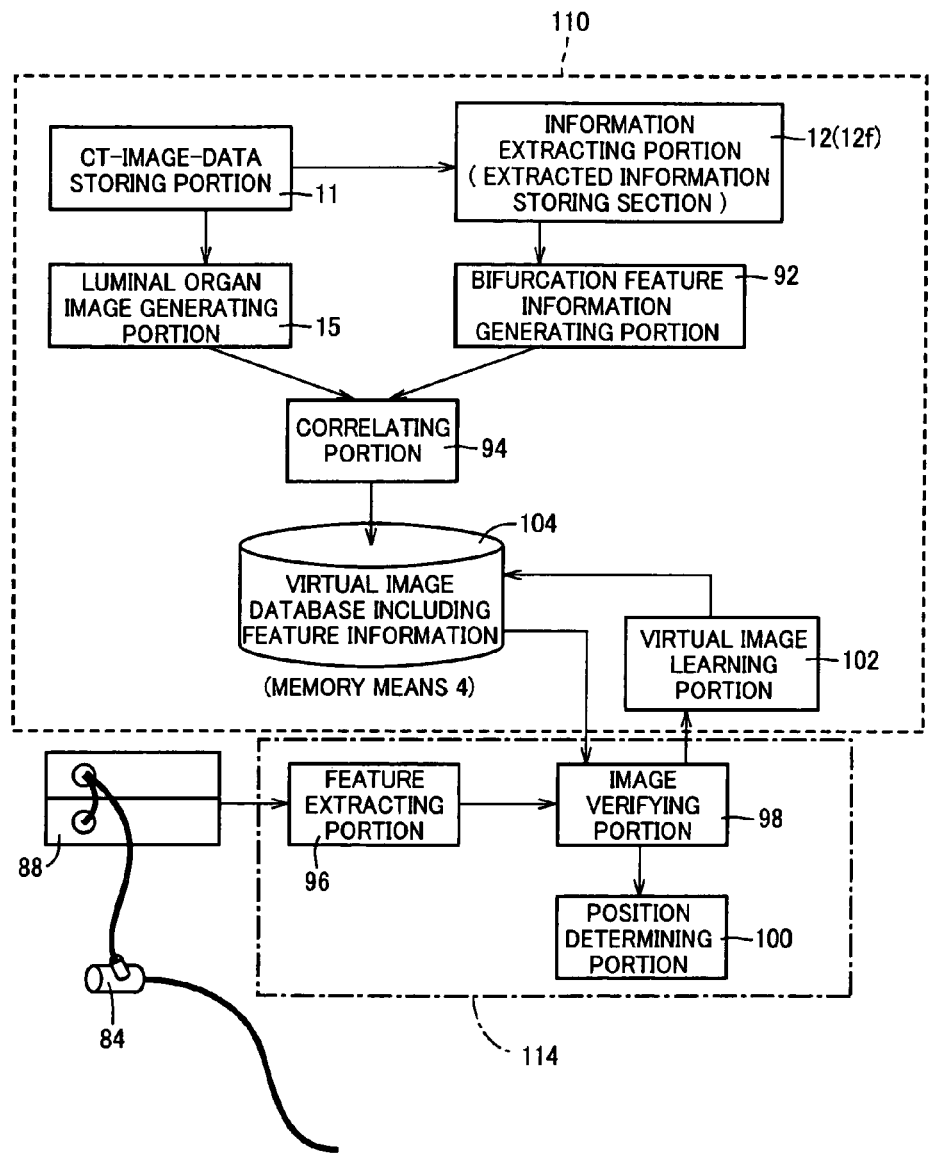
FIG. 45 is a functional block diagram for explaining major functions of a medical image observation assisting system according to Embodiment 2.

FIG. 45 is a functional block diagram showing a further embodiment of the invention, that is, indicating major functions of the computer 1 serving as the medical image observation assisting system provided with virtual-image storing means and second real-image observing-position estimating means. In the present embodiment, a virtual image memory portion 110 which is provided as the virtual-image storing means includes a bifurcation feature information generating portion 96, a correlating portion 94, and a virtual image learning portion 96, which will be described, and a second real image observing position estimating portion 114 which is provided as the second real-image observing-position estimating means includes a feature extracting portion 96, an image verifying portion 98 and a position determining portion 100, which will be described. That is, a portion of FIG. 45 enclosed by broken line corresponds to the virtual image memory portion 110, while a portion of FIG. 45 enclosed by one-dot chain line corresponds to the second real image observing position estimating portion 114.

The bifurcation feature information generating portion 92 functioning as bifurcation-feature-information generating means is configured to detect portions of the luminal organ at which the organ is bifurcated (hereinafter referred to as "bifurcated portions"), on the basis of the organ structure information 37 stored in the information extracting portion 12 (extracted information storing section 12f), in particular, the information relating to the virtual centerline "c". On the basis of the organ structure information 37 of the detected bifurcated portions, the bifurcation feature information generating portion 92 generates information (hereinafter referred to as "bifurcation feature information") relating to features appearing on a virtual image including each bifurcated portion. These features appearing on the virtual image include at least one of: the number of holes seen in the luminal organ extending in the direction perpendicular to the plane of the monitor screen; the positions of the holes; and the luminosity of the image of the holes. All of the features can be calculated on the basis of the structure of the organ represented by the organ structure information 37. The luminosity of the image of the holes is a feature based on the length of the luminal organ, and decreases with an increase of the length of the organ. Namely, the image of the hole having a relatively low degree of luminosity is relatively dark. An example of this image is shown in FIG. 49.

FIG. 49 shows the virtual images of four different bifurcated portions, and the bifurcation feature information extracted from the virtual images. In FIG. 49, the left column shows the virtual images of the bifurcated portions while the right column shows the bifurcation feature information of the bifurcated portions. Although only the number and positions of the holes are indicated in FIG. 49, the bifurcation features include the luminosity of the holes in addition to the number and positions of the holes. Accordingly, case 1 and case 2 which have the same number and positions of the holes can be distinguished from each other by different degrees of the luminosity of the holes.

The correlating portion 94 functioning as correlating means is configured to correlate the virtual image generated by the luminal organ image generating portion 15, with the bifurcation feature information generated by the bifurcation feature information generating portion 92, and to store the correlated virtual image and bifurcation feature information in the memory portion 4 functioning as memory means, which constitutes a virtual image database 104 which stores the virtual images together with the bifurcation feature information.

The feature extracting portion 96 functioning as feature extracting means is configured to extract features corresponding to the bifurcation feature information of a real endoscope image which is taken by a video camera attached to the leading end of the endoscope 84 and which is processed by the endoscope device 88.

The image verifying portion 98 functioning as image verifying means is configured to verify the bifurcation feature information of the virtual image stored in the virtual image database 104, on the basis of the bifurcation feature information of the real endoscope image extracted by the above-described feature extracting portion 96. The image verifying portion 98 selects the virtual image correlated to the bifurcation feature information verified to match the bifurcation feature information of the real endoscope image.

The position determining portion 100 functioning as position determining means is configured to determine the observing position (point of view) 75 of the virtual image selected by the image verifying portion 98, as the position of the leading end portion of the endoscope upon taking of the real endoscope image.

The virtual image learning portion 102 functioning as virtual-image leaning means is configured to compare the virtual image selected by the image verifying portion 98, with the real endoscope image, and to modify the virtual image such that the bifurcation feature information of the virtual image matches the bifurcation feature information of the real endoscope image.

Figure 46:
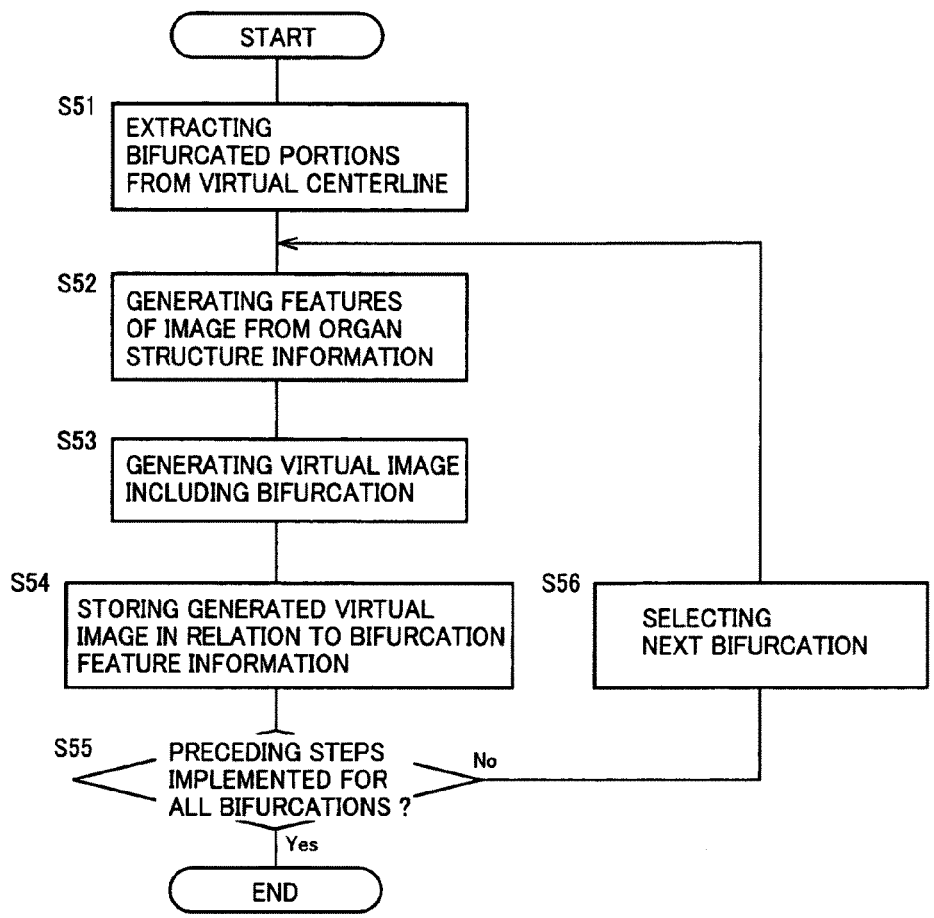
FIG. 46 is a flow chart illustrating a major operation corresponding to virtual image memory means of the medical image observation assisting system according to Embodiment 2.
Figure 47:
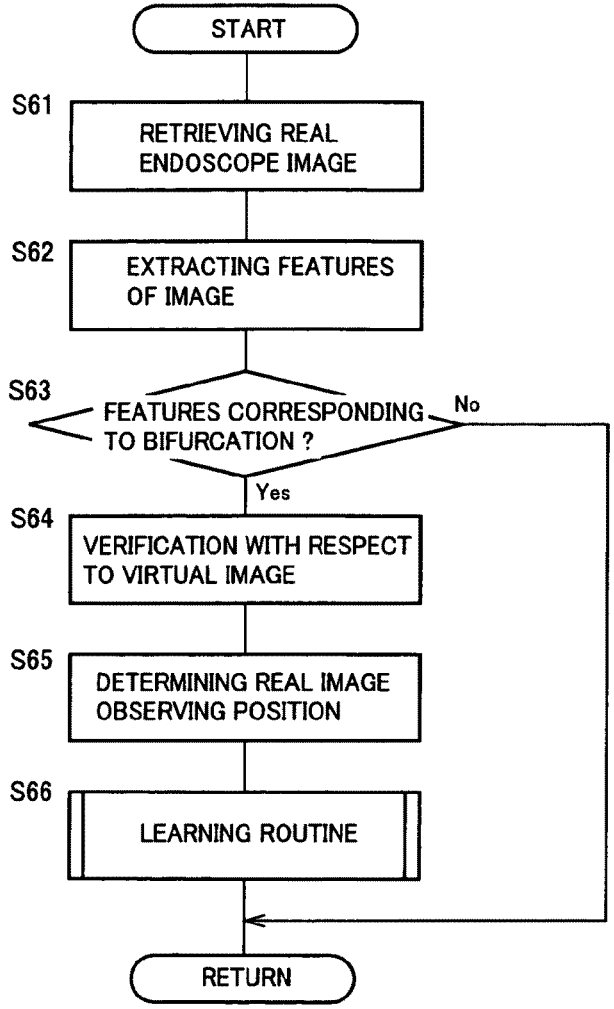
FIG. 47 is a flow chart illustrating a major operation corresponding to second virtual image observing position estimating means 114 of the medical image observation assisting system according to Embodiment 2.
Figure 48:
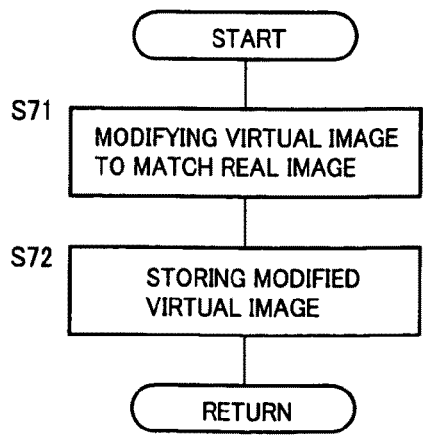
FIG. 48 is a view illustrating a learning routine executed in the flow chart of FIG. 47.

FIG. 46 through FIG. 48 are flow charts illustrating major control operations of the computer 1 serving as the medical image observation assisting system according to the present embodiment. The flow chart of FIG. 46 corresponds to the operation of the virtual image memory portion 110, while the flow chart of FIG. 47 corresponds to the operation of the second real image observing position estimating portion 114. The flow chart of FIG. 48 illustrates a learning routine executed in the flow chart of FIG. 47.

The control operation of the flow chart of FIG. 46 is initiated with S51 and S52 corresponding to the bifurcation feature information generating portion 92. In S51, the organ structure information 37 is read out from the extracted information storing section 12f, and the bifurcated portions of the virtual centerline "c" are detected on the basis of the information relating to the virtual centerline "c". In S52, the bifurcation feature information appearing on the virtual image including each bifurcated portion is generated. As described above, the bifurcation feature information includes at least one of the number of the holes in the luminal organ extending in the direction perpendicular to the monitor screen, the positions of the holes and the luminosity of the image of the holes.

Then, the control flow goes to S53 corresponding to the luminal organ image generating portion 15, to generate the virtual image including the bifurcated portion. Where a plurality of virtual images have already been generated and stored in the memory means 4, the virtual image including the appropriate bifurcated portion is selected from those virtual images.

In S54 corresponding to the correlating portion 94, the bifurcation feature information generated in S52 and the virtual image which includes the appropriate bifurcated portion and which is generated in S53 are correlated with each other and stored to generate the virtual image database 104 including the bifurcation feature information.

In S55, a determination is made as to whether S52-S54 have been implemented for all of the bifurcated portions of the virtual centerline "c". If S52-S54 have been implemented for all of the bifurcated portions, an affirmative determination is obtained in S55, and the operation of the present flow chart is terminated. If S52-S54 have not been implemented for all of the bifurcated portions, the control flow goes to S56 to select the next bifurcated portion so that S52-S54 are repeated for the next bifurcated portion.

Referring next to the flow chart of FIG. 47, this flow chart corresponds to the second real image observing position estimating portion 114. In S61, the real endoscope image taken by the video camera attached to the leading end portion of the endoscope 84 and processed by the endoscope device 88 is retrieved into the computer 1 serving as the medical image observation assisting system.

In S62 corresponding to the feature extracting portion 96, the features corresponding to the bifurcated feature information are extracted from the real endoscope image retrieved in S61. The control flow then goes to S63 to determine whether the features extracted in S62 correspond to the bifurcation of the luminal organ. An affirmative determination is obtained in S63 if the features corresponding to the bifurcation of the luminal organ appear on the real endoscope image. In this case, the control flow goes to S64 and the subsequent steps. If the features corresponding to the bifurcation of the luminal organ does not appear on the real endoscope image, for example, if the features appearing on the real endoscope image do not correspond to the bifurcation of the luminal organ, or if the features that can be detected in S62 do not exist, the operation of the present flow chart is terminated.

In S64 corresponding to the image verifying portion 98, the real endoscope image and the virtual image stored in the virtual image database 104 are compared with each other for verification, by comparing the features of the real endoscope image extracted in S62 with the bifurcation feature information correlated with each virtual image stored in the virtual image database 104. The virtual image verified to match the real endoscope image is selected. This verification is made by determining whether the virtual image falls within a predetermined range of similarity to the real endoscope image.

In S65 corresponding to the position determining portion 100, the position of the leading end portion of the endoscope 84 upon taking of the real endoscope image retrieved in S61 is determined as the observing position (point of view) 75 of the virtual image selected in S64.

In S66 corresponding to the virtual image leaning portion 102, the learning routine illustrated in FIG. 48 is executed to reflect a result of verification in S64 on the virtual image database 104 including the bifurcation feature information. In S71 of FIG. 48, the virtual image selected in S64 is modified to change the positions and luminosity of the holes, for example, so that the modified virtual image has the features of the real endoscope image retrieved in S61.

In S72, the virtual image modified in S71 is stored, in place of the original virtual image, in the virtual image database 104.

In the present embodiment, the features corresponding to the structure information of the bifurcated portions appearing on the real endoscope image are extracted by the second real image observing position estimating portion 114, and the extracted features are verified on the basis of the bifurcation feature information generated from the luminal structure data stored in the virtual image database 104. The virtual image correlated to the bifurcation feature information verified to match the read endoscope image is selected, and the observing portion 76 of the selected virtual image is estimated to be the real image observing position. Thus, the leading end position of the endoscope can be estimated without actually detecting the leading end position of the endoscope. Further, the verification of the real endoscope image and the virtual image is based on the features corresponding to the luminal structure data appearing on the image, so that the verification can be made in a reduced time and with a high degree of accuracy.

The present embodiment is configured such that the second real image observing position estimating portion 114 extracts the features which appear on the real endoscope image and which correspond to the luminal structure data, verifies the extracted features with respect to the organ structure information 37 stored in the virtual image memory portion 110, and estimates the observing position 75 of the virtual image corresponding to the organ structure information 37 verified to match the extracted features, as the observing position of the real endoscope image. Thus, the leading end position of the endoscope 84 can be estimated without actually detecting the leading end position of the endoscope 84. Further, the verification of the real endoscope image and the virtual image is based on the features corresponding to the organ structure information 37 appearing on the image, so that the verification can be made in a reduced time and with a high degree of accuracy.

The present embodiment is further configured such that the real endoscope image and the virtual image are verified or compared with respect to each other on the basis of at least one feature of the virtual image and endoscope image which corresponds to the luminal structure data and which is selected from the number and positions of the luminally structural portions and the luminosity of the image of the luminally structural portions. Thus, it is not necessary to verify the entirety of the images.

The present embodiment is further configured such that the virtual-image learning portion 102 of the second real image observing position estimating portion 114 modifies the contents of the virtual image memory portion 110 on the basis of the above-described verification, so that the accuracy of verification is improved as the verification is repeated.

Embodiment 4

Figure 50:
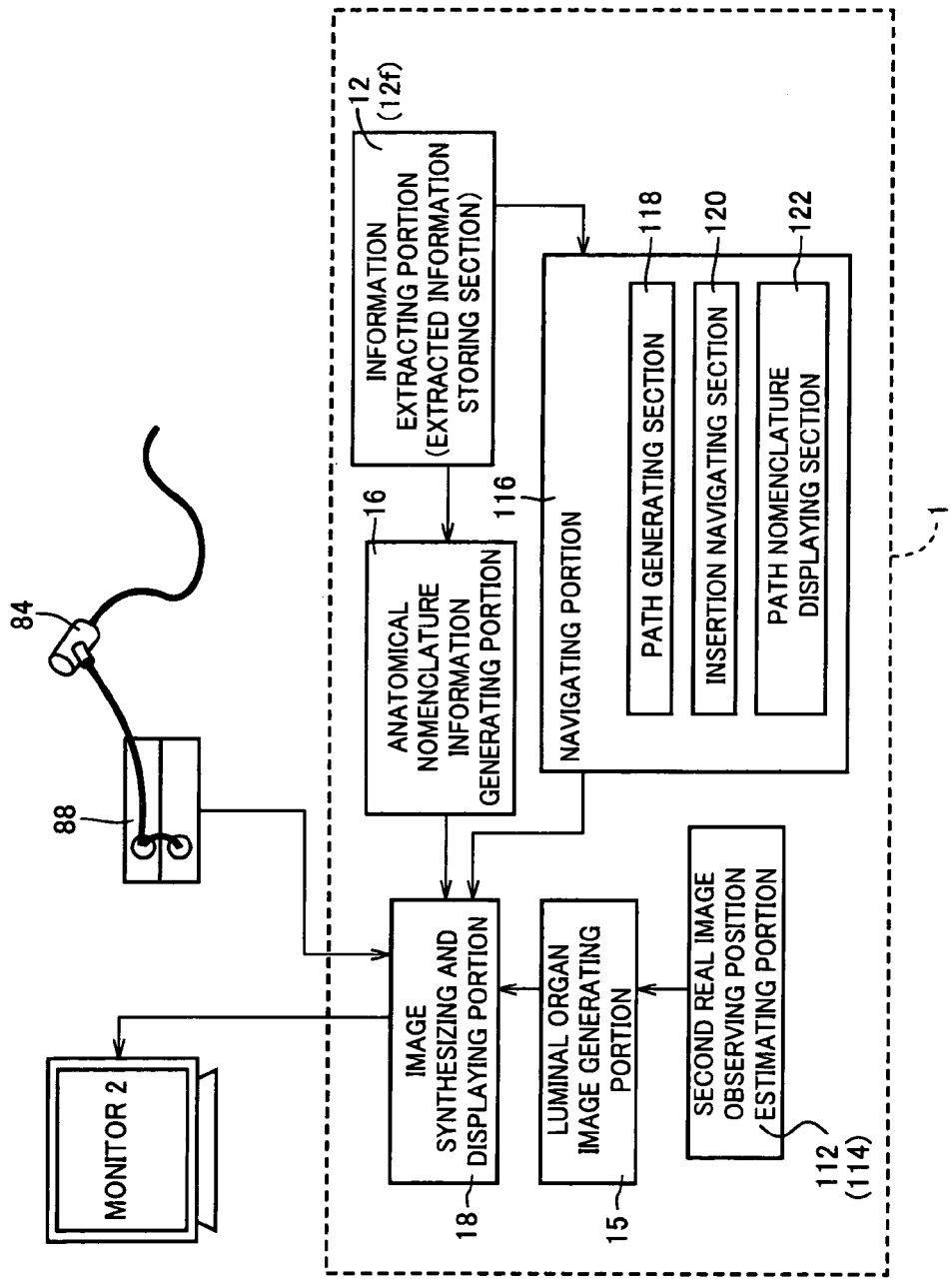
FIG. 50 is a functional block diagram showing major functions of a medical image observation assisting system according to Embodiment 4.

FIG. 50 is a functional block diagram showing a still further embodiment of the invention, that is, indicating major functions of the computer 1 serving as the medical image observation assisting system provided with the above-described image synthesizing means, and navigating means.

As shown in FIG. 50, the image synthesizing and displaying portion 18 functioning as the image synthesizing means displays on the display means in the form of the monitor 2 the real endoscope image which is taken by the video camera attached to the leading end portion of the endoscope 84 and which is obtained through the endoscope device 88, and the virtual image generated by the luminal organ image generating portion 15 functioning as the virtual-image generating means, such that the real endoscope image and the virtual image can be compared with each other. The luminal organ image generating portion 15 is configured to generate the virtual image such that the real-image observing position estimated by the first real image observing position estimating portion 112 or the second real image observing position estimating portion 114 is determined as the observing position of the virtual image. Accordingly, the virtual image is obtained at the observing position of the real endoscope image, namely, displayed at the same position and in the same scale as the real endoscope image.

Figure 52:
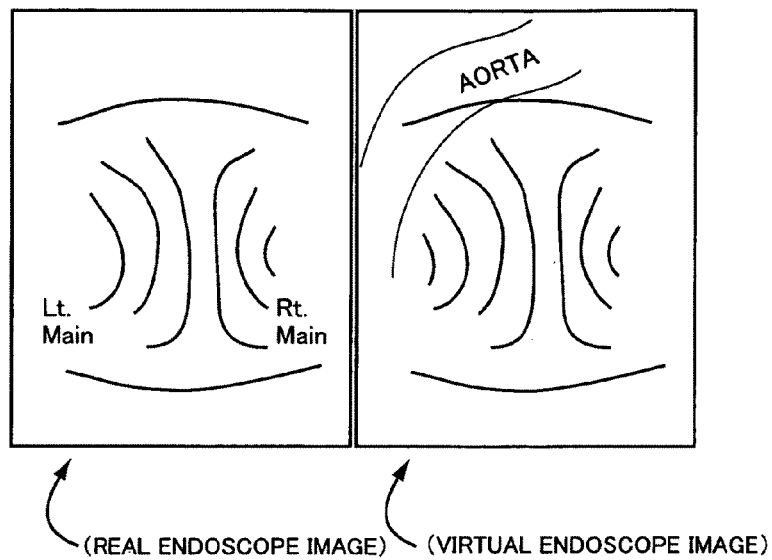
FIG. 52 is a view indicating examples of a display provided on a monitor 2 in Embodiment 4.

The image synthesizing and displaying portion 18 displays the anatomical nomenclature (in the form of letters, for example) which is correlated, by the anatomical nomenclature information generating portion 16, with the corresponding portions of the luminal organ displayed as the virtual image or the endoscope image, such that the anatomical nomenclature is superimposed on the virtual or endoscope image, as indicated in FIG. 52 by way of example.

On the other hand, a navigating portion 116 functioning as the navigating means includes a path generating section 118 serving as path generating means, an insertion navigating section 120 serving as insertion navigating means, and a path nomenclature displaying section 122 serving as path-nomenclature displaying means. The navigating portion 116 is configured to detect a path through the luminal organ to a desired or target portion specified with three-dimensional image data, and to command the image synthesizing and displaying portion 18 to display information for assisting the operator to insert the endoscope along the detected path.

The path generating section 118 is operated when the operator specifies, with the three-dimensional image data, the target portion of the organ, namely, the portion of the organ to which the operator desires to insert the endoscope. The path generating section 118 is configured to detect the path to the specified target portion of the luminal organ. This detection of the path is implemented by storing information indicating selected one of branches at each bifurcated portion or branching point of the organ, through which the endoscope should be advanced.

The insertion navigating section 120 is configured to command the image synthesizing and displaying portion 18 according to the path generated by the path generating section 118, to indicate the selected one of the plurality of branches through which the endoscope 84 should be advanced, when the endoscope 84 has almost reached each bifurcated portion. Described in detail, the insertion navigating section 120 determines that the endoscope 84 has almost reached a bifurcated portion when the bifurcation feature information appears on the real endoscope image, or when it is determined on the basis of the organ structure information that the position of the leading end portion of the endoscope 84 estimated by the first real image observing position estimating portion 112 or second real image observing position estimating portion 114 has been moved to a position immediately before the bifurcated portion. On the basis of the path generated by the path generating portion 118, one of the branches at the bifurcated portion is selected so that the endoscope is advanced into the selected branch. The insertion navigating section 120 is further configured to command the image synthesizing and displaying portion 18 to indicate the selected path on the real endoscope image or the virtual image, or on both of the real endoscope image and virtual image.

Figure 54:
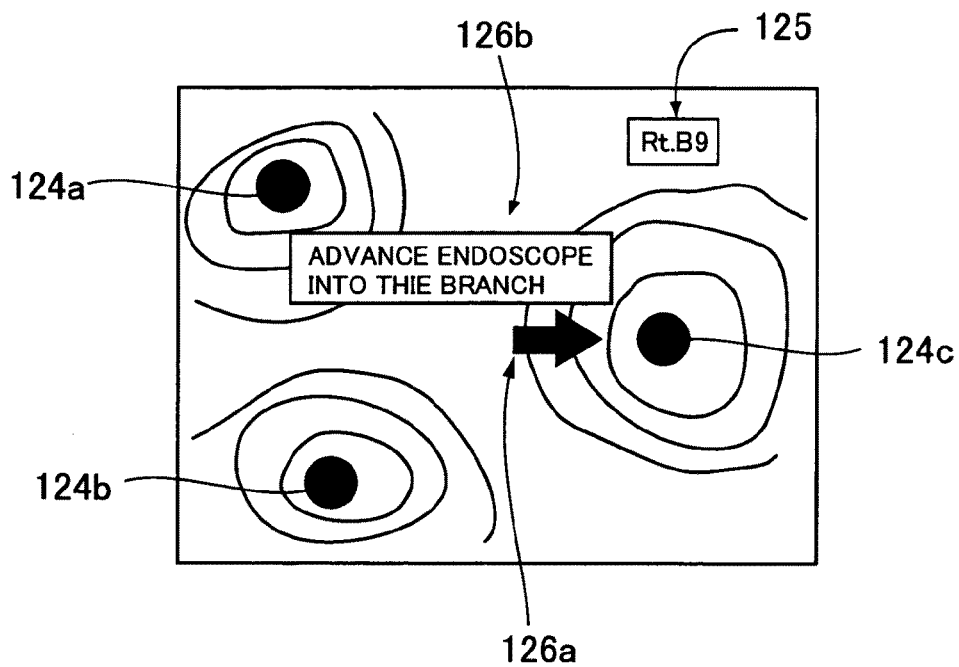
FIG. 54 is a view indicating an example of a display provided on the monitor 2 in Embodiment 4.

FIG. 54 indicates examples of a display provided together with the real endoscope or virtual image, where branches 124a, 124b and 124c exist at the detected bifurcated portion. When the insertion navigating section 120 determines, on the basis of the path generated by the path generating section 118, that the endoscope 84 should be inserted into the branch 124c, the insertion navigating section 120 commands the image synthesizing and displaying portion 18 to provide an indication that the endoscope 84 should be advanced into the branch 124c. This indication may be made by an arrow 126a or a message 126b in the form of letters, as indicated in FIG. 54, or a combination thereof.

The path nomenclature displaying section 122 is configured to read out from the extracted information storing section 12f the anatomical nomenclature correlated to the portions of the luminal organ which define the path generated by the path generating section 118. Thus, the path generated by the path generating section 118 can be identified by the anatomical nomenclature. The path nomenclature displaying section 122 is further configured to command the image synthesizing and displaying portion 18 to display information relating to the path identified by the anatomical nomenclature, according to an operation of the operator.

Figure 53:
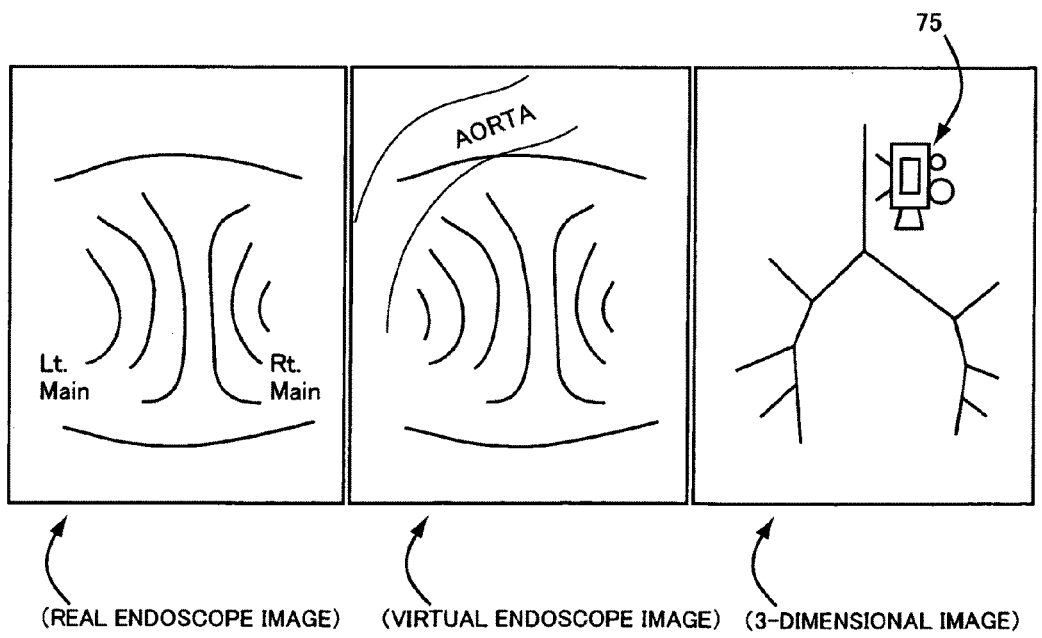
FIG. 53 is a view indicating examples of a display provided on the monitor 2 in Embodiment 4.
Figure 55:
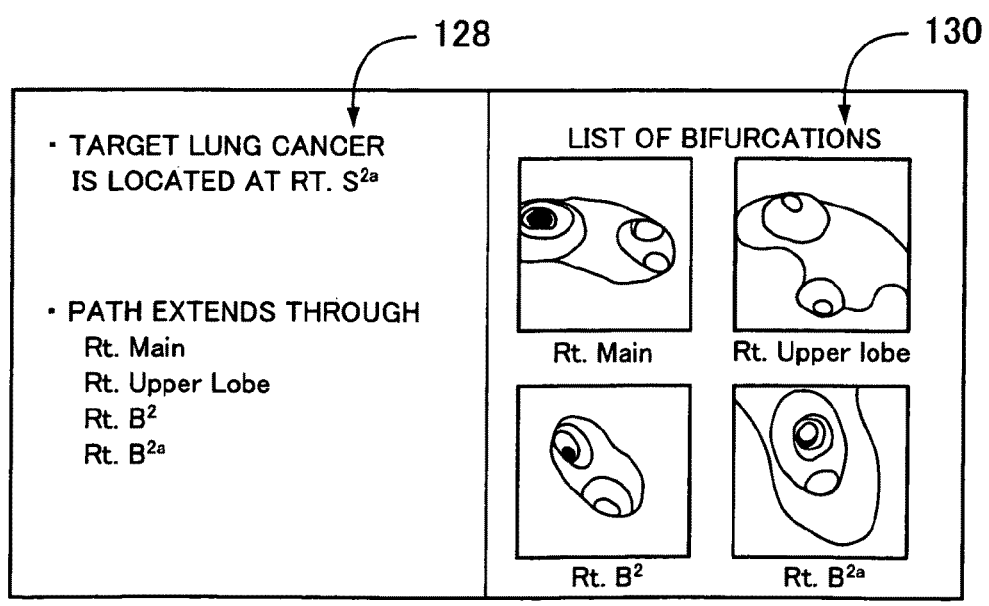
FIG. 55 is a view indicating an example of a display provided on the monitor 2 in Embodiment 4.

FIG. 55 shows an example of the above-indicated information provided on the monitor 2. A left half of the screen of the monitor 2 shown in FIG. 55 is a path nomenclature displaying area 128, while a right half of the screen is an image displaying area. The path nomenclature displaying area 128 is provided to display the information relating to the path identified by the anatomical nomenclature, namely, anatomical names of the portions of the luminal organ which defines the above-indicated path, in the order from the name of the portion at the present position of the endoscope to the name of the target portion. The image displaying area 130 may display only the virtual images of the bifurcated portions, as indicated in FIG. 55, or display the virtual images and the real endoscope images such that the virtual and real endoscope images can be compared with each other, as indicated in FIG. 52, or may superimpose the selected path on the real endoscope image or the virtual image, as indicated in FIG. 53, as described above with respect to the insertion navigating section 120. The image displaying section 130 may be omitted.

Figure 51:
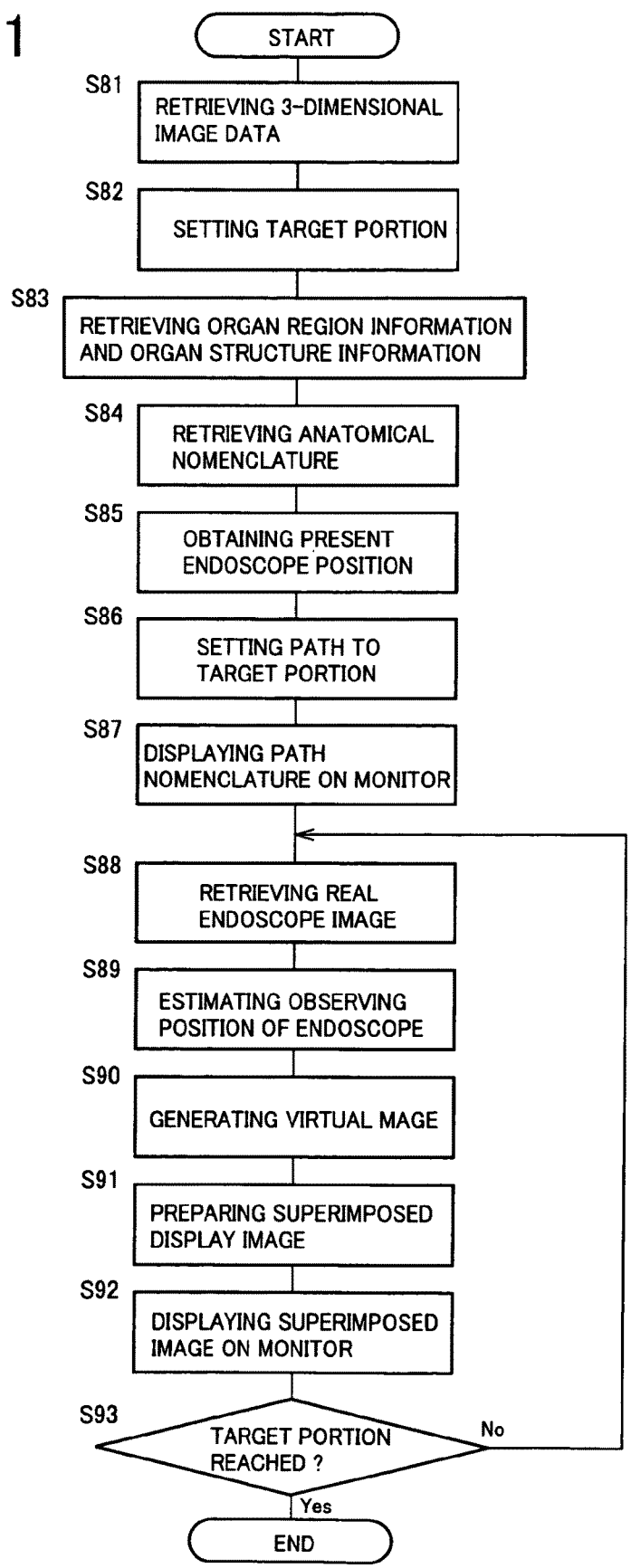
FIG. 51 is a flow chart illustrating a major operation of the medical image observation assisting system according to Embodiment 4.

FIG. 51 is a flow chart illustrating major an operation of the computer 1 serving as the medical image observation assisting system according to the present embodiment. The operation is initiated with S81 to retrieve the three-dimensional image data from the CT-image-data storing portion 11 (shown in FIG. 1). Then, the control flow goes to S82 set, in the retrieved three-dimensional image data, the target portion of the luminal organ to which the inserted endoscope 84 is to be advanced. This target portion is specified by the operator through the input portion 3, for example.

Then, the control flow goes to S83 the organ region information 35 and the organ structure information 37 from the information extracting portion 12 (extracted information storing section 12f). S84 is then implemented to retrieve from the information extracting portion 12 (extracted information storing section 12f) the anatomical information correlated to the portions of the luminal organ for which the organ region information 35 and organ structure information 37 have been retrieved in S83.

S85 and S86 correspond to the path generating section 118. In S85, the position at which the navigation is initiated is set. This position of initiation of the navigation may be set by the endoscope position detecting portion 106, or may be estimated by the first real image observing position estimating portion 112 or second real image observing position estimating portion 114. Prior to the insertion of the endoscope into the subject body, the position of initiation of the navigation may be the position from which the endoscope is inserted.

In the next step S86, the path through the luminal organ from the position of initiation of the navigation set in S85 to the target portion set in S82 is determined. Where the luminal organ has only bifurcated portions, the path can be set by merely setting the start of initiation of the navigation and the target portion. Where the luminal organ has not only the bifurcated portions but also merging portions, on the other hand, a plurality of paths may be available upon setting the position of initiation of the navigation and the target portion. In this case, one of the plurality of paths is selected depending upon the shortest one of the lengths of the paths and the ease of insertion of the endoscope into the paths, for instance.

In S87 corresponding to the path nomenclature displaying section 122, the path determined in S86 is identified by the anatomical nomenclature retrieved in S83. Namely, the anatomical name correlated to each of the portions of the luminal organ which define the path determined in S83 are selected from the retrieved anatomical nomenclature. Then, the anatomical names correlated to the respective portions of the luminal organ defining the path are displayed on the monitor 2, in the order from the position of initiation of the navigation to the target portion, according an operation by the operator.

In S88, the real endoscope image taken by the video camera attached to the leading end portion of the endoscope 84 is retrieved through the endoscope device 88. Then, S89 corresponding to the first real image observing position estimating portion 112 or second real image observing position estimating portion 114 is implemented to estimate the position of the video camera attached to the leading end portion of the endoscope 84 upon taking of the real endoscope image.

Then, the control flow goes to S90 corresponding to the luminal organ image generating portion 15, to generate the virtual image such that the real-image observing position estimated in S89 is set as the observing position 75. Since the estimated real-image observing position is used as the observing position 75 of the generated virtual image, the generated virtual image is substantially the same image as viewed from the point of view and in the direction of the line of view as the real endoscope image. Accordingly, the virtual image and the real endoscope image can be easily compared with each other.

In S91 corresponding to the anatomical nomenclature generating portion 16 and the insertion navigating section 120, image data for displaying the anatomical nomenclature superimposed on the real endoscope image retrieved in S88 or the virtual image generated in S90 is prepared. Described in detail, the image data are prepared to display letters of the anatomical names correlated to the respective portions of the luminal organ represented by the real endoscope image or virtual image, and a symbol or letters (arrow 126a and letters 126b indicated in FIG. 54, for example) indicative of the branch at each bifurcation into which the endoscope is to be advanced.

In S92 corresponding to the image synthesizing and displaying portion 18, the generated sets of image data are suitably selected according to an operation by the operator, so that the appropriate images are synthesized according to the selected sets of image data and displayed on the monitor 2. For instance, the real endoscope image retrieved in S88 and the virtual image generated in S90 are displayed such that the real endoscope image and virtual image can be compared with each other, while at the same time the anatomical nomenclature generated in S91 are superimposed on the displayed real endoscope image and the virtual image as shown in FIG. 52. Alternatively, the three-dimensional image data retrieved in S81 may be displayed in addition to the information shown in FIG. 52, as shown in FIG. 53. Further alternatively, the symbol or other image which is generated in S91 and which indicates the branch into which the endoscope is to be advanced, and letters 125 indicated in FIG. 54, for example) which are also generated in S91 and which represent the anatomical names of the organs to be observed are superimposed on the real endoscope image retrieved in S88, as shown in FIG. 54. Alternatively, letters representing an array of the anatomical names defining the selected path are displayed together with desired images. The different modes of display described above are selected as needed according to an operation by the operator.

The present embodiment is configured such that the image synthesizing portion 18 displays on the monitor 2 the real endoscope image and the virtual image which corresponds to the real endoscope image and which is generated by the virtual-image generating means such that the real endoscope image and the virtual image can be compared with each other.

The present embodiment is further configured such that the luminal organ image generating portion 15 generates the virtual image such that the real-image observing position estimated by the first real image observing position estimating portion 112 is determined as the observing position 75 of the virtual image. Accordingly, the virtual image is obtained at the observing position which is estimated to be the real-image observing position at which the real endoscope image has been obtained.

The present embodiment is further configured such that the luminal organ image generating portion 15 generates the virtual image such that the real-image observing position estimated by the second real image observing position estimating portion 114 is determined as the observing position of the virtual image. Accordingly, the virtual image is obtained at the observing position which is estimated to be the real-image observing position at which the real endoscope image has been obtained.

The present embodiment is further configured such that the image synthesizing portion 15 of the medical image observation assisting system displays the anatomical nomenclature of the luminal organ on the real endoscope image displayed on the monitor 2, on the basis of correlation of the anatomical nomenclature by the information extracting portion 12. Accordingly, the portion of the luminal organ the real endoscope image of which is displayed can be identified by the anatomical nomenclature.

The present embodiment is further configured such that the navigating portion 116 displays an indication of one of the plurality of branches of the luminal organ open at a bifurcated portion thereof indicated on the real endoscope image displayed on the monitor 2, so that the endoscope 84 is navigated into the above-indicated one of the plurality of branches. Accordingly, the operator can recognize one of the plurality of branches of the luminal organ at each bifurcated portion into which the endoscope 84 should be advanced toward the target portion, so that the endoscope can be easily inserted to the target portion.

The present embodiment is further configured such that the navigating portion 116 automatically generates the above-described selected path, and displays a plurality of anatomical names correlated with the respective organs of the luminal organ defining the path, in the order from the position of insertion of the endoscope to the target portion. Accordingly, the displayed anatomical names permit the operator to recognize the path to the target portion of the luminal organ to which the endoscope is inserted, owing to the navigating means which is configured to automatically generates the path, and to display the plurality of anatomical names correlated with the respective organs of the luminal organ defining the path, in the order from the position of insertion of the endoscope to the target portion.

Embodiment 5

Figure 56:
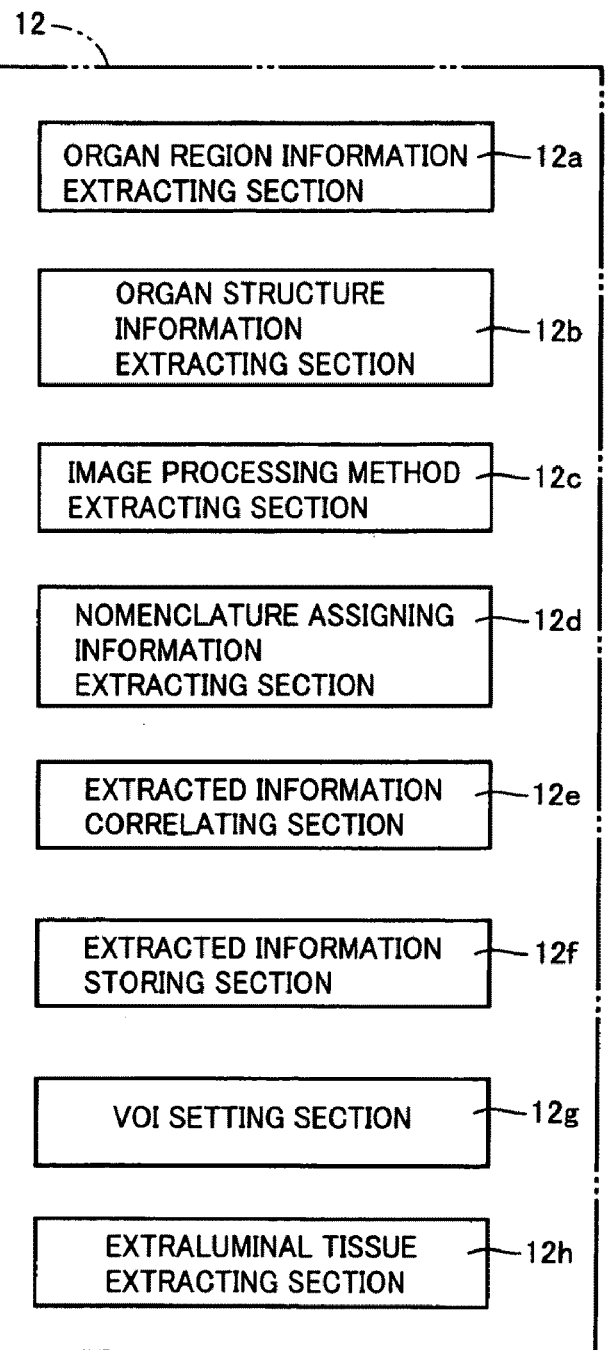
FIG. 56 is a view corresponding to that of FIG. 2, showing major functions of the information extracting portion 12 in Embodiment 5.

The computer 1 serving as the medical image observation assisting system according to the present is similar to that shown in FIG. 1. Namely, the information extracting portion 12 (shown in FIG. 1) in the present embodiment has an arrangement as shown in FIG. 56, which is different from the arrangement shown in FIG. 2, in that the information extracting section 12 in the present embodiment further includes an extraluminal issue extracting section 12h. Functions of the present embodiment different from those of the embodiment of FIGS. 1 and 2 will be described.

The extraluminal tissue extracting section 12h functioning as extraluminal tissue extracting means is configured to extract an image of tissues outside the luminal organ, by analyzing the above-described three-dimensional image, and to generate extraluminal tissue structure information relating to the size of the extraluminal tissues and the positions of the extraluminal tissues within the three-dimensional image.

The extracted information correlating section 12e is configured to store the extraluminal tissue structure information in the extracted information storing section 12f such that the extraluminal tissue structure information is correlated with anatomical numbers (described below), as well as to store the organ region information 35 and the organ structure information 37 in the extracted information storing section 12f such that the information 35 and information 37 are correlated with the anatomical information.

The anatomical information DB 13 stores not only the anatomical structure information in the form of the anatomical model information illustrated in FIG. 3, but also anatomical structure information in the form of the anatomical numbers of the extraluminal tissues. Described in detail, the anatomical information DB 13 stores the anatomical structure information in the form of items (1)-(6) of anatomical model information indicated below by way of example, for each of the anatomical numbers "n"
(1) Lymph node number
(2) Diameter and degree of sphere
(3) Average information and dispersion information of intensity values of three-dimensional image
(4) Anatomical nomenclature information of nearest luminal organ (e.g., blood vessel)
(5) Information of distance from a main focus
(6) Information of optimum image processing method The information extracting portion 12 determines the anatomical numbers of the extraluminal tissues extracted by the extraluminal-tissue extracting section 12h, on the basis of the information stored in the anatomical information DB 13, and stores the determined anatomical numbers in the extracted information storing section 12f such that the anatomical numbers are correlated with the extraluminal tissues.

The luminal organ image generating portion 15 functioning as the virtual-image generating means is configured to generate not only the virtual image of the luminal organ, but also an image of the extraluminal tissues as superimposed on the virtual image of the luminal organ, in a predetermined relationship of position and size between the virtual image and the image of the extraluminal tissues, by processing the CT image data stored in the CT-image-data storing portion 11, on the basis of the structure information of the extraluminal tissues extracted by the extraluminal tissue extracting section 12h.

The anatomical nomenclature information generating portion 16 is configured to generate not only the character image data on the basis of the nomenclature assigning information received from the information extracting portion 12, but also character image data of the anatomical numbers correlated with the extraluminal tissues.

Figure 57:
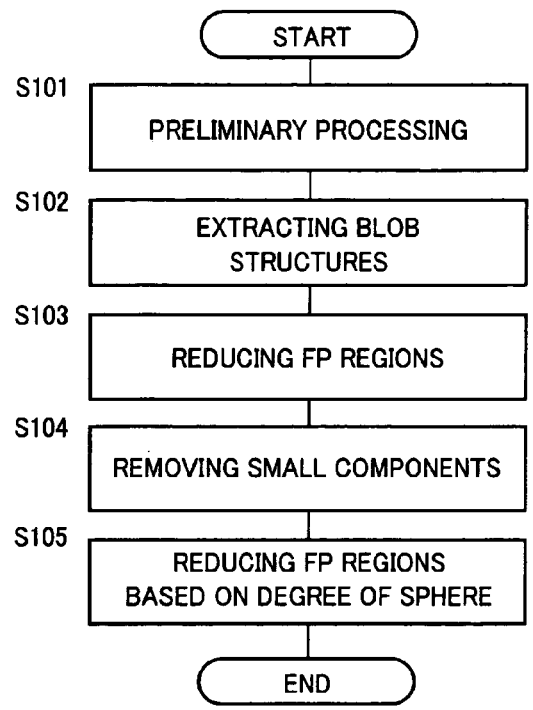
FIG. 57 is a flow chart illustrating a major operation of a medical image observation assisting system according to Embodiment 5.

FIG. 57 is a flow chart illustrating a major operation of the extraluminal tissue extracting section 12h described above. The operation is initiated with S101 to retrieve the three-dimensional image, and implement preliminary processing of the retrieved three-dimensional image, to extract the extraluminal tissues. The preliminary processing includes a filtering operation to remove noises, and a subsequent masking operation to remove unnecessary regions from the image. Described in detail, the filtering operation is performed with a median smoothing filter, and the masking operation is performed to remove background regions outside the surface of the body, and to remove regions within the body, in which the extraluminal tissues do not exist. Determination as to whether the extraluminal tissues do not exist is made on the basis of numerical values representative of the structure of the tissues corresponding to the pixels in the above-described three-dimensional image.

Described in greater detail in an example in which the three-dimensional image is a CT image and the extraluminal tissues are lymph nodes, Hounsfield values (CT values) representative of the degree of X-ray absorption are used as the numerical values representative of the structure of the tissues corresponding to the pixels in the above-described three-dimensional image. It is anatomically recognized that the lymph nodes do not exist in the imaged regions of bones, blood vessels and air, and that the CT values of the bones, blood vessels and air and the CT values of the lymph nodes fall within respective different ranges. Accordingly, the masking operation performed upon extraction of the lymph nodes is intended to remove the regions of pixels the CT values of which are held within a range of −250 (H.U.) or lower and a range of 300 (H.U.) or higher, in which the lymph nodes do not exist.

Then, the control flow goes to S102 in which regions corresponding to blob structures are extracted from the three-dimensional image subjected to the preliminary operation in S101. Described in detail, the present embodiment is configured to extract the lymph nodes from the three-dimensional image in the form of a CT image, so that candidate regions of the lymph nodes can be suitably removed from the CT image by 3DMinDD process and 3D extended MinDD process proposed in "Assessment of property of three-dimensional cooperative filter for detection of lung cancer from three-dimensional chest CT images", Akinobu Shimizu, Med. Imag. Tech., Vol. 13, No. 6, 1995.

In S102, the extracted candidate regions may be changed if some of the extracted candidate regions are apparently different from the extraluminal tissues such as the lymph nodes, in view of ordinary size and shape of the extraluminal tissues to be extracted. Described in detail, where the contrast between the extracted regions and the other regions is extremely low, the extracted regions may be unnecessarily large. In this case, therefore, the over-extracted candidate regions (FPs) are reduced by local removal on the basis of the ordinary size of the lymph nodes.

The control flow then goes to S103 in which those of the candidate regions extracted in S102 which overlap the luminal organ are removed. Described in detail, the lymph nodes do not exists in the blood vessels, as described above, so that the regions of the blood vessels and the extracted candidate regions of the lymph nodes are compared with each other, on the basis of the organ region information of the luminal organ in the form of the blood vessels stored in the information extracting portion 12. If it is found that the regions of the blood vessels and some of the extracted candidate regions of the lymph nodes overlap each other, those extracted candidate regions overlapping the regions of the blood vessels are removed. In this case, the regions of the blood vessels may be extracted from the three-dimensional image. In the case of the abdominal images, the colonic fold and residual substances in the colon tend to be over-extracted, and these regions should be removed. However, since the CT values of the colonic fold and residual substances may be close to the CT values of the lymph nodes, the over-extraction of the regions of the colonic fold and residual substances cannot be directly detected. Therefore, the region of air within the colon (which is the region other than the colonic fold and residual substances within the colon) is detected, and the detected region of air is enlarged by a suitable ratio to the size of the colon as a whole. Parts of the candidate regions of the lymph nodes which overlap the enlarged region of air are removed.

In S104, some of the extracted candidate regions are removed on the basis of the sizes of the extraluminal tissues. In the present embodiment, those of the candidate regions of the lymph nodes the sizes of which are smaller than a predetermined threshold value are removed. Described in detail, where the lymph nodes having a size not smaller than a predetermined lower limit (e.g., a radius not smaller than 2.5 mm) are to be extracted, the image regions smaller than the lower limit should be removed. Thus, the image regions smaller than the threshold value of the size (e.g., volume of the regions) determined on the basis of the size of the lymph nodes to be extracted should be removed.

In S105, the extracted candidate regions are removed on the basis of the shape of the extraluminal tissues. Thus, any over-extracted region of the candidate regions which has not been removed in the steps up to S104 can be removed. In the present embodiment wherein the lymph nodes to be extracted have an elliptical shape, the candidate regions the shapes of which are apparently distinct from the elliptical shape are removed. Described more specifically, the shape of the candidate regions is determined on the basis of the degree of sphere (DOS) represented by the following equation:

$$DOS=S^3/(36\times\pi\times V^2)$$

In the above equation, S represents a surface area of the candidate regions, and V represents the volume of the candidate regions. The degree of sphere DOS is equal to 1 when the candidate regions has the truly spherical shape, and increases as the shape of the candidate regions becomes non-spherical. The degrees of sphere DOS of the candidate regions are calculated, and the candidate regions the degree of DOS of which are larger than a predetermined threshold value (e.g., 6) are removed.

The candidate regions remaining after the processing described above are determined to be the regions of the lymph nodes. Information indicative of the sizes of those remaining regions and their positions in the three-dimensional image are stored as the extraluminal tissue structure information.

Figure 58:
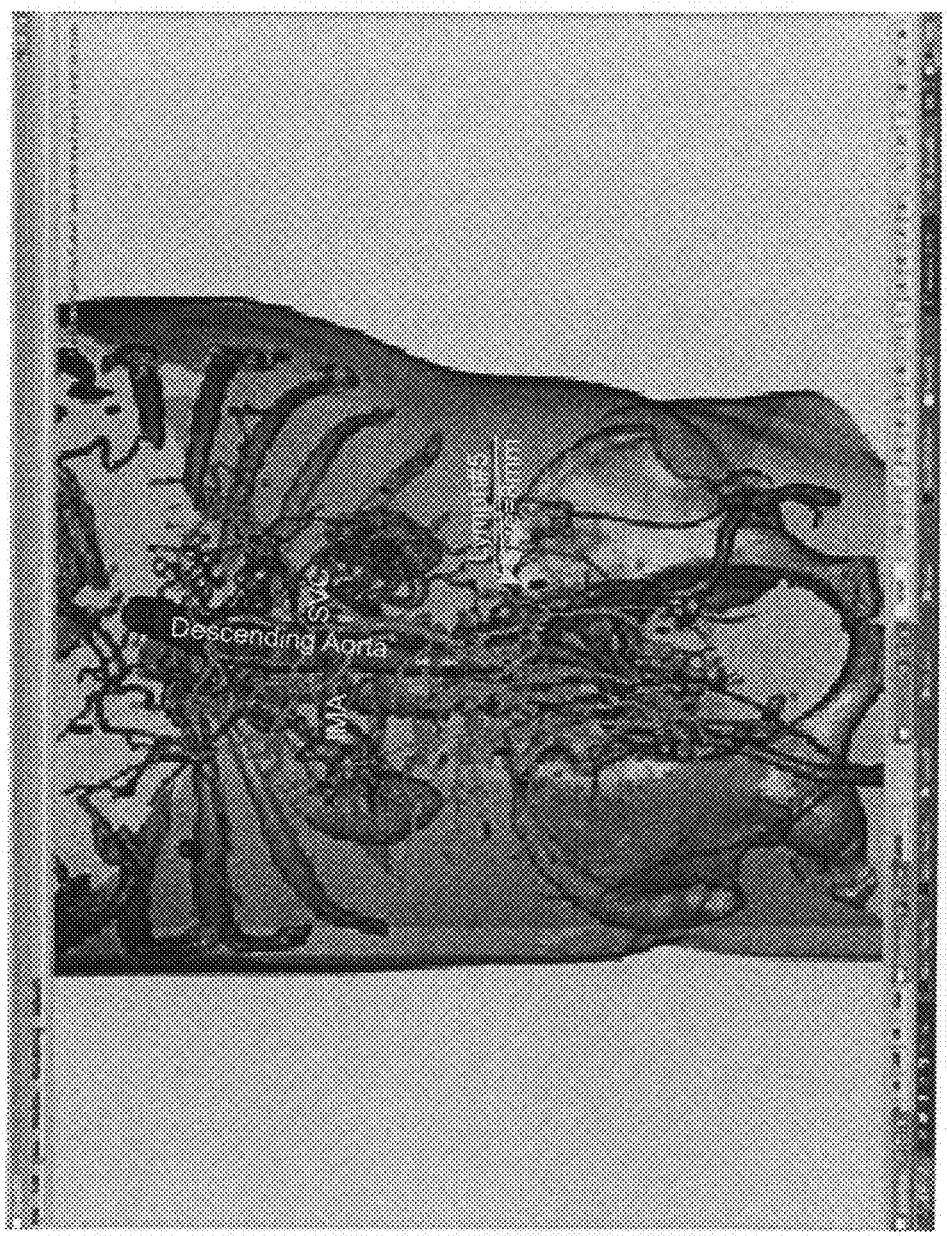
FIG. 58 is a view showing an example of a display provided on the monitor 2 in Embodiment 5.

FIG. 58 shows an example of a virtual image indicating the extraluminal tissue in the form of a lymph node extracted by the extraluminal tissue extracting means 12h, and the luminal organ in the form of a blood vessel. Thus, the luminal organ image generating portion 15 generates the virtual image which maintains the positional relationship in the three-dimensional image in the same scale for the lymph node and the blood vessel, and the anatomical nomenclature generating portion 16 displays the anatomical nomenclature of the blood vessel and the anatomical number of the lymph node such that the anatomical nomenclature and number are superimposed on the virtual image.

The present embodiment is configured such that the extraluminal tissue extracting section 12h extracts extraluminal tissue structure information relating to a structure of an extraluminal tissue existing outside the luminal organ in the subject body, on the basis of the three-dimensional image data, and the luminal organ image generating portion 15 displays the virtual image of the luminal organ and a virtual image of the extraluminal tissue within the same screen in the same scale while maintaining an actual positional relationship between the virtual images. Accordingly, it is possible to recognize in the above-indicated virtual images the position and size of the extraluminal tissue existing outside the luminal organ, on the basis of the above-described three-dimensional image data.

The present embodiment is further configured such that the anatomical information database 13 stores the anatomical structure information including at least the anatomical nomenclature information for the luminal organ and at least the anatomical number for the extraluminal tissue, and the information extracting portion 12 correlates the anatomical nomenclature information of the luminal organ stored in the anatomical information database 13, with the luminal structure data, and correlates the anatomical number of the extraluminal tissue stored in the anatomical information database 13, with the extraluminal tissue structure information. Thus, the information extracting portion 12 correlates the anatomical number with the extraluminal tissue, as well as correlates the anatomical nomenclature with the luminal organ.

The present embodiment is further configured such that the image synthesizing and displaying portion 18 displays the anatomical name of the luminal organ and the anatomical number of the extraluminal tissue on the virtual images displayed on the monitor 2, on the basis of correlation of the anatomical name and the anatomical number by the information extracting portion 12 (extracted information correlating section 12e). Accordingly, the observation of the luminal organ is facilitated.

The present embodiment is further configured such that the luminal organ image generating portion 15 changes the image processing method on the basis of at least one of the anatomical structure information, the organ structure information 37 and the extraluminal tissue structure information. Thus, the luminal organ image generating portion 15 permits automatic or manual change of the image processing method depending upon the specific part of the luminal organ or extraluminal tissue, so that the luminal region data or the extraluminal tissue structure information can be accurately extracted.

The present embodiment is further configured such that when the extraluminal tissue is set as a target portion, the navigating portion 116 sets a portion of the luminal organ which is located close to the extraluminal tissue and into which the endoscope can be inserted, as the target portion of the luminal organ. Accordingly, the operator is merely required to set the extraluminal tissue as the target position, for assistance by the navigating portion 116 to insert the endoscope to the portion of the luminal organ which is located close to the extraluminal tissue and into which the endoscope can be inserted.

The present embodiment is further configured such that the extraluminal tissue is a lymph node, while the luminal organ is a blood vessel. In this case, the extraluminal tissue structure information of the lymph node can be extracted from the three-dimensional image in the form of the CT image, although an image of the lymph node is difficult to appear in the three-dimensional image.

While the embodiments of this invention have been described in detail by reference to the drawings, it is to be understood that the invention may be otherwise embodied.

In the illustrated embodiments, the position sensor 86 and the video camera attached to the leading end portion of the endoscope 84 are extremely small, so that the position of the position sensor 86 estimated by the first real-image observing-position estimating means is used as the observing position of the endoscope 84. However, this estimated position may be compensated on the basis of the actual positional relationship.

The CT-image-data retrieving portion 10 in the illustrated embodiment are configured to retrieve the three-dimensional image data by an MO device or a DVD device, for example. However, the devices used are not limited to those devices. For instance, the three-dimensional image data may be obtained directly from a CT device to which the present assisting system is connected through a network.

In step S33 of FIG. 40, the transformation matrix T is calculated by using only the coordinate system of the position detecting device 82 and the coordinate system of the three-dimensional image. For more accurate calculation of the transformation matrix T, however, it is desirable to define all or selected ones of the coordinate system of the position detecting device 82, the coordinate system of the camera, the coordinate system of the position sensor 86, the coordinate system of the three-dimensional image, and the real coordinate system in which the subject body exists.

In step S34 of FIG. 40, it is determined that the routine is terminated when the routine has been executed a predetermined sufficient number of times. However, it is possible that the routine is repeatedly executed while the position pj is updated, to use the last calculated transformation matrix T.

In the routine of FIG. 46, step S53 may be implemented before step S52. Similarly, step S66 in the routine of FIG. 47 may be implemented before step S65. In the routine of FIG. 57, step S103 may be implemented before step S102. Thus, the order of implementation of the steps in the flow charts may be changed as desired as long as the change causes a problem.

In the Embodiment 3 described above, the virtual image learning portion 102 is not an essential element of the medical image observation assisting system according to the principle of the present invention.

The Embodiment 4 described above is arranged such that the operator is required to specify the target portion for navigation to the target portion by the navigating portion 116. However, this arrangement is not essential. For instance, image diagnosing means is provided in addition to the navigating portion 116 to analyze the three-dimensional image data, for finding a focus portion in the three-dimensional image data, to specify the found focus portion as the target portion. In this instance, the finding of the focus portion and the generation of the path through the luminal organ to the focus portion are automatically implemented.

In the above-described Embodiment 4, the navigating portion 116 is arranged to command the display means in the form of the monitor 2 to navigate the endoscope for insertion. However, this arrangement is essential. In this respect, it is particularly noted that the present invention permits the above-indicated path to be identified by the displayed anatomical nomenclature of the luminal organ. This display of the anatomical nomenclature to identify the path may be replaced by replaced by mechanical generation of sound such as a voice message of the anatomical nomenclature.

In the above-described Embodiment 4, the display of the path nomenclature in S87 of FIG. 51 is not essential as long as the path is displayed according to an operation by the operator.

The above-described Embodiment 4 may be modified such that only S88, S89, S90 and S92 of FIG. 51 are implemented. In this case, the real endoscope image and the virtual image are displayed such that these images can be compared with each other. Similarly, only S88, S89, S90, S91 and S92 may be implemented. In this case, the anatomical nomenclature is superimposed on the real endoscope image and the virtual image that are comparable with each other.

The above-described Embodiment 4 is arranged such that the image synthesizing and displaying portion 18 displays the real endoscope image and the virtual image such that these images can be compared with each other as shown in FIG. 52. However, this arrangement is not essential. for instance, the three-dimensional image may be displayed in addition to the real endoscope image and the virtual image that are comparable with each other, as shown in FIG. 53. Further, the real-image observing position of the real endoscope image and the observing position 75 of the virtual image may be superimposed on the three-dimensional image of FIG. 53.

The above-described Embodiment 4 is further arranged such that a desired one of the plurality of display modes of the image synthesizing and displaying portion 18 is selectable according to an operation by the operator. However, this arrangement is not essential. For example, one of the display modes is automatically selected. Described in detail, the display mode is automatically selected depending upon the situation. When the real endoscope image shows any bifurcated portion, information (namely, arrow 126a and message 126b) for navigation by the navigating portion 116 may be displayed.

In the above-described Embodiment 4, the target portion for which the navigation is implemented by the navigating portion 11 exists within the luminal organ. However, a portion such as the above-described extraluminal tissue existing outside the luminal organ may be set as a pseudo-target portion. In this case, the navigating means is configured to set a portion of the luminal organ which is located close to the pseudo-target portion outside the luminal portion and into which the endoscope can be inserted, as the target portion of the luminal organ. In this case, the operator is navigated to insert the endoscope to the portion of the luminal organ which is close to the pseudo-target portion outside the luminal organ and into which the endoscope can be inserted.

It is to be understood that the foregoing embodiments have been described for illustrative purpose only, and that the present invention may be embodied with various changes and improvements, which may occur to those skilled in the art.

The invention claimed is:

1. A medical image observation assisting system, comprising:
   a volume-region setting portion configured to sequentially set volume regions each enveloping a part of a luminal organ extending within a subject body, on the basis of three-dimensional image data of the subject body, such that the volume regions are adjacent to each other;
   a luminal-organ-region-information calculating portion configured to repeatedly calculate luminal region data in the form of region information of said part of the luminal organ within each of said volume regions set by said volume-region setting portion, on the basis of the three-dimensional image data of the part of the luminal organ within said volume region;

a luminal-organ-structure-information calculating portion configured to calculate luminal structure data in the form of structure information of the part of the luminal organ within the volume region for which said luminal region data has been calculated by said luminal-organ-region-information calculating portion;

a virtual-centerline generating portion configured to generate a virtual centerline extending in a longitudinal direction of said luminal organ, on the basis of said luminal structure data;

a virtual-image generating portion configured to generate a virtual image of said luminal organ along said virtual centerline;

a display portion configured to display said virtual image of said luminal organ;

an observing-position specifying portion configured to determine an observing position for generating said virtual image, on the basis of at least one of said virtual centerline, said luminal region data and said luminal structure data, such that a region of said luminal organ displayed on said display portion has a desired size, and for moving said observing position in the longitudinal direction of said luminal organ, on the basis of said virtual centerline or said luminal structure data;

an anatomical-structure-information storing portion configured to store anatomical structure information including at least anatomical nomenclature information; and an anatomical-nomenclature correlating portion configured to correlate the anatomical nomenclature information stored in said anatomical-structure-information storing portion, with said luminal structure data, and wherein said virtual-image generating portion changes a method of processing said virtual image of the luminal organ, on the basis of said anatomical structure information or said luminal structure data.

2. The medical image observation assisting system according to claim 1, further comprising an image synthesizing portion configured to display anatomical nomenclature information of said luminal organ on the virtual image displayed on said display portion, on the basis of said anatomical nomenclature information which is correlated with said luminal structure data, by said anatomical-nomenclature correlating portion.

3. The medical image observation assisting system according to claim 2, wherein said image synthesizing portion displays a real endoscope image taken by an endoscope actually inserted into said luminal organ of said subject body and said virtual image which corresponds to said real endoscope image and which is generated by said virtual-image generating portion such that said real endoscope image and said virtual image can be compared with each other.

4. The medical image observation assisting system according to claim 2, wherein said image synthesizing portion displays said anatomical nomenclature of said luminal organ on a real endoscope image displayed on said display portion, on the basis of correlation of said anatomical nomenclature by said anatomical-nomenclature correlating portion, said real endoscope image being taken by an endoscope actually inserted into said luminal organ of said subject body.

5. The medical image observation assisting system according to claim 3, further comprising:

a navigating portion configured to display an image for navigating a path from a position of insertion of an endoscope into said luminal organ to a target portion of the luminal organ, and wherein said navigating portion displays an indication of one of a plurality of branches of said luminal organ open at a bifurcated portion thereof indicated on the image displayed on said display portion, said endoscope being advanced into said one of the plurality of branches.

6. The medical image observation assisting system according to claim 3, further comprising:

a navigating portion configured to display an image for navigating a path from a position of insertion of an endoscope into said luminal organ to a target portion of the luminal organ, and wherein said navigating portion automatically generates said path, and displays a plurality of anatomical names correlated by said anatomical-nomenclature correlating portion with respective organs of the luminal organs defining said path, in the order from said position of insertion of the endoscope to said target portion.

7. The medical image observation assisting system according to claim 5, wherein when said extraluminal tissue is set as a pseudo-target portion, said navigating portion sets a portion of said luminal organ which is located close to an extraluminal tissue existing outside said luminal organ in said subject body and into which said endoscope can be inserted, as said target portion of said luminal organ.

8. The medical image observation assisting system according to claim 1, further comprising:

a virtual-image storing portion configured to store each of the plurality of virtual images generated by said virtual-image generating portion, which each virtual image includes a bifurcated portion of said luminal organ, such that said each virtual image is correlated with said luminal structure data corresponding to said each virtual image; and a second real-image observing-position estimating portion configured to extract features which appear on a real endoscope image taken by an endoscope actually inserted into said luminal organ of said subject body and which correspond to the luminal structure data, verifying the extracted features against or with respect to the luminal structure data stored in said virtual-image storing portion, and estimating the observing position of the virtual image corresponding to the luminal structure data verified to match the extracted features, as a real-image observing position which is a position of the leading end portion of said endoscope within said luminal organ.

9. The medical image observation assisting system according to claim 8, wherein said virtual-image generating portion generates said virtual image such that said real-image observing position estimated by said second real-image observing-position estimating portion is determined as said observing position of the virtual image.

10. The medical image observation assisting system according to claim 8, wherein said virtual image and said real endoscope image corresponding to said luminal structure data have at least one feature selected from the number of luminally structural portions, the positions of the luminally structural portions, and the luminosity of the image of the luminally structural portions.

11. The medical image observation assisting system according to claim 8, wherein said virtual-image storing portion comprises a virtual-image learning portion configured to implement learning modification of contents of said virtual-image storing portion, on the basis of a result of the verification of the extracted features with respect to the luminal structure data by the second real-image observing-position estimating portion.

12. A medical image observation assisting system, comprising:

a volume-region setting portion configured to sequentially set volume regions each enveloping a part of a luminal organ extending within a subject body, on the basis of three-dimensional image data of the subject body, such that the volume regions are adjacent to each other;

a luminal-organ-region-information calculating portion configured to repeatedly calculate luminal region data in the form of region information of said part of the luminal organ within each of said volume regions set by said volume-region setting portion, on the basis of the three-dimensional image data of the part of the luminal organ within said volume region;

a luminal-organ-structure-information calculating portion configured to calculate luminal structure data in the form of structure information of the part of the luminal organ within the volume region for which said luminal region data has been calculated by said luminal-organ-region-information calculating portion;

a virtual-centerline generating portion configured to generate a virtual centerline extending in a longitudinal direction of said luminal organ, on the basis of said luminal structure data;

a virtual-image generating portion configured to generate a virtual image of said luminal organ along said virtual centerline;

a display portion configured to display said virtual image of said luminal organ;

an observing-position specifying portion configured to determine an observing position for generating said virtual image, on the basis of at least one of said virtual centerline, said luminal region data and said luminal structure data, such that a region of said luminal organ displayed on said display portion has a desired size, and for moving said observing position in the longitudinal direction of said luminal organ, on the basis of said virtual centerline or said luminal structure data;

an endoscope-position detecting portion configured to detect a relative position of a leading end portion of an endoscope actually inserted into said luminal organ of said subject body; and a first real-image observing-position estimating portion configured to calculate a transformation matrix by comparing the relative position of the leading end portion of the endoscope detected by said endoscope-position detecting portion, with said organ structure data, and converting the relative position of the leading end portion of the endoscope according to the transformation matrix, to thereby estimate a real-image observing-position which is a position of the leading end portion of said endoscope within said luminal organ.

13. The medical image observation assisting system according to claim 12, wherein said virtual-image generating portion generates said virtual image such that said real-image observing position estimated by said first real-image observing-position estimating portion is determined as said observing position of the virtual image.

14. A medical image observation assisting system, comprising:

a volume-region setting portion configured to sequentially set volume regions each enveloping a part of a luminal organ extending within a subject body, on the basis of three-dimensional image data of the subject body, such that the volume regions are adjacent to each other;

a luminal-organ-region-information calculating portion configured to repeatedly calculate luminal region data in the form of region information of said part of the luminal organ within each of said volume regions set by said volume-region setting portion, on the basis of the three-dimensional image data of the part of the luminal organ within said volume region;

a luminal-organ-structure-information calculating portion configured to calculate luminal structure data in the form of structure information of the part of the luminal organ within the volume region for which said luminal region data has been calculated by said luminal-organ-region-information calculating portion;

a virtual-centerline generating portion configured to generate a virtual centerline extending in a longitudinal direction of said luminal organ, on the basis of said luminal structure data;

a virtual-image generating portion configured to generate a virtual image of said luminal organ along said virtual centerline;

a display portion configured to display said virtual image of said luminal organ;

an observing-position specifying portion configured to determine an observing position for generating said virtual image, on the basis of at least one of said virtual centerline, said luminal region data and said luminal structure data, such that a region of said luminal organ displayed on said display portion has a desired size, and for moving said observing position in the longitudinal direction of said luminal organ, on the basis of said virtual centerline or said luminal structure data; and an extraluminal tissue extracting portion configured to extract extraluminal tissue structure information relating to a structure of an extraluminal tissue existing outside said luminal organ in said subject body, on the basis of said three-dimensional image data, and wherein said virtual-image generating portion commands said display portion to display the virtual image of said luminal organ and a virtual image of said extraluminal tissue within the same screen in the same scale while maintaining an actual positional relationship between the virtual images.

15. The medical image observation assisting system according to claim 14, further comprising:

an anatomical-structure-information storing portion configured to store anatomical structure information including at least anatomical nomenclature information for said luminal organ and at least an anatomical number for said extraluminal tissue; and an anatomical-nomenclature correlating portion configured to correlate the anatomical nomenclature information of said luminal organ stored in said anatomicalstructure-information storing portion, with said luminal structure data, and for correlating the anatomical number of said extraluminal tissue stored in the anatomical-structure-information storing portion, with said extraluminal tissue structure information.

16. The medical image observation assisting system according to claim 15, further comprising:
an image synthesizing portion configured to display anatomical name of said luminal organ and the anatomical number of said extraluminal tissue on the virtual images displayed on said display portion, on the basis of said anatomical nomenclature information and said anatomical number which are correlated with said luminal structure data and said extraluminal tissue structure information by said anatomical-nomenclature correlating portion.

17. The medical image observation assisting system according to claim 15, wherein said virtual-image generating portion changes an image processing method on the basis of at least one of said anatomical structure information, said luminal structure data and said extraluminal tissue structure information.

18. The medical image observation assisting system according to claim 14, wherein said extraluminal tissue is a lymph node, while said luminal organ is a blood vessel.

* * * * *